United States Patent
Kandel et al.

(10) Patent No.: US 6,551,821 B1
(45) Date of Patent: Apr. 22, 2003

(54) BRAIN CYCLIC NUCLEOTIDE GATED ION CHANNEL AND USES THEREOF

(75) Inventors: Eric R. Kandel, Riverdale, NY (US); Bina Santoro, Roma (IT); Dusan Bartsch, New York, NY (US); Steven Siegelbaum, New York, NY (US); Gareth Tibbs, New York, NY (US); Seth Grant, Edinburgh (GB)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/997,685

(22) Filed: Dec. 23, 1997

(51) Int. Cl.$^7$ .......................... C07H 21/04; C12N 5/02

(52) U.S. Cl. ............. 435/325; 435/252.33; 435/320.1; 514/44; 536/23.1; 536/23.5

(58) Field of Search ................ 435/69.1, 320.1, 435/252.3, 325, 252–33, 375; 514/44; 536/73.5, 73.1; 530/350

(56) References Cited

PUBLICATIONS

Hillier et al., Genbank–est 109 Database, Accession No. H45591, Jul. 1995.*
Adelman, J. P. et al. (1992) "Calcium–Activated Potassium Channels Expressed from Cloned Complementary DNAs," *Neuron*, 9: 209–216 (Exhibit 2).
Adelman J. P. (1995) "Proteins that Interact with the Pore–Forming Subunits of Voltage–Gated Ion Channels," *Current Opinion in Neurobiology*, 5(3): 286–295 (Exhibit 3).
Aiba, H. et al. (1982) "Molecular Cloning and Nucleotide Sequencing of the Gene for *E. coli* cAMP Receptor Protein," *Nucleic Acids Res.*, 10(4): 1345–1361 (Exhibit 4).
Arancio, O. et al. (1995) "Activity–Dependent Long–Term Enhancement of Trasmitter Release by Presynaptic 3',5'–Cyclic GMP in Cultured Hippocampal Neurons," *Nature*, 376: 74–80 (Exhibit 5).
Atkinson, N. S. et al. (1991) "A Component of Calcium–Activated Potassium Channels Encoded by the Drosophila slo Locus," *Science*, 253(5019): 551–555 (Exhibit 6).
Bolshakov, V. Y. (1997) "Recruitment of New Sites of Synaptic Transmission During the cAMP–Dependent Late Phase of LTP at CA3–CA1 Synapses in the Hippocampus," *Neuron*, 19: 635–651 (Exhibit 7).
Bradley, J. et al. (1997) "Functional Expression of the Heteromeric 'Olfactory' Cyclic Nucleotide–Gated Channel in the Hippocampus: A Potential Effector of Synaptic Plasticity in Brain Neurons," *J. of Neurosci.*, 17(6): 1993–2005 (Exhibit 8).
Bradley, J. et al. (1994) "Heteromeric Olfactory Cyclic Nucleotide–Gated Channels: A Subunit That Confers Increasedd Sensitivity to cAMP," *Proc. Natl. Acad. Sci. USA*, 91: 8890–8894 (Exhibit 9).

Brugge, J. S. et al. (1985) "Neurones Express High Levels of a Structurally Modified Activated Form of pp60$^{c-src}$," *Nature*, 316: 554–557 (Exhibit 10).
Bruggemann, A. et al. (1993) "Ether–a–go–go Encodes a Voltage–Gated Channel Permeable to K$^+$ and Ca$^{2+}$ and Modulated by cAMP," *Nature*, 365: 445–448 (Exhibit 11).
Chen, T. Y. et al. (1993) "A New Subunit of the Cyclic Nucleotide–Gated Cation Channel in Retinal Rods," *Nature*, 362: 764–767 (Exhibit 12).
Erickson, P. F. et al. (1982) "Quantitative Electrophoretic Transfer of Polypeptides from SDS Polyacrylamide Gels to Nitrocellulose Sheets: A Method for Their Re–Use in Immunoautoradiographic Detection of Antigens," *J. Immunol. Methods*, 51: 241–249 (Exhibit 13).
Fields, S. et al. (1989) "A Novel Genetic System to Detect Protein–Protein Interactions," *Nature*, 340: 245–246 (Exhibit 14).
Frey, U. et al. (1993) "Effects of cAMP Simulate a Late Stage of LTP in Hippocampal CA1 Neurons," *Science*, 260: 1661–1664 (Exhibit 15).
Green, W. N. et al. (1995) "Ion–Channel Assembly," *Trends In Neurosci.*, 18: 280–287 (Exhibit 16).
Hoshi, T. (1995) "Regulation of Voltage Dependence of KAT1 Channel by Intracellular Factors," *J. Gen. Physiol.*, 105: 309–328 (Exhibit 17).
Ingram, S. L. et al. (1996) "Modulation of the Hyperpolarization–Activated Current ($I_h$) by Cyclic Nucleotides in Guinea–Pit Primary Afferent Neurons," *J. Physiol.*, 492: 97–227 (Exhibit 18).

(List continued on next page.)

*Primary Examiner*—Nashaat T. Nashed
(74) *Attorney, Agent, or Firm*—John P. White; Cooper & Dunham LLP

(57) ABSTRACT

The present invention provides an isolated nucleic acid molecule encoding a brain cyclic nucleotide gated ion channel (BCNG) protein. An isolated BCNG protein is also provided as is a composition comprising a BCNG encoding nucleic acid or protein or a portion thereof. The present invention also provides a method of identifying an ion channel subunit related protein encoding nucleic acid molecule in a sample. The invention further provides a method for evaluating the ability of a compound to modulate an ion channel associated neurological, cardia, or renal condition. The invention also provides a method for evaluating the ability of a compound to interact with a BCNG-related ion channel subunit protein. Additionally, the present invention provides a method for identifying a compound capable of modulating the activity of a BCNG-related protein. The present invention additionally provides a method of treating a cardiac, renal or neurological condition. Finally, the present invention provides an antibody which specifically reacts with BCNG protein.

10 Claims, 22 Drawing Sheets

PUBLICATIONS

Jenkins, Y. et al. (1992) "A Sequence–Specific Molecular Light Switch: Tethering of an Oligonucleotide to a Dipyridophenazine Complex of Ruthenium(II)," *J. Am. Chem. Soc.*, 114(22): 8736–8738 (Exhibit 19).

Kamb, A. et al. (1987) "Molecular Characterization of Shaker, a Drosophila Gene That Encodes a Potassium Channel," *Cell*, 50(3): 405–413 (Exhibit 20).

Kaupp, U. B. et al. (1989) "Primary Structure and Functional Expression from Complementary DNA of the Rod Photoreceptor Cyclic GMP–Gated Channel," *Nature*, 342: 762–766(Exhibit 21).

Kohler, M. et al. (1996) "Small–Conductance, Calcium–Activated Potassium Channels from Mammalian Brain," *Science*, 273: 1709–1714 (Exhibit 22).

Krapivinsky, G. et al. (1995) "$G_{\beta\gamma}$ Binds Directly to G Protein–Gated $K^+$ Channel, $I_{KACh}$," *J. Biol. Chem.*, 270: 29059–29062 (Exhibit 23).

Lidofsky, S. D. (1996)"Regulation of Cation–Selective Channels in Liver Cells," *J. Membr. Biol.*, 157: 231–236 (Exhibit 24).

Liman, E. R. et al. (1994) "A Second Subunit of the Olfactory Cyclic Nucleotide–Gated Channel Confers High Sensitivity to cAMP," *Neuron*, 13: 611–621 (Exhibit 25).

Martinez, R. (1987) "Neuronal $pp60^{c-src}$ Contains a Six–Amino Acid Insertion Relative to Its Non–Neuronal Counterpart," *Science*, 237: 411–415 (Exhibit 26).

Matthaei, F. S. et al. (1986) "Rapid and Effective Transfer of Integral Membrane Proteins from Isoelectric Focusing Gels to Nitrocellulose Membranes," *Anal. Biochem.*, 157: 123–128 (Exhibit 27).

Marunaka, Y. et al. (1991) "Cyclic GMP–Activated Channel Activity in Renal Epithelial Cells (A6)," *Biochim. Biophys. Acta*, 1070: 152–156 (Exhibit 28).

Pallanck, L. & Ganetzky, B. (1994) "Cloning and Characterization of Human and Mouse Homologs of the Drosophila Calcium–Activated Potassium Channel Gene, Slowpoke," *Hum. Mol. Genet.*, 3: 1239–1243 (Exhibit 29).

Papazian, D. M. et al. (1991) "Alteration of Voltage–Dependence of Shaker Potassium Channel by Mutations in the S4 Sequence," *Nature*, 349(24): 305–310 (Exhibit 30).

Papazian, D. M. et al. (1987) "Cloning of Genomic and Complementary DNA from Shaker, a Putative Potassium Channel Gene from Drosophila," *Science*, 237: 749–753 (Exhibit 31).

Pawson, T. (1995) "Protein Modules and Signalling Networks," *Nature*, 373(16): 573–580 (Exhibit 32).

Pedarzani, P. et al. (1995) "Protein Kinase A–Independent Modulation of Ion Channels in the Brain by Cyclic AMP," *Proc. Natl. Acad. Sci. USA*, 92: 11716–11720 (Exhibit 33).

Santoto, B. et al. (1997) "Interactive Cloning with the SH3 Domain of N–src Identifies a New Brain Specific Ion Channel Protein, with Homology to Eag and Cyclic Nucleotide–Gated Channels," *Proc. Natl. Acad. Sci. USA*, 94: 14815–14820 (Exhibit 34).

Sheng, M. et al. (1994)"Contrasting Subcellular Localization of the Kv1.2 $K^+$ Channel Subunbit in Different Neurons of Rat Brain," *J. Neurosci.*, 14(4): 2408–2417 (Exhibit 35).

Staub, O. et al. (1996) "WW Domain of Nedd4 Bind to the Proline–Rich PY Motifs in the Epithelial $Na^+$ Channel Deleted in Liddle's Syndrome," *EMBO J*, 15(10): 2371–2380 (Exhibit 36).

Strong, M. et al. (1993) "Molecular Evolution of Voltage–Sensitive Ion Channel Genes: On the Origins of Electrical Excitability," *Mol. Biol. Evol.*, 10(1): 221–242 (Exhibit 37).

Sudol, M. (1996) "The WW Module Competes with the SH3 Domain?" *Trends in Biochem. Sci.*, 21: 161–163 (Exhibit 38).

Sugrue, M. M. et al. (1990)"Immunocytochemical Localization of the Neuron–Specific Form of the c–src Gene Product, $pp60^{c-src(+)}$, in Rat Brain," *J. Neurosci.*, 10(8): 2513–2527 (Exhibit 39).

Thomas, M. J. et al. (1996) "Activity–Dependent β–Adrenergic Modulation of Low Frequency Stimulation Induced LTP in the Hippocampal CA1 Region," *Neuron*, 17: 475–482 (Exhibit 40).

Wang, H. et al. (1994) "Localization of Kv1.2, Two K Channel Proteins, to Synaptic Terminals, Somata, and Dendrites in the Mouse Brain," *J.Neurosci.*, 14: 4588–4599 (Exhibit 41).

Warmke, J. W. et al. (1991) "A Family of Potassium Channel Genes Related to Eag in Drosophila and Mammals," *Science*, 91: 3438–3442 (Exhibit 42).

Warmke, J. W. et al. (1991) "A Distinct Potassium Channel Polypeptide Encoded by the Drosophila Eag Locus," *Proc. Natl. Acad. Sci. USA*, 252(5012): 1560–1562 (Exhibit 43).

Weber, I. T. et al. (1989) "Predicted Structure of the cGMP Binding Domains of the cGMP–Dependent Protein Kinase: A Key Alanine/Threonine Difference in Evolutionary Divergence of cAMP and cGMP Binding Sites," *Biochemistry*, 28: 6122–6127 (Exhibit 44).

Zagotta, W. N. et al. (1996) "Structure and Function of Cyclic Nucleotide–Gated Channels," *Annu. Rev. Neurosci.*, 19: 235–263 (Exhibit 45).

Zervos, A. S. et al. (1993) "Mxi1, a Protein That Specifically Interacts with Max to Bind Myc–Max Recognition Sites," *Cell*, 72: 223–232 (Exhibit 46).

Ludwig et al., "A family of hyperpolarization–activated mammalian cation channels," *Nature*, 393:587–591 (1998) Macmillan Journals Ltd.

* cited by examiner

FIG. 1A

```
                                                              50
MEGGGKPNSASNSRDDGNSVFPSKAPATGPVAADKRLGTPPRGGAAGKEH

100
GNSVCFKVDGGGGEEPAGSFEDAEGPRRQYGFMQRQFTSMLQPGVNKFSL

S1            150
RMFGSQKAVEKEQERVKTAGFWIIHPYSDERFYWDLIMLIMMVGNLVIIP

S2                        200
VGITFFTEQTTTPWIIFNVASDTVFLLDLIMNFRTGTVNEDSSEIILDPK

S3                         250
VIKMNYLKSWFVVDFISSIPVDYIFLIVEKGMDSEVYKTARALRIVRFTK

S4                                  300
ILSLLRLLRLSRLIRYIHQWEEIFHMTYDLASAVVRIFNLIGMMLLLCHW

S5                   *              P    350
DGCLQFLVPLLQDFPPDCWVSLNEMVNDSWGKQYSYALFKAMSHMLCIGY

S6                  400
GAQAPVSMSDLWITMLSMIVGATCYAMFVGHATALIQSLDSSRRQYQEKY

450
KQVEQYMSFHKLPADMRQKIHDYYEHRYQGKIFDEENILSELNDPLREEI

500
VNFNCRKLVATMPLFANADPNFVTAMLSKLRFEVFQPGDYIIREGAVGKK
              ------------------------------
                                             550
MYFIQHGVAGVITKSSKEMKLTDGSYFGEICLLTKGRRTASVRADTYCRL
------------------------------------------------
                                             600
YSLSVDNFNEVLEEYPMMRRAFETVAIDRLDRIGKKNSILLQKFQKDLNT
------------------------------------------------
                                ..  .      . 650
GVFNNQENEILKQIVKHDREMVQAIPPINYPQMTALNCTSSTTTPTSRMR
--
        ..             .  ..    .         .. 700
TQSPPVYTATSLSHSNLHSPSPSTQTPQPSAILSPCSYTTAVCSPPIQSP

.          .        .  750
LATRTFHYASPTASQLSLMQQPQQQLPQSQVQQTQTQTQQQQQQQQQQQ

.  800
QQQQQQQQQQQQQQQQQQQQQQQPQTPGSSTPKNEVHKSTQALHNTNL

.     .      .     ..        ..    850
TKEVRPLSASQPSLPHEVSTLISRPHPTVGESLASIPQPVAAVHSTGLQA

.               ..      ..  ....     .  900
GSRSTVPQRVTLFRQMSSGAIPPNRGVPPAPPPPAAVQRESPSVLNTDPD

.
AEKPRFASNL*
```

A  1  2  3  4

B  1  2  3

200 —
132 —

68 —

42 —

30 —

αq1

αq2

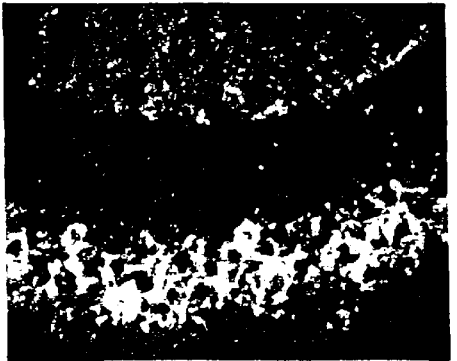
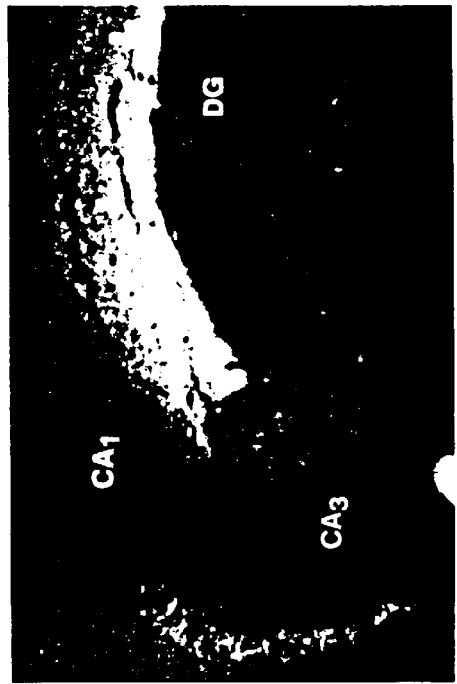

```
mBCNG-1  MEGGGKPNSAGNSRDDGNSVFPSKAPATGPVAADKRLGTPRGGAAGKEHGNSVCFKVDGGGGEEPAGSFEDAEGPRROYGFMQRQFTSMLQPGVNKFSL   100
mBCNG-2  ----------------------------------------------------------------------------------------------
mBCNG-3  ----------------------------------CxQPSAMTAIKVExGAAAxxHILPEAxVRLLG-S------GA-----------
mBCNG-4  ----------------------------------------------------------------------------------------------
hBCNG-1  ----------------------------------------------------------------------------------------------
hBCNG-2  ---------------------------------------EEAGPAGEPRGS-AS------GAL-----------

S1
mBCNG-1  RMFGSQKAVEKEQERVKTAGFWIIHPYSDFRFYWDLIMLIMMVGNLVIIPVGITFFTEQTTTPWIIFRVASDTVFLLDLIMNFRTGTVNEDSSEIILDPK  200
mBCNG-2  ------R-----S-A--------------I-------FT--LF-----I--------KDE--A---V---V--F-M--VL------I-I--NT----E
mBCNG-3  ------x-----R--xS-----------------Tx--LL-----I----------KDEN-----V-----V--F--I--VL------I-V--NT----Q
mBCNG-4  ----------------------------------------------------------------------------------------------
hBCNG-1  ------R-----S-A---------------------FT--LF-----I--------KDE--A-----V---V--F-M--VL------I-I--NT----E

S2
                                       S3                                       S4
mBCNG-1  VIKMNYLKSWFVVDFISSIPVDYIFLIVEKGMDSEVYKTARALRIVRFTKILSLLRLLRLSRLIRYIHQWEEIFHMYDLASAVVRIFNLIGMMLLLCHW   300
mBCNG-2  K--KK--RT-------V----------------I---------------------------------------------------M--C---S---
mBCNG-3  K--F-------RT----V-----------E-x---------V----------------x---------------------------------V---
mBCNG-4  ----------------------------------------------------------------------------------------------
hBCNG-1  K--KK--RT----V-V-----------------I---------------------------------------------------M--C---S---

P                                         S6
mBCNG-1  DGCLQFLVPLLQDFPPDCWVSLNEMVNDSWGKQYSYALFKAMSHMLCIGYGAQAPVSMSDLWITMLSMIVGATCYAMFVGHATALIQSLDSSRRQYEKY  400
mBCNG-2  --------------M-----S-----I-N---H--SEL--F--------------------R---E-T-I-L---------I--------------
mBCNG-3  --------------M-----H-----I-G-----N-------------------------R----G--V-L---------I--------------
mBCNG-4  ----------------------------------------------------------------------------------------------
hBCNG-1  --------------M-----RN----I-G---H--SEL--F--------------------R---E-T-I-L---------I-------------- mBCNG-1  KQVEQYMSFHKLPADMRQKIHDYYEHRYQGKIFDEENILSELNDPLREEIVNFNCRKLVATMPLFANADPNFVTAMLSKLRFEVFQPGDYIIREGAVGKK  500
mBCNG-2  -----------F---------MS--DS--G-----G------------S-----------------------------T-K--------TI--
mBCNG-3  -----------P-T--R----M---S--G--SE---------------S-----------------------------S--T---------TI--
mBCNG-4  --------------------------N------------------------------------------------------------------
hBCNG-1  -----------F---------M---DS--G-----G------------S-----------------------------T-K--------TI--
```

FIG. 8B

```
                                                  CNBs                                                                                600
mBCNG-1    MYFIQHGVAGVITKSSKEMKLTDGSYFGEICLLTKGRRTASVRADTYCRLYSLSVDNFNEVLEEYPMMRRAFETVAIDRLDRIGKKNSILLQKFQKDLNT
mBCNG-2    ------VS-L-GN-----S-----------------R----------------------------------------------T--H-V-H--SS
mBCNG-3    ------VS-L-GN--TR-A-----------------R---x----------------------------------------------------------
mBCNG-4    ---------------------------------------------------------------H--A---F--------M--R---EACLLC-LWLAGPHL
hBCNG-1    ------VS-L-GN-----S-----------------R-------------------------------------------------H-V-H--S
hBCNG-2

700
mBCNG-1    GVFNNQENEILKQTVKHDREMVQAIPPINYPQMTALNCTSSTTTPTSRMRTQSPPVYTATSLSHGNLHSPSPSTQTPQPSAILSPCSYTTAVCSPPIQSP
mBCNG-2    TPRLGPAPTARTAAPSP--RTYQGI
mBCNG-3
mBCNG-4    MSLALVL*
hBCNG-1    -----------------A-----T--S-----------V--
hBCNG-2    --A-IQE---Y-----QAELGQRVGFFPPPPPPQV-SAIATLQ-AAAMSFCPQVA 800
mBCNG-1    LATRTFHYASPTASQLSLMQQPQQQLPQSQVQQTQTQTQXXQQQQQQQQQQQQQQQQQQQQQQQQQQQPQTPGSSTPKNEVHKSTQALHRTNL
mBCNG-2
mBCNG-3
mBCNG-4
hBCNG-1    -A-----------------QP--QV-QSQPPQTPQQPSPQ
hBCNG-2

900
mBCNG-1    TKEVRPLSASQPSLPHEVSTLISRPHPTVGESLASIPQPVAAVHSTGLQAGSRSTVPQRVTLFRQMSSGAIPPNRGVPPAPPPAAVQRESPSVLNTDPD
mBCNG-2
mBCNG-3
mBCNG-4
hBCNG-1    -R-----F--W----------x-----------------T--PG------G---------F--x------L-----L-LITPHPKK
hBCNG-2 mBCNG-1    AEKPRFASNL*
mBCNG-2
mBCNG-3
mBCNG-4
hBCNG-1
hBCNG-2
```

FIG. 9A
He Br Sp Lu Li Mu Ki Te 9.5 —
7.5 —
4.4 —
2.4 —
1.35 — mBCNG-1

FIG. 9B
He Br Sp Lu Li Mu Ki Te 9.5 —
7.5 —
4.4 —
2.4 —
1.35 — mBCNG-2

FIG. 9C
He Br S Lu Li Mu Ki Te 9.5 —
7.5 —
4.4 —
2.4 —
1.35 — mBCNG-3

FIG. 9D
He Br S Lu Li Mu Ki Te 9.5 —
7.5 —
4.4 —
2.4 —
1.35 — mBCNG-4

He Br Pl Lu Li Mu Ki Pa 9.5 —
7.5 —

4.4 —

2.4 —

1.35 — hBCNG-1

He Br Pl Lu Li Mu Ki Pa 9.5 —
7.5 —

4.4 —

2.4 —

1.35 — hBCNG-2

```
KTAARIVRFTKILSLLIRLLIRYIHQW    mBCNG-1
NQAMSLAILRVIRLVRVFRIFKLSRHSKGLQIL    Shaker
KFGWNYPEIRLNRLLRISRMFFFQRTETRTNI    bRET-1
       ★              ★           ★
```

FIG. 14

|   | | | | | | | | | | | | | | |   |
|---|---|---|---|---|---|---|---|---|---|---|---|---|---|---|---|
| Y | L | Y | F | K | A | M | S | H | M | L | C | I | G | Y | G A Q A P V S M | BCNG-1 |
| I | A | F | W | W | A | V | V | T | M | T | T | V | G | Y | G D M T P V G V | SHAK |
| H | L | G | L | W | A | L | I | T | M | S | T | V | G | Y | G D M A P K T Y | SHAW |
| W | C | V | Y | F | L | S | T | T | L | T | V | G | Y | G D | V C E T V | MSLO |
| Y | S | M | Y | W | S | I | T | C | M | T | V | G | Y | G D | L H P V N T | AKT |
| Y | A | L | Y | F | T | F | S | S | L | T | S | V | G | F | G N V A E T D | DEAG |
| Y | I | S | S | L | Y | F | T | M | Y | S | L | T | S | V | G F G N I A P S D | MEAG |
| Y | S | L | Y | W | S | T | L | T | L | T | T | I | G | F | G N - E T P P N | HERG |
| I | R | C | Y | Y | F | A | V | K | T | L | I | T | I | G | - G L P D P K T L | BRET-1 |
|   |   |   |   |   |   |   |   |   |   |   |   |   |   |   |   | HRET-2 |

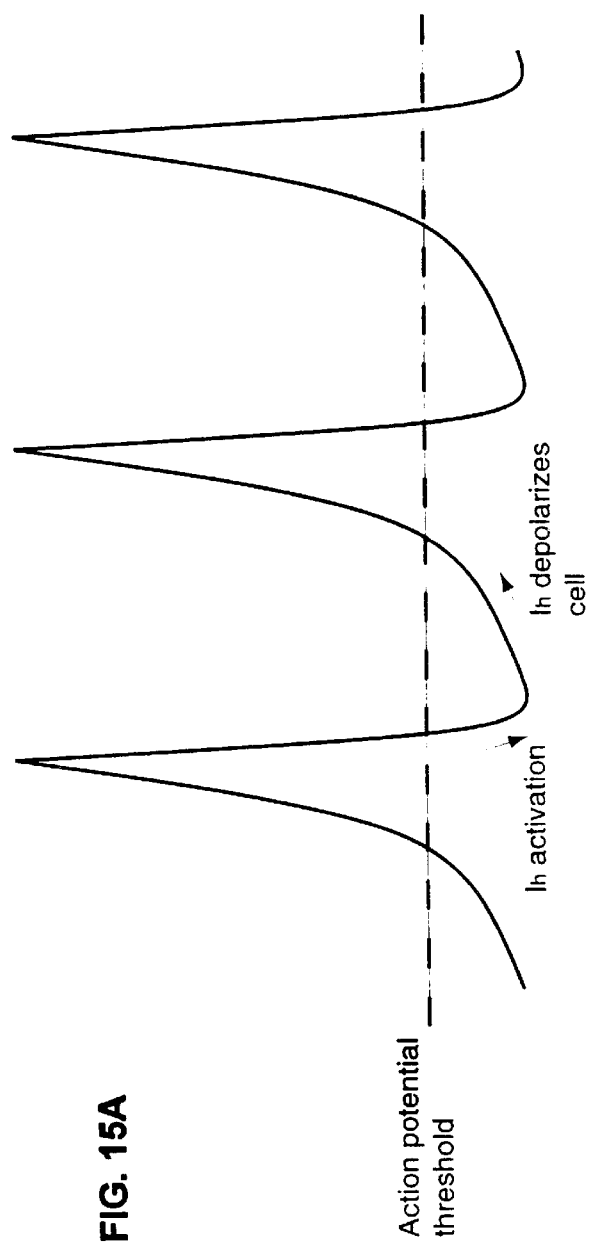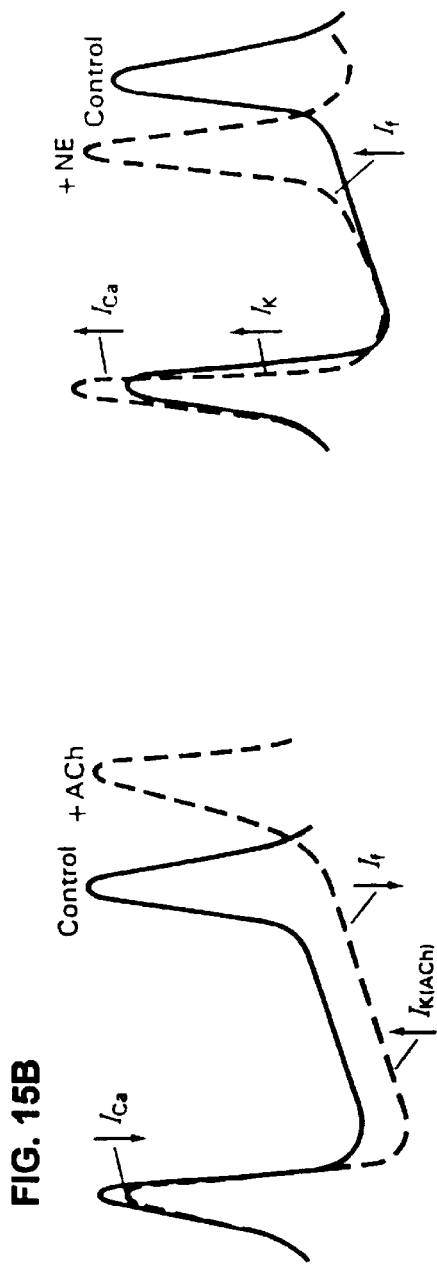
FIG. 15A
FIG. 15B ial ion channel activity has evolved into a rapid and
BRAIN CYCLIC NUCLEOTIDE GATED ION CHANNEL AND USES THEREOF Throughout this application, various publications are referenced by author and date. Full citations for these publications may be found listed alphabetically at the end of the specification immediately preceding the Sequence Listing and the claims. The disclosures of these publications in their entireties are hereby incorporated by reference into this application in order to more fully describe the state of the art.

BACKGROUND OF THE INVENTION

Introduction

Ion channels are a diverse group of proteins that regulate the flow of ions across cellular membranes. In the nervous system, ion channel activity has evolved into a rapid and accurate system for intercellular communication. The electrical excitability characteristics of each neuron is in part determined by the set of channels it expresses. However, cells are also able to regulate the activity of individual channels in response to physiological or developmental events, and there is growing evidence that ion channels can be the site of integration of multiple electrical and biochemical pathways.

In vivo, ion channels appear to be multimeric proteins that are comprised of several distinct gene families, coding for channels with distinct structural and functional properties. Within a gene family, the potential for heterogeneity arising from the combinatorial assembly of different pore-forming and auxiliary subunits (Green, et al., 1995). Channel properties can be modulated by second messenger cascades and can directly bind intracellular proteins such as kinases suggesting that this may be an important way to efficiently target the signaling cascade to its effector molecule. The electrical characteristics of each neuron is, in part, determined by the set of ion channels that it expresses. However, cells are also able to regulate the activity of individual channels in response to physiological or developmental events; pore-forming ($\alpha$) subunits can interact with a variety of intracellular proteins, including auxiliary ($\beta$) subunits, cytoskeleton-associated proteins and protein kinases (Green, et al., 1995). In addition to auxiliary ($\beta$) subunits, pore-forming subunits can interact with a variety of intracellular proteins and second messenger molecules themselves including G-proteins, cytoskeleton-associated proteins and protein-kinases (Adelman, et al., 1995).

Several classes of ion channels bind directly, and are regulated by, second messenger molecules such as cyclic nucleotides (Zagotta, et al., 1996; Bruggemann, et al., 1993, and Hoshi, et al., 1995) or $Ca^{+2}$ (Adelman, et al., 1992; Kohler, et al., 1996). Channels with this property may be key elements in the control of neuronal signaling, as they directly couple biochemical cascades with electrical activity. Cyclic nucleotide-gated channels (CNG) play a distinct role both in visual and olfactory signal transduction; their recent identification in the hippocampus and other regions of the brain, where cAMP and cGMP are known to mediate different forms of synaptic plasticity (Krapivinisky, et al., 1995; Frey, et al., 1993; Boshakov, et al., 1997; and Arancio, et al., 1995), suggests that CNG-channels may also contribute to the regulation of excitability in central neurons (Kingston, et al., 1996 and Bradley, et al., 1997).

The first structural gene for a $K^+$ channel to be isolated was the gene encoded by the Shaker (Sh) locus in Drosophila melanogaster (Strong, et al., 1993; Papazian, et al., 1987). Its sequence is the prototype of a large and still expanding family of related genes (Kamb, et al., 1987; Warmke, et al., 1994). The properties of a number of well characterized $K^+$ currents, that still await a molecular definition, predicts that other members of this family are yet to be identified (Atkinson, et al., 1991).

Although the initial members of the $K^+$ channel superfamily were cloned by chromosomal localization of alleles responsible for functional defects (Sh, eag and slo from Drosophila; (Papazian, et al., 1987; Kamb, et al., 1987; Warmke, et al., 1991; Atkinson, et al., 1991) or following the purification of a relatively abundant protein such as the cGMP-channel from bovine retina (Liman, et al., 1994), the most widely used strategy for cloning new members of the $K^+$ channel superfamily is by homology to these sequences. Unfortunately, this approach is not well suited for identifying more divergent sequences and potentially new branches in the phylogenetic tree of the $K^+$ channel superfamily. Expression cloning in Xenopus oocytes can circumvent this problem; this implies a pre-existing or readily detectable physiological characterization of the channel.

SUMMARY OF THE INVENTION

The present invention provides an isolated nucleic acid molecule having sequence encoding a brain cyclic nucleotide gated (BCNG) ion channel protein or a portion thereof. The present invention additionally provides an isolated BCNG protein. The present invention further provides a composition comprising a nucleic acid, having sequence encoding a BCNG protein or a portion thereof and a carrier. The present invention further additionally provides a composition comprising a BCNG protein or portion thereof and a carrier.

In addition, the present invention provides a method of identifying a nucleic acid encoding an ion channel subunit-related protein in a sample which comprises detecting in the sample a nucleic acid molecule encoding a BCNG-related protein, positive detection indicating the presence of an ion channel subunit related protein encoding nucleic acid molecule, thereby identifying a nucleic acid encoding an ion channel subunit-related protein in the sample.

The present invention also provides a method for evaluating the ability of a compound to modulate an ion channel associated with a condition in a subject which comprises:(a) contacting a cell which expresses a BCNG-related protein in a cell culture with a compound; (b) determining the amount of BCNG-related protein expression in the cell culture; and (c) comparing the amount of BCNG-related protein expression determined in step (b) with the amount determined in the absence of the compound so as to evaluate the ability of the compound to modulate the ion channel associated with the condition in the subject.

The present invention also provides a method for evaluating the ability of a compound to interact with a BCNG-related ion channel subunit protein which comprises: (a) contacting a cell which expresses a BCNG-related protein in a cell culture with a compound under conditions permissive to formation of a complex between the compound and the BCNG-related protein; (b) determining the amount of complex formed between the compound and the BCNG-related protein in the cell culture; and (c) comparing the amount of complex formed in step (b) with the amount formed in the absence of the compound so as to evaluate the ability of the compound to interact with a BCNG-related ion channel subunit protein.

Additionally, the present invention provides a method for identifying whether a compound is capable of modulating a dysfunction in an animal comprising:(a) administering the compound to the animal under conditions permissive to formation of a complex between the compound and the BCNG-related protein; (b) determining the amount of complex formed between the compound and the BCNG-related protein in the animal; and (c) comparing the amount of complex formed in step (b) with the amount of complex formed in the animal in the absence of the compound so as to identify whether the compound is capable of modulating the dysfunction in the animal, a change in the amount of complex formed in the presence of the compound indicating that the compound is capable of modulating dysfunction in the animal.

Further, the present invention provides a method of identifying a compound which modulates the activity of BCNG-related protein which comprises: (a) introducing the nucleic acid of claim 1 into an expression system and causing the expression system to express the nucleic acid under conditions whereby an ion channel subunit protein is produced;(b) contacting the channel subunit protein with the compound; (c) determining the activity of the ion channel subunit protein; and (d) comparing the activity determined in step (c) with the activity determined in the absence of the compound, an increase or decrease in activity in the presence of the compound indicating identification of a compound which modulates the activity of BCNG-related protein.

The present invention also provides a pharmaceutical composition which comprises a compound capable of modulating BCNG-related protein activity and a pharmaceutically acceptable carrier. According to an embodiment of this invention, the carrier is a diluent, an aerosol, a topical carrier, an aqueous solution, a nonaqueous solution or a solid carrier.

Finally, the present invention provides an antibody that specifically binds to BCNG protein.

BRIEF DESCRIPTION OF THE FIGURES

FIG. 1A: Predicted amino acid sequence encoded by the mBCNG-1 cDNA (SEQ ID NO:1). The seven hydrophobic domains, homologous to the six transmembrane domains (S1–S6) and the pore (P) of K$^+$ channels, are indicated. The putative cyclic-nucleotide binding site (CNB) is marked by dashes, the C-terminal prolines are indicated by dots, and the consensus N-glycosylation site with presumptive extracellular localization is marked by an asterisk.

(FIG. 2A) Western blot analysis of BCNG-1 protein in a mouse brain extract. Ten μg of a total brain SDS-extract was loaded per strip then probed with αq1 (1) or αq2 (3) antiserum or, strip 2 with αq1 (2) or αq2 (4) antiserum preadsorbed with the GST-d5 fusion protein. The arrow marks the position of the specific signal, of corresponding to the native BCNG-1 protein. (FIG. 2B) Western blot using the αq1 antiserum against: total brain extract (1), total brain extract pretreated with N-glycosidase F (2) and in vitro translated BCNG-1 protein (3). Positions of molecular weight standards are shown on the left. Also shown, Western blot containing 10 μg of proteins from each of the indicated brain tissues which was tested with antisera against mBCNG-1 and showing widespread expression of the mBCNG-1 protein in mouse brain. (FIG. 2C) indicates reactivity with αq1. (FIG. 2D) indicates reactivity with αq2.

FIGS. 5A–5F: Immunohistochemical analysis of BCNG-1 expression in the brain. Parasagittal sections of a mouse brain were stained with αq1 and αq2 antisera. The patterns of BCNG-1 expression detected with the two different antisera were identical, and in both cases the staining was entirely abolished by preadsorbing the sera with the GST-d5 fusion protein. BCNG-1 immunoreactivity in the cerebral cortex. (FIG. 5C), and (FIG. 5D): BCNG-1 immunoreactivity in the hippocampus. In (FIG. 5C), the arrow shows the position of the hippocampal fissure; areas $CA_1$, $CA_3$ and dentate gyrus (DG) are labeled, and; (FIG. 5D) shows a detail of the stratum pyramidale of area $CA_3$. (FIG. 5E) and (FIG. 5F): BCNG-1 immunoreactivity in the cerebellum (FIG. 5A, FIG. 5C, FIG. 5E: 60×; FIG. 5B, FIG. 5D, FIG. 5F: 100×) magnification).

FIGS. 8A–B: Alignment of the predicted amino acid sequence of mBCNG-1 (SEQ ID NO:2) with the predicted sequences of the three additional mouse genes, mBCNG-2 (SEQ ID NO:4), mBCNG-3 (SEQ ID NO:6), and mBCNG-4 (SEQ ID NO:8) and two human genes, hBCNG-1 and 2, SEQ ID NOS:10 and 12, respectively. The proposed structural features of the protein (putative transmembrane regions, the pore region and the cyclic nucleotide binding site) are indicated. A dash (-) indicates residues identical to mBCNG-1, divergent residues are otherwise reported. An "x" indicates residues not determined, a dot indicates a gap (or deletion) in the aligned sequence, an asterisk (*) at the end of the sequence indicates a stop codon, and the asterisk above position 327 marks an N-glycosylation site of mBCNG-1.

FIGS. 9A–9D. Northern blot analysis of mouse BCNG genes. A Multiple Tissue Northern blot, containing 2 mg of polyA+ RNA from each of the following mouse tissues: heart (He), brain (Br), spleen (Sp), lung (Lu) liver (Li), skeletal muscle (Mu), kidney (Ki) and testis (Te), was hybridized to DNA fragments corresponding to the indicated BCNG genes. Molecular size markers are indicated on the left.

FIG. 12:Alignment of the S4 voltage sensing region of mBCNG-1 (SEQ ID NO:50) with the S4 voltage sensing regions of the prototypical voltage-gated potassium channel "Shaker" (SEQ ID NO:51) and the cyclic nucleotide-gated channel "bRET1" (SEQ ID NO:52). Boxed residues are positively charged amino acids present in one or more of the S4 sequences, stars indicate the position of amino acids with negatively charged acidic side chains that are present in the bRET1 sequence.

FIG. 14: Multiple alignment of the putative P region of mBCNG-1 (SEQ ID NO:35) with the P regions of prototypical potassium channel proteins of the Shaker, plant inward rectifier and Eag subfamilies. Shown in the alignment are the P regions of Shaker (SEQ ID NO:36) (SHAK, Papazian et al., 1987; Kamb et al., 1988), the Shaker-related channels, SHAW (SEQ ID NO:37) (Wei, et al., 1990) and the calcium-activated K channel, MSLO (SEQ ID NO:38) (Pallanck and Ganetzky, 1994), the plant inward rectifier, AKT (SEQ ID NO:39) (Sentenac et al., 1992), and the Eag-related channels, Drosophila ether-a-gogo, DEAG (SEQ ID NO:40) (Warmke et al., 1991), mouse ether-a-gogo, MEAG (SEQ ID NO:41) (Warmke and Ganetzky, 1994) and the human ether-a-gogo-related gene, HERG (SEQ ID NO:42) (Warmke and Ganetzky, 1994). Also shown are subunits of cyclic nucleotide-gated channels, the bovine retinal α-subunit, BRET1 (SEQ ID NO:43) (Kaupp et al., 1989), and human retinal β subunit, HRET-2 (SEQ ID NO:44) (Chen et al., 1993). Arrows mark positions where the BCNG channels show pronounced and potentially important changes in sequence from the normal motif seen in selective channels. (See page 66 of the specification).

FIGS. 15A–15B. Schematic representation of repetitive firing of a pacemaker neuron and its involvement in the generation and regulation of rhythmic firing patterns. (FIG. 15A) Shows that Ih activation upon hyperpolarization following an action potential. As this is a non-selective cationic current, it carries an inward current at these potentials which leads to the depolarization of the cell back towards the threshold for firing of the next action potential. (FIG. 15B) Shows the action of sympathetic and vagal stimulation on the activity of cardiocytes from the sinoatrial node—the pacemaker area of the heart. Norepinephrine (NE) leads to a shift in the activation of Ih towards more depolarized potentials which accelerates the return to the action potential firing threshold, and hence, leads to an acceleration of the firing rate. In contrast, acetylcholine (ACh) shifts the activation of Ih to more hyperpolarized potentials. Thus, the current will turn on later during the repolarization phase delaying the return to threshold—the firing rate of the cell will thus be slowed. These changes in the activation properties of Ih are thought to be due to changes in the concentration of cAMP with ACh lowering the concentration and NE increasing the concentration which has been shown to alter the activation properties of Ih. ("Principles of Neural Science" by Kandel, Schwartz and Jessell 1991).

DETAILED DESCRIPTION OF THE INVENTION

Figure 1B:
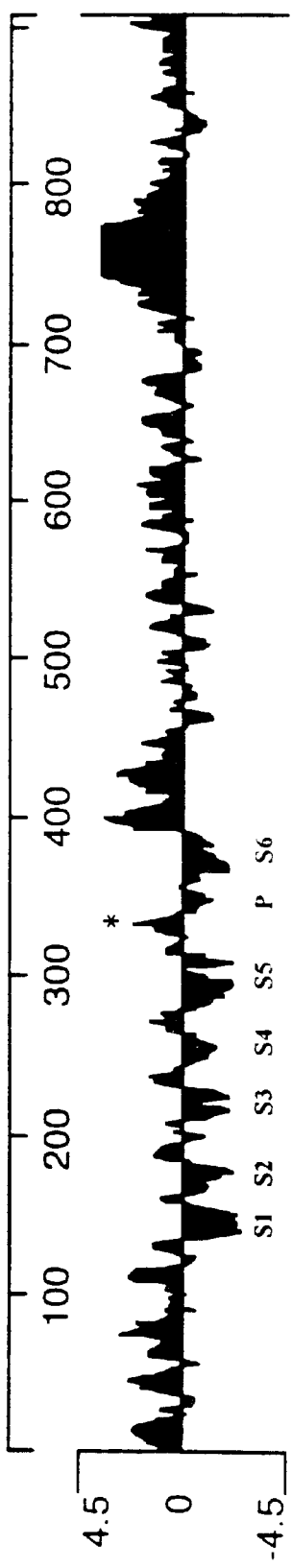
FIG. 1B: Kyte and Doolittle hydropathy plot of the predicted amino acid sequence of mBCNG-1 (SEQ ID NO:2). Hydrophobic regions corresponding to S1 through S6 and the P region lie below the zero line while the N-glycosylation site (*) is in a hydrophilic region between S5 and P. Numbering (top line) indicates position in the sequence, profile generated with a window size of 7 residues.

The present invention provides an isolated nucleic acid molecule (SEQ ID NO:1) encoding a BCNG ion channel protein or a portion thereof. In one embodiment of the present invention, the nucleic acid molecule is mBCNG-2 (SEQ ID NO:3), mBCNG-3 (SEQ ID NO:5), mBCNG-4 (SEQ ID NO:7), hBCNG-1 (SEQ ID NO:9) or hBCNG-2 (SEQ ID NO:11).

In an embodiment of the present invention, the nucleic acid molecule is DNA. In another embodiment of the invention, the nucleic acid molecule is RNA. In yet another embodiment of the present invention, the DNA is cDNA.

In one embodiment of this invention, the cDNA has substantially the same coding sequence as the coding sequence shown in SEQ ID NO:1, SEQ ID NO:3, SEQ ID NO:5, SEQ ID NO:7, SEQ ID NO:9 or SEQ ID NO:11.

In still another embodiment the present invention is a vector comprising the nucleic acid. In one embodiment of this invention, the vector is a virus. In another embodiment of this invention, the vector is a plasmid.

Another embodiment of this invention is a host-vector system for the production of a mammalian BCNG molecule which comprises the vector in a suitable host. In an embodiment of this invention, the suitable host is a bacterial cell, a eukaryotic cell, a mammalian cell or an insect cell.

Another embodiment of the present invention is a nucleic acid molecule capable of specifically hybridizing with the nucleic acid molecule encoding a BCNG-related protein.

Still another embodiment of the present invention is an isolated BCNG protein (SEQ ID NO:2). In an embodiment of this invention, the BCNG protein is mBCNG-2 (SEQ ID NO:4), mBCNG-3 (SEQ ID NO:6), mBCNG-4 (SEQ ID NO:8), hBCNG-1 (SEQ ID NO:10) or and hBCNG-2 (SEQ ID NO:12). In another embodiment of this invention, the protein has substantially the same amino acid sequence as the amino acid sequence shown in SEQ ID NO:2, SEQ ID NO:4, SEQ ID NO:6, SEQ ID NO:8, SEQ ID NO:10, or SEQ ID NO:12.

Still another embodiment of the present invention is a composition comprising a nucleic acid, encoding a BCNG protein or a portion thereof and a carrier. In an embodiment of this invention, the nucleic acid comprises substantially the same sequence as that shown in SEQ ID NO:1, SEQ ID NO:3, SEQ ID NO:5, SEQ ID NO:7, SEQ ID NO:9, SEQ ID NO:11 or portion thereof. In a further embodiment, the composition comprises a BCNG protein or portion thereof and a carrier. In one embodiment, the BCNG protein comprises substantially the same amino acid sequence as the amino acid sequence shown in SEQ ID NO:2, SEQ ID NO:4, SEQ ID NO:6, SEQ ID NO:8, SEQ ID NO:10, SEQ ID NO:12 or a portion thereof.

In addition, the present invention provides a method of identifying a nucleic acid encoding an ion channel subunit-related protein in a sample which comprises detecting in the sample a nucleic acid molecule encoding a BCNG-related protein, positive detection indicating the presence of an ion channel subunit related protein encoding nucleic acid molecule, thereby identifying a nucleic acid encoding an ion channel subunit-related protein in the sample.

In an embodiment of the present invention, the nucleic acid molecule encoding the ion channel subunit-related protein is detected by size fractionation. In an embodiment of this invention, the size fractionation is effected by a polyacrylamide or an agarose gel.

In an embodiment of this invention, the detection of the nucleic acid molecule encoding the BCNG-related protein comprises contacting the sample with a second nucleic acid molecule capable of hybridizing with the nucleic acid molecule encoding the BCNG-related protein, wherein the second nucleic acid molecule is labeled with a detectable marker under conditions permitting the second nucleic acid molecule to hybridize with the nucleic acid molecule encoding the BCNG-related protein, thereby identifying the nucleic acid molecule in the sample.

In one embodiment of this invention, the second nucleic acid molecule is capable of hybridizing to mBCNG-1 (SEQ ID NO:1), mBCNG-2 (SEQ ID NO:3), mBCNG-3 (SEQ ID NO:5), mBCNG-4 (SEQ ID NO:7), hBCNG-1 (SEQ ID NO:9) or hBCNG-2 (SEQ ID NO:11). In one embodiment of the invention, the detectable marker is a radiolabeled molecule, a fluorescent molecule, an enzyme, a ligand, or a magnetic bead.

In an embodiment of this invention, the detection of the nucleic acid molecule encoding the BCNG-related protein comprises amplifying the nucleic acid molecule encoding the BCNG-related protein, thereby identifying the nucleic acid molecule encoding the BCNG-related protein in the sample. In one embodiment of the invention, the amplification of the nucleic acid molecule encoding the BCNG-related protein comprises contacting the nucleic acid molecule from the sample with at least one primer capable of hybridizing to mBCNG-1 (SEQ ID NO:1), mBCNG-2 (SEQ ID NO:3), mBCNG-3 (SEQ ID NO:5), mBCNG-4 (SEQ ID NO:7), hBCNG-1 (SEQ ID NO:9) or hBCNG-2 (SEQ ID NO:11) under conditions suitable for the polymerase chain reaction.

In an embodiment of this invention, the amplified nucleic acid molecule encoding the BCNG-related protein is detected by size fractionation. In an embodiment of this invention, the size fractionation is via a polyacrylamide gel or an agarose gel.

The present invention also provides a method for evaluating the ability of a compound to modulate an ion channel associated with a condition in a subject which comprises:(a)

contacting a cell which expresses a BCNG-related protein in a cell culture with a compound; (b) determining the amount of BCNG-related protein expression in the cell culture; and (c) comparing the amount of BCNG-related protein expression determined in step (b) with the amount determined in the absence of the compound so as to evaluate the ability of the compound to modulate the ion channel associated with the condition in the subject.

In an embodiment of this invention, the condition is a neurological condition, cardiovascular condition, renal condition, pulmonary condition, or hepatic condition. In one embodiment of this invention, the condition is epilepsy, Alzheimer's Disease, Parkinson's Disease, long QT syndrome, sick sinus syndrome, age-related memory loss, cystic fibrosis, sudden death syndrome or a pacemaker rhythm dysfunction.

In an embodiment of this invention, the BCNG-related protein comprises mBCNG-1 (SEQ ID NO:2), mBCNG-2 (SEQ ID NO: 4), mBCNG-3 (SEQ ID NO:6), mBCNG-4 (SEQ ID NO:8), hBCNG-1 (SEQ ID NO:10) or hBCNG-2 (SEQ ID NO:12) or a portion thereof.

In an embodiment of this invention, the cell is a cardiac cell, a kidney cell, a hepatic cell, an airway epithelial cell, a muscle cell, a neuronal cell, a glial cell, a microglial cell, an endothelial cell, a mononuclear cell, a tumor cell, a mammalian cell, an insect cell, or a Xenopus oocyte.

In an embodiment of this invention, the compound is a peptide, a peptidomimetic, a nucleic acid, a polymer, or a small molecule. In one embodiment of this invention, the compound is bound to a solid support.

The present invention also provides a method for evaluating the ability of a compound to interact with a BCNG-related ion channel subunit protein which comprises: (a) contacting a cell which expresses a BCNG-related protein in a cell culture with a compound under conditions permissive to formation of a complex between the compound and the BCNG-related protein; (b) determining the amount of complex formed between the compound and the BCNG-related protein in the cell culture; and (c) comparing the amount of complex formed in step (b) with the amount formed in the absence of the compound so as to evaluate the ability of the compound to interact with a BCNG-related ion channel subunit protein.

According to one embodiment of this invention, the BCNG-related protein comprises mBCNG-1 (SEQ ID NO:2), mBCNG-2 (SEQ ID NO:4), mBCNG-3 (SEQ ID NO:6), mBCNG-4 (SEQ ID NO:8), hBCNG-1 (SEQ ID NO:10) or hBCNG-2 (SEQ ID NO:12) or a portion thereof.

In an embodiment of the present invention, the cell is a cardiac cell, a kidney cell, a hepatic cell, an airway epithelial cell, a muscle cell, a neuronal cell, a glial cell, a microglial cell, an endothelial cell, a mononuclear cell, a tumor cell, a mammalian cell, an insect cell, or a Xenopus oocyte.

In an embodiment of this invention, the compound is a peptide, a peptidomimetic, a nucleic acid, a polymer, or a small molecule. In one embodiment, the compound is bound to a solid support.

Additionally, the present invention provides a method for identifying whether a compound is capable of modulating a dysfunction in an animal comprising: (a) administering the compound to the animal under conditions permissive to formation of a complex between the compound and the BCNG-related protein; (b) determining the amount of complex formed between the compound and the BCNG-related protein in the animal; and (c) comparing the amount of complex formed in step (b) with the amount of complex formed in the animal in the absence of the compound so as to identify whether the compound is capable of modulating the dysfunction in the animal, a change in the amount of complex formed in the presence of the compound indicating that the compound is capable of modulating dysfunction in the animal. In one embodiment of this invention is a the condition is a neurological condition, cardiovascular condition, renal condition, pulmonary condition, or hepatic condition. In yet another embodiment, the condition is epilepsy, Alzheimer's Disease, Parkinson's Disease, long QT syndrome, sick sinus syndrome, age-related memory loss, cystic fibrosis, sudden death syndrome or a pacemaker rhythm dysfunction.

Further, the present invention provides a method of identifying a compound which modulates the activity of BCNG-related protein which comprises: (a) introducing the nucleic acid of claim 1 into an expression system and causing the expression system to express the nucleic acid under conditions whereby an ion channel subunit protein is produced;(b) contacting the channel subunit protein with the compound; (c) determining the activity of the ion channel subunit protein; and (d) comparing the activity determined in step (c) with the activity determined in the absence of the compound, an increase or decrease in activity in the presence of the compound indicating identification of a compound which modulates the activity of BCNG-related protein.

In one embodiment of this invention, the activity determination step (c) comprises measuring the channel electrical current or intracellular calcium level in the presence of the compound. In another embodiment, the detection is by a florescence-activated cell sorter (FACS) or by a video imaging system. In another embodiment of this invention, the detection is in a high throughput screening system. In another embodiment of this invention, the expression system comprises a cultured host cell. In another embodiment, the host cell is a cardiac cell, a kidney cell, a hepatic cell, an airway epithelial cell, a muscle cell, a neuronal cell, a glial cell, a microglial cell, an endothelial cell, a mononuclear cell, a tumor cell, a mammalian cell, an insect cell, or a Xenopus oocyte.

The present invention also provides a pharmaceutical composition which comprises a compound capable of modulating BCNG-related protein activity and a pharmaceutically acceptable carrier. According to an embodiment of this invention, the carrier is a diluent, an aerosol, a topical carrier, an aqueous solution, a nonaqueous solution or a solid carrier.

One embodiment of this invention is a method for treating a condition in a subject which comprises administering to the subject an amount of the pharmaceutical composition effective to treat the condition in the subject. In an embodiment of this invention, the condition is a neurological condition, renal condition, pulmonary condition, hepatic condition, or cardiovascular condition. In an embodiment of this invention, the condition is epilepsy, Alzheimer's Disease, Parkinson's Disease, long QT syndrome, sick sinus syndrome, age-related memory loss, cystic fibrosis, sudden death syndrome or a pacemaker rhythm dysfunction. In still another embodiment of this invention, the subject is a human.

The present invention further provides a method of treating a condition in a subject which comprises administering to the subject an effective amount of a compound which modulates the activity of BCNG-related protein, so as to treat the condition. In an embodiment of this invention, the condition is a neurological condition, cardiovascular condition, renal condition, pulmonary condition, or hepatic condition. In another embodiment of this invention, the condition is epilepsy, Alzheimer's Disease, Parkinson's Disease, long QT syndrome, sick sinus syndrome, age-related memory loss, cystic fibrosis, sudden death syndrome or a pacemaker rhythm dysfunction.

Finally, the present invention provides an antibody that specifically binds to BCNG protein. One embodiment of this invention is a cell line producing the antibody specific for BCNG-related protein. Another embodiment of the present invention is a method of identifying the BCNG protein in a sample comprising: a) contacting the sample with the antibody which specifically binds to the BCNG protein under conditions permissive to the formation of a complex between the antibody and the protein; b) determining the amount of complex formed; and c) comparing the amount of complex formed in step (b) with the amount of complex formed in the absence of the antibody, the presence of an increased amount of complex formed in the presence of the antibody indicating identification of the protein in the sample.

The degree of hybridization depends on the degree of complementarity, the length of the nucleic acid molecules being hybridized, and the stringency of the conditions in a reaction mixture. Stringency conditions are affected by a variety of factors including, but not limited to temperature, salt concentration, concentration of the nucleic acids, length of the nucleic acids, sequence of the nucleic acids and viscosity of the reaction mixture. More stringent conditions require greater complementarity between the nucleic acids in order to achieve effective hybridization.

A preferred method of hybridization is blot hybridization. See Sambrook et al. 1989 *Molecular Cloning: A Laboratory Manual* 2nd Ed. for additional details regarding blot hybridization.

The second nucleic acid molecule specifically hybridizes to a particular sequence which is bound nonspecifically to the solid matrix. The second nucleic acid molecule can be DNA or RNA and can be labeled with a detectable marker. Such labeling techniques methods include, but are not limited to, radio-labeling, digoxygenin-labeling, and biotin-labeling.

A well-known method of labeling DNA is $^{32}$P using DNA polymerase, Klenow enzyme or polynucleotide kinase. In addition, there are known non-radioactive techniques for signal amplification including methods for attaching chemical moieties to pyrimidine and purine rings (Dale, R. N. K. et al., 1973 *Proc. Natl. Acad. Sci. USA* 70:2238–42), methods which allow detection by chemiluminescence (Barton, S. K. et al., 1992 *J. Am. Chem. Soc.* 114:8736–40) and methods utilizing biotinylated nucleic acid probes (Johnson, T. K. et al., 1983 *Anal. Biochem.* 133:125–131; Erickson, P. F. et al., 1982 *J. Immunol. Methods* 51:241–49; Matthaei, F. S. et al., 1986 *Anal. Biochem.* 157–123–28) and methods which allow detection by fluorescence using commercially available products. Non-radioactive labelling kits are also commercially available.

Nucleic acid amplification is described in Mullis, U.S. Pat. No. 4,683,202, which is incorporated herein by reference.

In a polymerase chain reaction (PCR), an amplification reaction uses a template nucleic acid contained in a sample can use one or more primer sequences and inducing agents.

Suitable enzymes to effect amplification, specifically extension include, for example, *E.coli* DNA polymerase I, thermostable Taq DNA polymerase, Klenow fragment of *E.coli* DNA polymerase I, T4 DNA polymerase, other available DNA polymerases, reverse transcriptase and other enzymes which will facilitate covalent linkage of the nucleotides to polynucleotides which are form amplification products. The oligonucleotide primers can be synthesized by automated instruments sold by a variety of manufacturers or can be commercially prepared.

Solid matrices are available to the skilled artisan. A solid matrix may include polystyrene, polyethylene, polypropylene, polycarbonate, or any solid plastic material in the shape of test tubes, beads, microparticles, dip-sticks, plates or the like. Additionally matrices include, but are not limited to membranes, 96-well microtiter plates, test tubes and Eppendorf tubes. Solid phases also include glass beads, glass test tubes and any other appropriate shape made of glass. A functionalized solid phase such as plastic or glass which has been modified so that the surface carries carboxyl, amino, hydrazide, or aldehyde groups can also be used. In general such matrices comprise any surface wherein a ligand-binding agent can be attached or a surface which itself provides a ligand attachment site.

In the practice of any of the methods of the invention or in the preparation of any of the pharmaceutical compositions of the present invention a "therapeutically effective amount" is an amount which is capable of modulating the activity or function of a BCNG-related protein. Accordingly, the effective amount will vary with the subject being treated, as well as the condition to be treated. The methods of administration may include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions capable of inhibiting neurotoxicity together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The carrier includes a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

mBCNG-1 cDNA was deposited on Apr. 21, 1998 with the American Type Culture Collection, 10801 University Blvd., Manassas, Va., 20110-2209, U.S.A., pursuant to the provisions of the Budapest Treaty on the International Recognition of the Microorganism Deposit for the Purposes of Patent Procedure and have been accorded ATCC Designation No.209781. In addition, the following cDNAs have been deposited on May 1, 1998 with the American Type Culture Collection, 10801 University Blvd., Manassas, Va., 20110-2209, U.S.A., pursuant to the provisions of the Budapest Treaty on the International Recognition of the Microorganism Deposit for the Purposes of Patent Procedure and have been accorded the ATCC Designation Nos. indicated:

cDNA of mBCNG-3a ATCC Designation No: 209824
cDNA of mBCNG-2a ATCC Designation No: 209825
cDNA of mBCNG-2b ATCC Designation NO.: 209826
cDNA of hBCNG-1 ATCC Designation NO.: 209827
cDNA of mBCNG-3b ATCC Designation NO.: 209828.

This invention is illustrated in the Experimental Details section which follows. These sections are set forth to aid in an understanding of the invention but are not intended to, and should not be construed to, limit in any way the invention as set forth in the claims which follow thereafter.

Experimental Details

EXAMPLE 1

Interactive Cloning with the SH3 Domain of N-src Identifies a New Brain-specific Ion Channel Protein, with Homology to Cyclic Nucleotide-gated Channels By screening for molecules that interact with the neuronal form of Src tyrosine kinase a novel cDNA was isolated that appears to represent a new class of ion channels. The encoded polypeptide, mBCNG-1, is distantly related to proteins in the family of the cyclic nucleotide-gated channels and the voltage-gated channels, Eag and H-erg. mBCNG-1 is expressed exclusively in the brain as a glycosylated protein of approximately 132 kD. Immunohistochemical analysis indicates that mBCNG-1 is preferentially expressed in specific subsets of neurons in the neocortex, hippocampus and cerebellum, in particular pyramidal neurons and basket cells. Within individual neurons, the BCNG-1 protein is localized to either the dendrites or the axon terminals depending on the cell type.

Southern blot analysis shows that several other BCNG-related sequences are present in the mouse genome, indicating the emergence of an entirely new subfamily of ion channel coding genes. These findings suggest the existence of a novel class of ion channel, which is potentially able to modulate membrane excitability in the brain and which may respond to regulation by cyclic nucleotides.

Defining signal transduction pathways that contribute to the control of synaptic strength in the brain is an important and long-sought goal. In an effort to identify the biochemical targets of Src-family tyrosine kinases in the central nervous system, the yeast two- hybrid system was used to clone proteins that could interact with the SH3 domain of the neural specific form of Src kinase (Brugge, et al. , 1985; Martinez, et al. , 1987). As a result of this screening a new protein, BCNG-1 (Brain Cyclic Nucleotide Gated-1) was identified and isolated.

BCNG-1 has been identified and characterized as an ion channel protein and exhibits sequence homology to voltage-gated potassium channels, CNG channels, and plant inward rectifers. Southern blot analysis suggests that this is the first member of a new family of proteins. BCNG-1 is expressed exclusively in the brain and is preferentially localized to the processes of subsets of neurons in the neocortex, cerebellar cortex and hippocampus. The specific localization pattern of BCNG-1 and the potential for a direct interaction with cyclic nucleotides suggest that it may represent a new brain-specificion channel protein that is an important component in the expression of intercellular and intracellular signaling.

Results

Isolation of BCNG-1. BCNG-1, a novel cDNA with homology to CNG-related and Eag-related ion channels was initially isolated and identified by interactive cloning with the N-src SH3 domain in a yeast two-hybrid screen. The src gene expresses an alternatively spliced form (N-src or pp60$^{scr-c}$(+)), which is specific for neuronal cells and has an increased kinase activity (Brugge, et al., 1985). The N-src protein differs from the non-neuronal form (c-src or pp60$^{src-}$$_c$) by an insertion of six amino acids in the region corresponding to the Src homology 3 (SH3) domain of the protein (Martinez et al. 1987). SH3 domains are considered modules for protein-protein interaction (Pawson, et al., 1995). Therefore the yeast two-hybrid screen (Fields, et al., 1989; Zervos, et al., 1993) was used to identify brain specific proteins that would selectively interact with the N-src SH3 domain.

The screening of $5 \times 10^5$ independent clones with the N-src SH3 bait resulted in the isolation of a single positively reacting fusion product (pJG-d5). This clone encoded a protein that showed a strong interaction with the N-src SH3 domain, but no significant interaction with the c-src, fyn, or abl SH3 domains, indicating a specific recognition of the N-src SH3 domain in the yeast two-hybrid system. The sequence analysis of pJG-d5 indicated that it encodes the C-terminal portion of a larger protein. Overlapping cDNA clones were therefore isolated from a λgt10 library and an open reading frame (ORF) was identified that encodes a 910 amino acid polypeptide with a predicted molecular weight of 104 kDa (FIG. 1A). The pJG-d5 insert corresponds to its C-terminal amino acids 404–910.

Figure 1C:
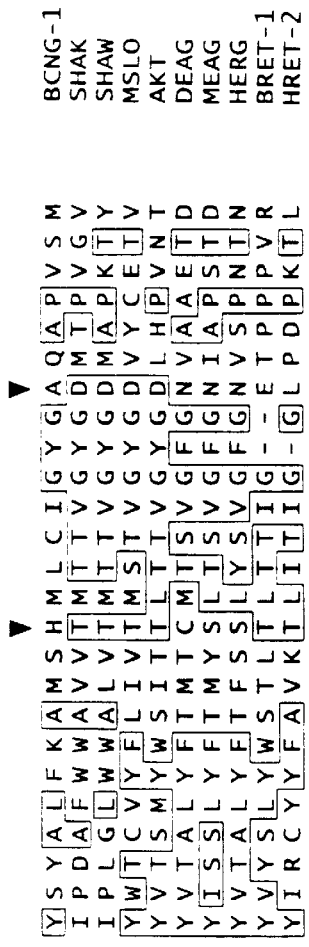
FIG. 1C: Multiple alignment of the putative P region of mBCNG-1 (SEQ ID NO:35) with the P regions of prototypical potassium channel proteins of the Shaker, plant inward rectifier and Eag subfamilies. Shown in the alignment are the P regions of Shaker (SEQ ID NO:36) (SHAK, Papazian et al., 1987; Kamb et al., 1988), and the Shaker-related channels, SHAW (SEQ ID NO:37) (Wei, et al., 1990), the calcium-activated K channel, MSLO (SEQ ID NO:38) (Pallanck and Ganetzky, 1994), the plant inward rectifier, AKT (SEQ ID NO:39) (Sentenac et al., 1992) and the Eag-related channels, Drosophila ether-a-gogo, DEAG (SEQ ID NO:40) (Warmke et al., 1991), mouse ether-a-gogo, MEAG (SEQ ID NO:41) (Warmke and Ganetzky, 1994), and the Human ether-a-gogo-related gene, HERG (SEQ ID NO:42) (Warmke and Ganetzky, 1994). Also shown are the bovine retinal α-subunit, BRET1 (SEQ ID NO:43) (Kaupp et al., 1989), and human retinal β subunit, HRET-2 (SEQ ID NO:44) (Chen et al., 1993). Arrowheads mark the residues 344 and 352 (see Example 1, page 32).
Figure 1D:
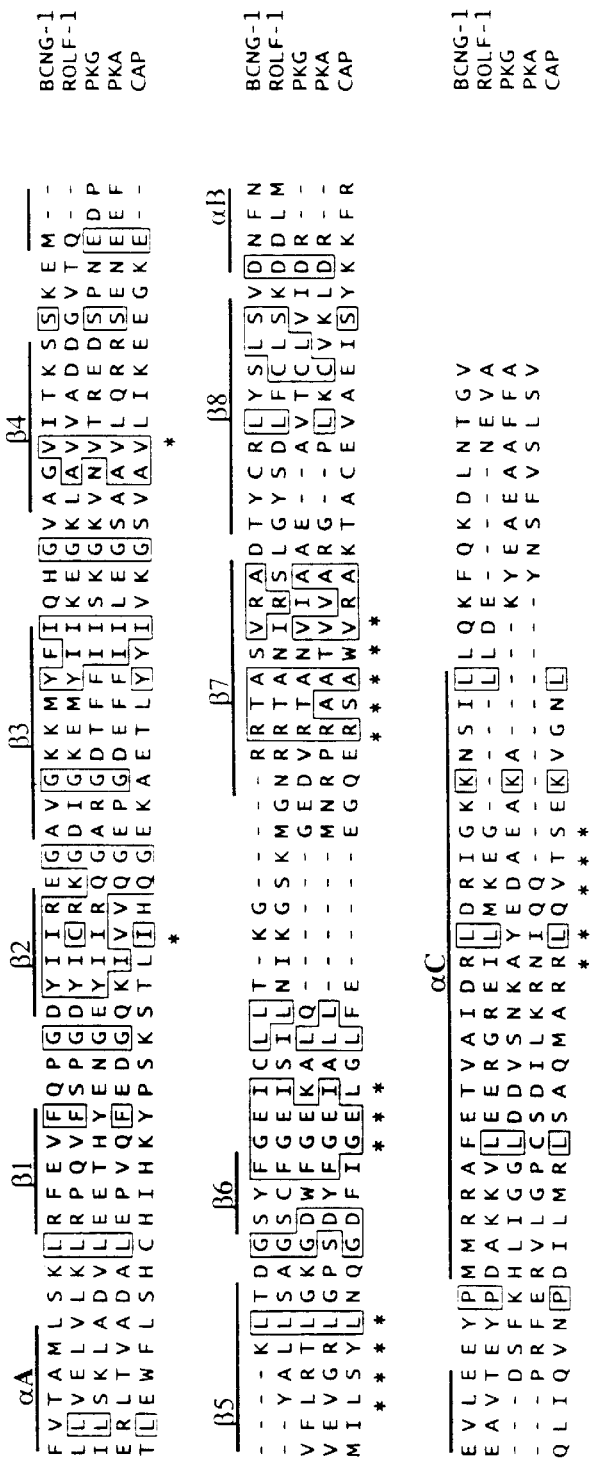
FIG. 1D: Alignment of the cyclic nucleotide binding region of mBCNG-1 (SEQ ID NO:45) with the corresponding site in the rat olfactory CNG channel (ROLF-1) (SEQ ID NO:46), the bovine cGMP-dependent protein kinase (PKG) (SEQ ID NO:47), the bovine cAMP-dependent protein kinase (PKA) (SEQ ID NO:48), and the catabolite activator protein of E.coli (CAP) (SEQ ID NO:49). Continuous lines mark α-helical (α) and β-strand (β) elements of the secondary structure elements of CAP, while asterisks indicate specific amino acids that appear to lie close to the cAMP molecule in the CAP crystal structure.

The N-terminal part of the predicted protein contains an hydrophobic core comprising seven hydrophobic domains (FIG. 1B). These domains show significant homology to the six transmembrane domains (S1–S6) and the pore region (P) of voltage activated K$^+$ channels (FIG. 1C). In addition to the hydrophobic core, there is a putative cyclic nucleotide binding site (CNBs) in the C-terminal half of the protein (amino acids 472–602, FIG. 1A and FIG. 1D). This cyclic nucleotide binding site is most closely related to the corresponding region in cyclic-nucleotide gated channels (30% similarity). The amino acids that lie close to the bound cyclic nucleotide in the bacterial catabolite gene activator protein (CAP) are conserved in the N-src interacting protein, suggesting that the CNBs is functional (Weber et al., 1989). On the basis of these features, the newly identified protein was designated BCNG-1 (Brain Cyclic Nucleotide Gated 1).

Among all the known K$^+$ channel superfamily genes, the core region of BCNG-1 displays the highest similarity (22%) to the corresponding region in the mouse Eag protein, whereas the similarity to cyclic nucleotide-gated channels is only 17% in this region (distances were determined by the MegAlign program of DNASTAR). The S4 domain of BCNG-1 has a total of eight positively charged residues (two groups of four, separated by a serine), which again makes it more similar to voltage activated K$^+$ channels (Sh and eag families) than to cyclic nucleotide-gated channels.

The putative pore forming region of the BCNG-1 protein (FIG. 1C) is also most closely related to the corresponding region in Shaker and Eag-related channels (30% similarity in either case) . However, it contains significant substitutions in two positions that are otherwise highly conserved in voltage activated K$^+$ channels: the aspartate residue which follows the GYG triplet is replaced with alanine (position 352) and the serine/threonine residue at −8 from that position is replaced with histidine (position 344). Similar substitutions are found in the P-subunit of the retinal CNG-channel, where the position corresponding to the aspartate is occupied by a leucine and a lysine is found at −8 from that position (Chen, et al., 1993). This suggests that the BCNG-1 protein might be incapable of conducting current per se, but may act in combination with a second not yet identified polypeptide to form a functional heteromultimeric ion channel.

BCNG-1 is a 132 kDa Glycoprotein. To characterize the protein encoded by the BCNG-1 cDNA, antibodies were generated against two separate domains in the predicted cytoplasmic tail: amino acids 594–720 (fusion protein GST-q1; antiserum αq1) and amino acids 777–910 (fusion protein GST-q2; antiserum αq2). Both antisera specifically immunoprecipitated the in vitro translation product of the cloned BCNG-1 sequence.

Figure 2A:
FIGS. 2A–2D. BCNG-1 is a 132 kDa glycosylated protein.
Figure 2B:
Figure 2C:
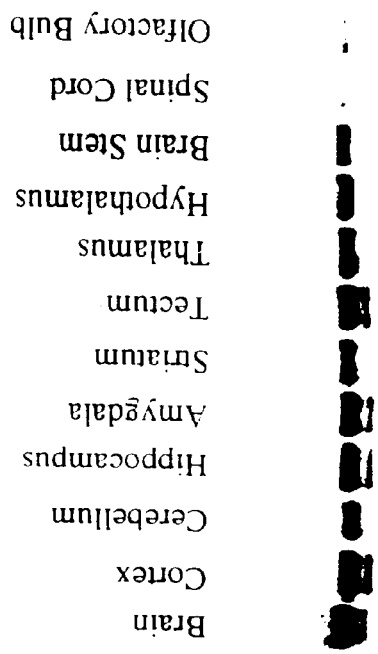
Figure 2D:
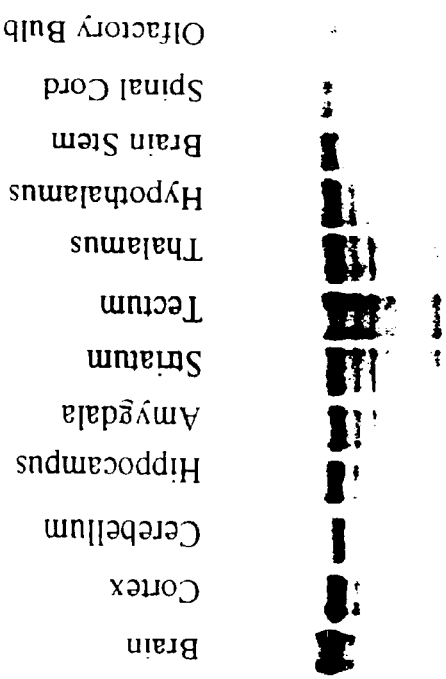

In Western blots of mouse brain extracts, both the αq1 and αq2 antisera recognized a diffuse band with an apparent molecular mass of 132 kDa (FIG. 2A). Complete abolition of the labeling by preadsorbing the antisera with a GST-fusion protein incorporating both antigenic domains (GST-d5, amino acids 404–910) indicates it represents the native BCNG-1 subunit. Treatment of the brain extract with N-glycosidase F prior to the Western blotting results in a substantial reduction of the molecular weight of the observed band, which now co-migrates with the in vitro translated BCNG-1 product (FIG. 2B).

Sequence analysis indicates that three N-glycosylation consensus sites are present in the BCNG-1 protein. Among these, Asn 327 is predicted to lie between transmembrane domain S5 and the pore (P) on the extracellular side of the plasma membrane (FIG. 1A and FIG. 1B). This site corresponds to Asn 327 of the cGMP-gated channel from bovine rod photoreceptors, where it has been demonstrated to be the sole site of glycosylation (Wohlfart et al., 1992). Together, these data suggested that the cloned cDNA sequence encodes the full length product of the BCNG-1 gene and that BCNG-1 is a N-linked glycoprotein.

Figure 3:
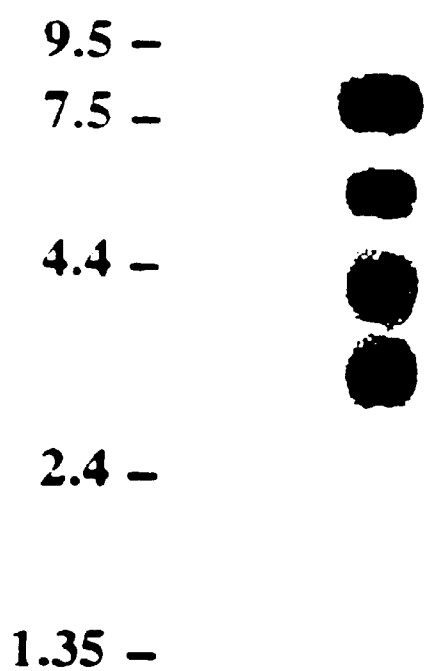
FIG. 3. Northern blot analysis of BCNG-1 expression in different mouse tissues. Two μg of poly(A)$^+$ RNA from each of each of the following tissues was used: heart (H), brain (B), spleen (S), lung (Lu), liver (Li), skeletal muscle (M), kidney (K) and testis (T) were loaded. The filter was probed with a DNA fragment encoding amino acids 6–131 of the BCNG-1 sequence. A probe corresponding to amino acids 594–720 recognized the same bands, confirming that the cDNA fragments isolated from the λgt10 and pJG4-5 libraries are from a contiguous mRNA sequence. Positions of molecular weight standards are shown on the left.

BCNG-1 is expressed in neurons. Northern blot analysis revealed the presence of multiple BCNG-1 transcripts in poly(A)$^+$ RNA from the brain, the most abundant species being 3.4, 4.4, 5.8 and 8.2 kb long (FIG. 3). The 3.4 kb transcript corresponds in size to the cloned cDNA. No expression was detected in the heart, spleen, lung, liver, skeletal muscle, kidney or testis. The specific expression of the BCNG-1 protein was confirmed by Western blot analysis.

The cellular localization of BCNG-1 within the brain was examined by in situ hybridization (FIG. 4) and by immunohistochemical staining (FIGS. 5A–5F). In both cases, the highest levels of BCNG-1 expression were detected in the cerebral cortex, in the hippocampus, and in the cerebellum.

Figure 4:
FIG. 4. In situ hybridization analysis of BCNG-1 expression in the brain. Parasagittal section of a mouse brain probed with an antisense oligonucleotide directed to the mRNA region corresponding to amino acids 648–657 of the BCNG-1 sequence. Abbreviations: nCtx, neocortex; Hp, hippocampus; Crb, cerebellum; BrSt, brainstem.

In the cerebral cortex, in situ hybridization shows a strong expression of the BCNG-1 mRNA layer V pyramidal neuron cell bodies that are distributed in a continuous line along the neocortex (FIG. 4). Immunohistochemical analysis reveals a strict subcellular localization of the BCNG-1 protein within these cells. Staining of the apical dendrites (FIG. 5A) extends into the terminal branches of these fibers and is particularly intense in layer I, which contains the terminal dendritic plexus of the pyramidal neurons (FIG. 5B).

A similar expression pattern can be recognized in the hippocampus. Here, the in situ hybridization shows a strong BCNG-1 mRNA expression in the pyramidal cell body layer of areas $CA_1$ and $CA_3$ (FIG. 4). The labeling in area $CA_3$ is somewhat less prominent than the labeling in area $CA_1$. At the protein level, the most intense BCNG-1 immunostaining is observed along the hippocampal fissure, in the layer corresponding to the stratum lacunosum-moleculare (FIG. 5C). This layer contains the terminal branches of the apical dendrites of the pyramidal neurons in area $CA_1$ (Raisman, 1965). Further BCNG-1 immunoreactivity is detected within the stratum pyramidale of areas $CA_1$ and $CA_3$; the staining, however, is absent from the pyramidal cell bodies but is rather present in the fibers surrounding them (FIG. 5D). These fibers most likely represent the basket cell plexus associated to pyramidal neurons.

Figure 5F:
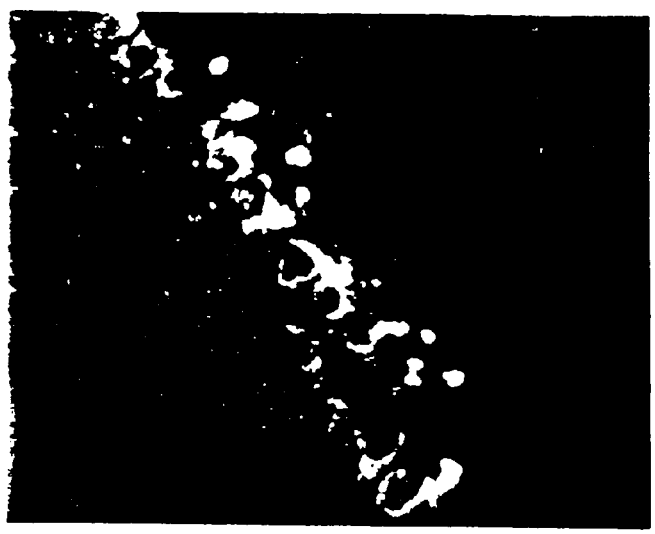
Figure 5E:

The immunostaining in the cerebellum also shows a pattern characteristic of basket cell expression. In the cerebellar cortex, basket cell nerve endings branch and contact the initial segment of the Purkinje cell axon in a distinct structure known as "pinceau" (Palay, et al., 1974). As shown in FIGS. 5E and 5F, these structures are intensely labeled by the $\alpha$q1 and $\alpha$2 antisera, while the staining excludes the Purkinje cell bodies. Thus, in basket cells, the BCNG-1 protein appears to be selectively localized to axons and is particularly enriched in the nerve terminals. An intense labeling of some brainstem nuclei is observed by in situ hybridization (FIG. 4) and areas of immunoreactivity were detected in other brain regions, including the olfactory bulb.

Figure 6A:
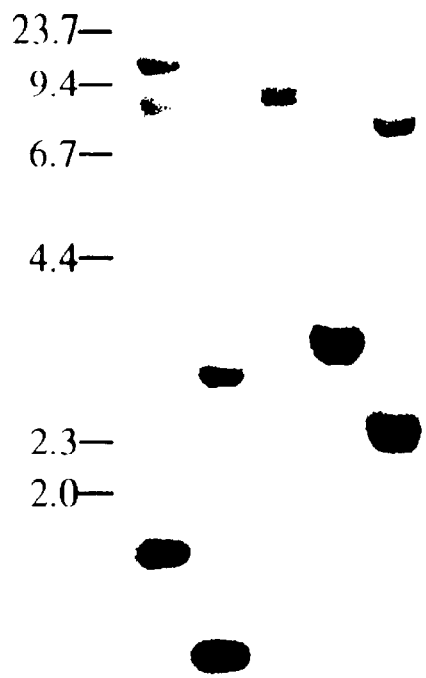
FIGS. 6A–6B. Southern blot analysis of mouse genomic DNA. 4 μg of mouse genomic DNA were loaded onto each lane following digested with Eco RI (1), Hind III (2), Bam HI (3), Pst I (4) or Bgl II (5). The filter was probed with a DNA fragment encoding amino acids 269–462 of the BCNG-1 sequence at high (FIG. 6A) and (FIG. 6B) low stringency. Positions of molecular weight standards are shown on the left.
Figure 6B:
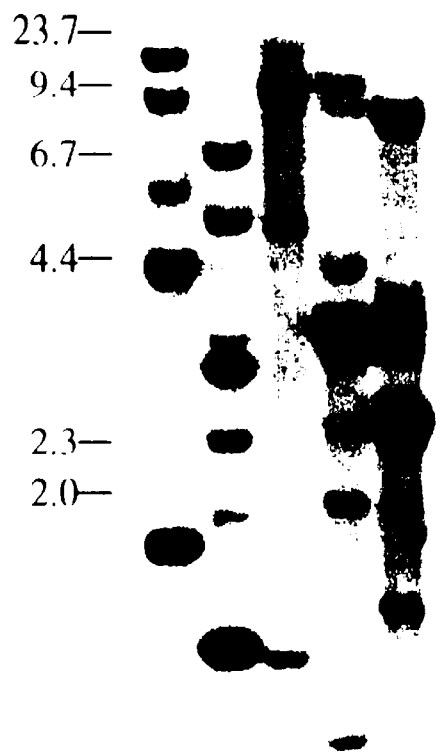

BCNG-1 defines a new subfamily of $K^+$ channel genes. Most of the ion channel sequences characterized so far are members of evolutionarily related multigene families. To investigate whether more sequences related to BCNG-1 exist, mouse genomic DNA Southern blots were analyzed under various stringency conditions (FIG. 6).

The probe (B1-T) was designed in the hydrophobic core region of BCNG-1, including transmembrane domains S5, P and S6; the repeat region in the C-terminal portion of the protein was excluded. Reducing the stringency of the hybridization conditions from 8° C. below the melting temperature of the B1-T probe (FIG. 6A) to 33° C. below the melting temperature (FIG. 6B) resulted in the detection of a number of additional hybridization signals in every lane of the blot. None of the known sequences in the $K^+$ channel superfamily has sufficient homology to BCNG-1 to hybridize under these conditions. This result suggests that BCNG-1 is the first known member of a larger group of related genes, which represent a new branch in the voltage-gated $K^+$ channel superfamily.

Discussion

Voltage-gated potassium (VGK) channels constitute a large and still expanding superfamily of related genes (Strong, et al., 1993; Warmke and Gonetzky, 1994). The most widely used strategy for cloning new genes in the VGK family has been by homology to a small number of initial members (Sh, eag, and slo from Drosophila (Papazian, et al., 1987; Kamb, et al., 1987; Warmke, et al., 1991; Atkinson, et al., 1991); cGMP-channel from bovine retina (Kaupp, et al., 1989). Unfortunately, this approach is not well suited for identifying more divergent sequences. Expression cloning in Xenopus ocytes can circumvent this problem, however, this implies a pre-existing or readily detectable physiological characterization of the channel.

An alternative cloning strategy that requires no a priori knowledge of the structure or activity of the target protein is to screen for $K^+$ channels by means of protein-protein interactions. Using the SH3 domain of N-src as a bait, a protein, mBCNG-1, was obtained that appears to constitute a new branch of the $K^+$ channel superfamily. mBCNG-1 displays the motifs of a voltage-gated $K^+$ channel (six transmembrane spanning domains, a highly basic S4, and a P region) (Strong, et al., 1993, Warmke, et al., 1994 and FIGS. 1A–1D). mBCNG-1, despite its similarity to voltage activated $K^+$ channel superfamily members, with defined by the presence of six transmembrane domains and a pore-like region (Warmke, et al., 1994), shows considerable divergence from all of the other known sequences. Although the cyclic nucleotide binding site of BCNG-1 is most similar to the site present in CNG channels (30%), the S4 and previous are most closely related to the corresponding regions in Shaker and Eag. Overall, the highest similarity in the hydrophobic core region is to mouse Eag Protein (22%). Thus, BCNG-1 appears to constitute a new branch of the $K^+$ channel superfamily.

The fusion between an ancestral $K^+$ channel and an ancestral cyclic nucleotide binding site is likely to have occurred prior to the evolutionary separation between plants and animals (Warmke, et al., 1994). Divergence from this common ancestor would have led on one hand to Eag-related channels and plant inward rectifiers (which maintained more of the features of voltage activated $K^+$ channels, while showing a progressive deviation from the original CNBs sequence) and on the other hand to CNG-channels (which show a higher evolutionary constraint on the cyclic nucleotide binding site, while they have lost voltage activation and $K^+$ selectivity). The features of BCNG-1 suggest that it may have remained closer to the ancestral molecule that represents the evolutionary link between voltage-gated $K^+$ channels and cyclic nucleotide-gated channels.

The emerging pattern for olfactory and retinal CNG-channels and the non-consensus sequence of the putative pore forming region of BCNG-1 suggests that the lack of detectable electric current following BCNG-1 expression in xenopus oocytes is due to BCNG-1 representing a β subunit of a heteromultimeric channel (Chen, et al., 1993; Liman, et al., 1994; Bradley, et al., 1994). Indeed the data show the existence of a number of BCNG-related sequences in the mouse genome, and one or more of these genes could encode additional subunits required for the formation of an active channel.

BCNG-1 protein is expressed only in the brain and in particular in two of the principal classes of neurons within the cerebral, hippocampal and cerebellar cortexes: pyramidal neurons and basket cells. This distribution would be consistent with an in vivo interaction of BCNG-1 with N-src, which is also expressed in cerebral and hippocampal pyramidal neurons (Sugrue, et al., 1990). The observed interaction between BCNG-1 and the N-src SH3 domain is intriguing as is its physiological relevance and the role of the proline-rich region. The possibility that other factors may target the proline-rich region of BCNG-1 has also to be considered, particularly in view of the recently discovered WW domains (Sudol, et al., 1996; Staub, et al., 1996).

The varied subcellular localization of BCNG-1 (dendritic in pyramidal cells and axonal in basket cells) suggests that BCNG-1 could play different roles in different populations of neurons, perhaps by regulating presynaptic or postsynaptic membrane excitability depending on the cell type. A similar distribution has been demonstrated for the K$^+$ channel subunit Kv 1.2 (Sheng, et al., 1994; Wang, et al., 1994). Kv 1.2 forms heteromultimeric K$^+$ channels with several other Shaker type subunits, which have an overlapping yet differential pattern of expression, giving rise to a range of conductances with diversified functional characteristics.

The presence of BCNG-1 in the dendrites of hippocampal pyramidal cells is particularly intriguing; cAMP has been shown to be important for the establishment of some forms of long-term synaptic potentiation in these cells (Frey, et al., 1993, Bolshakov, et al., 1997; Thomas, et al., 1996). The structural features of BCNG-1 predict a K$^+$ conducting activity, directly modulated by cyclic nucleotide binding. Interestingly, a current with similar characteristics has been described in the hippocampal pyramidal neurons of area CA$_1$ (Pedarzani, et al., 1995), where BCNG-1 is highly expressed. This current ($I_Q$) is believed to contribute to the noradrenergic modulation of hippocampal activity, by regulating neuronal excitability in response to cAMP levels. BCNG-1 could participate in the formation of the channels responsible for this type of current.

Experimental Procedures

Yeast two hybrid interaction cloning of mBCNG-1. The two-hybrid screen was performed following published procedures (Zervos, et al., 1993); the reagents used included plasmids pEG202, pJG4-5, pJK103 and *Saccharomyces cerevisiae* strain EGY48 (MATa trp1 ura3 his3 LEU2::pLexAop6-LEU2).

The bait was created by subcloning the SH3 domain of N-src in plasmid pEG202, and contains amino acids 83–147 from the mouse N-src sequence (Martinez, et al., 1987). The cDNA fusion library was constructed in plasmid pJG4-5, using poly(A)$^+$ RNA from the whole brain of an adult C57BL/6 male mouse; the cDNA was synthesized using random hexamers and the GIBCO-BRL SuperScript II synthesis kit, according to the manufacturer's instructions. Only the library constructed from the two fractions with an average cDNA size of >1.5 kb (total of 1×10$^6$ independent clones) was used in the two hybrid screen. Library amplification was done in 0.3% SeaPrep agarose (FMC) to avoid changes in complexity.

For library screening, *Saccharomyces cerevisiae* strain EGY48 was first cotransformed with the bait plasmid pEG202-Nsrc and the reporter plasmid pJK103. The resulting strain was maintained under selection for the HIS3 and URA3 markers, and subsequently transformed with the mouse brain cDNA library in plasmid pJG4-5. This description though is more accurate and should be substituted for the transformation mix was grown for two days in a Ura$^-$ His$^-$ Trp$^-$-glucose medium containing 0.3% SeaPrep agarose (FMC); the cells were then harvested and plated on Ura$^-$ His$^-$ Trp$^-$ Leu$^-$-galactose. Leu$^+$ colonies were screened for β-galactosidase activity using a filter lift assay (Breede and Nasmith, 1985). Positively reacting fusion products were isolated and tested for specificity following retransformation into an independent yeast strain. Fusion product pJGd5 corresponds to the C-terminal part of mBCNG-1 (amino acids 404–910; see FIG. 8).

Full length cloning of mBCNG-1. For the isolation of the 5' end region of the mBCNG-1 cDNA, two rounds of PCR were performed on the pJG4-5 library, using nested oligonucleotides derived from the pJG-d5 sequence. The downstream primer in the first round was: 5'-AGAGGCATAGTAGCCACCAGTTTCC-3' (Seq. ID. No.: 13)(d5.RL, corresponding to amino acids 456–463 of the mBCNG-1 sequence; see FIG. 8). The downstream primer in the second round was: 5'-CCGCTCGAGGCCTTGGTATCGGTGCTCATAG-3' (Seq. ID. No.: 14) (d5.N2), corresponding to amino acids 424–430 of mBCNG-1 and an added XhoI site). The upstream primer was either of two oligonucleotides designed in the pJG4-5 vector sequence: 5'-GAAGCGGATGTTAACGATACCAGCC-3' (Seq. ID. No.: 15) (B42), located 5' to the EcoRI site in the B42 acidic patch, or: 5'-GACAAGCCGACAACCTTGATTGGAG-3' (Seq. ID. No.: 16) (ter), located 3' to the EcoRI site in the ADH terminator.

PCR cycling was performed as follows: 1×(2 minutes, 94° C.); 25×(45 seconds, 94° C.; 30 seconds, 58° C.; 3 minutes, 72° C.); 1×(10 minutes, 72° C.).

The longest amplification product obtained from this series of reactions was a 700 bp DNA fragment, which contained amino acids 204–430 from the mBCNG-1 sequence (See FIG. 8). This fragment was subcloned, repurified and used as a probe to screen a Mouse Brain cDNA library in λgt10 (CLONTECH, cat. no. ML3000a), in high stringency conditions (hybridization overnight at 65° C. in 50% formamide, 5×SSC (1×SSC=0.15 M sodium chloride/ 0.015 sodium citrate, pH 7), 5×Denhardt's (1×Denhardt's= 0.02% Ficoll/0.02%polyvinylpyrrolidone/0.02% bovine serum albumine), 0.5% SDS, 100 mg/ml salmon sperm DNA. Washing: 10 minutes, room temperature in 2×SSC/ 0.1% SDS, followed by twice 30 min at 65° C. in 0.2×SSC/ 0.1% SDS.

Positively reacting clones were further screened by PCR, using oligonucleotide d5.RL (Seq. ID. No.: 13) as a downstream primer. The upstream primer was either of the two following vector oligonucleotides: 5'-GAGCAAGTTCAGCCTGGTTAAGTCC-3' (Seq. ID. No.: 17) (15'.N2), located 5' to the EcoRI site in the λgt10 sequence, or 5'-GTGGCTTATGAGTATTTCTTCCAGGG-3' (Seq. ID. No.: 18) (13'.N2), located 3' to the EcoRI site. PCR cycling was performed as described above.

The resulting products were subcloned and sequenced. The longest extension contained amino acids 1–463 of the mBCNG-1 sequence (See FIG. 8); the overlapping region of this insert with the insert contained in clone pJG-d5 (amino acids 405–463) includes a Bgl II site, which was used to join the 5' and 3' fragments of the mBCNG-1 cDNA in plasmid pSD64TF for expression studies.

In vitro transcription (MESSAGE MACHINE, Ambion, Austin, Tex.) and translation in vitro Express, Stratagene.

Northern/Southern Blot Hybridization

PCR-generated cDNA fragments corresponding to the indicated amino acids 6–131 (λgt10-derived) 5' sequence) and 594–720 (pJG-5 derived 3' sequence) were used to probe a Multiple Tissue Northern Blot (CLONTECH, 7762-1).

For Southern blots, a Mouse Geno-Blot (CLONTECH, 7650-1) was probed using a PCR generated cDNA fragment (B1-T) corresponding to amino acids 270–463 of the BCNG-1 sequence, as described (Sambrook, 1989). Blots were hybridized at 65° (5× standard saline citrate 1×SSC= 0.15M sodium chloride/0.015 M sodium citrate, pH7 buffer in aqueous solution) and washed as described in figure legends. Washings conditions were as indicated. The melting temperature (TM) for the B1-T probe was calculated according to the formula Tm=81.5° C.+16.6 (logM)+0.41 (%GC)– (675/L), where M is the cation concentration and L is the probe length in base pairs.

Antibody production, extracts and Immunochemistry and in situ hybridization. The Glutathione S-transferanse (GST)-fusion proteins were created by subcloning the q1

(corresponding to amino acids 594–720 of the mBCNG-1 protein) or q2 (corresponding to amino acids 777–910 of the mBCNG-1 protein) (see FIG. 1A) in plasmid pGEX-lombole (Pharmacia), followed by induction and purification of essentially as described (Frangioni and Neel, 1993). Fusion proteins were eluted in phosphate buffered saline (PBS) and injected into rabbits as a 1:1 suspension with Freund adjuvant (Pierce). Antisera were prepared and tested essentially as described (Grant, et al., 1995).

For Western Blot analysis, mouse brain extracts were separated on a 10% SDS-PAGE and electroblottted to PVDF membranes (Immobilon-P, Millipore) as described (Grant, 1995). Blocking and antibody incubations were done in TBST (10 mM Tris pH 7.5, 150 mM NaCl, 0.1% Tween-20)+2% BSA. The αq1 and αq2 antisera were used at a 1:1000 dilution. Secondary anti-rabbit antibodies coupled to alkaline phosphatase (Bio-Rad) were used at a 1:5000 dilution, and the bands were visualized by incubation in NBT\BCIP (Boehringer Mannheim). Total brain extracts were prepared as described (Grant, 1995). For N-glycosidase treatment, 2% SDS was added to the extract and the proteins denatured by boiling for 10 min; reactions were carried out in 50 mM NaP (pH 7.2), 25 mM EDTA, 0.5% Triton-X100, 0.2% SDS, 1 mg/ml protein and 20 U/ml N-glycosidase F (Boehringer) for 1 hr at 37C.

For immunohistochemistry, 20 µm cryostat sections of mouse brain (fixed in 4% paraformaldehyde/PBS), quenched in 50 mM NH4Cl/PBS, were blocked (10% goat serum, 0.1% goat serum, 0.1% saponin in PBS) and then exposed to αg1 or αq2 antisera (diluted 1:400 in blocking solution). After washing in PBS+0.1% saponin, sections were incubated with Cy3-conjugated goat anti-rabbit F(ab')2 fragments (Jackson Immunoreasearch Labs) diluted 1:200 in blocking solution.

In situ hybridization was performed essentially as described (Mayford et al., 1995) using oligonucleotide probes labeled by $3^1$ tailing with using$^{35}$ (S) thio-dATP and terminal transferase (Boehringer Mannheim) to a specific activity of $5\times10^8$ cpm/µg. Hybridizations were carried out at 37° C. Slides were washed at 60° C. in 0.2×SSC and exposed to film for 2 weeks.

EXAMPLE 2
Initial Cloning and Description of the Mouse BCNG Gene Family

The original sequence in the BCNG family (mBCNG-1) was isolated from a mouse brain cDNA library using yeast two-hybrid interaction cloning with the n-Src tyrosine kinase as bait as described in Example 1. The DNA and amino acid sequences of this protein are SEQ ID NO:1 and SEQ ID NO:2 respectively. Clones comprising two additional genes (mBCNG-2 and mBCNG-3) have been isolated. The DNA and amino acid sequences of mBCNG-2 are SEQ ID NO:3 and SEQ ID NO:4, respectively. The DNA and amino acid sequences of mBCNG-3 are SEQ ID NO:5 and SEQ ID NO:6, respectively. A more detailed description of the methods used to identify the sequences reported here is given in the methods section below.

All of the identified sequences contain the motifs of a voltage gated potassium channel (six transmembrane spanning domains, including a highly basic S4 domain, and a pore region) as well as a distinct cyclic nucleotide binding site (see FIG. 8). The three mouse proteins are closely related to each other, having a similarity of 84–88%, but are very distantly related to all other known members of the potassium channel superfamily, including Eag-related channels (22% similarity) and cyclic nucleotide-gated channels (17% similarity).

Northern blot analysis showed individual patterns of tissue distribution for each of these clones (see FIG. 9). The expression of mBCNG-1 appears to be restricted to the brain, whereas mBCNG-2 and mBCNG-3 are expressed in the brain as well as in the heart. Hybridization signals for mBCNG-3 are also detected in polyA$^+$ RNA from skeletal muscle and lung.

The distinct sequences and tissue distributions of these clones reveals that the BCNG clones represent a family of ion channel proteins, with characteristic voltage sensing and cyclic nucleotide binding motifs, that are predominantly located in heart and brain.

Figure 7A:
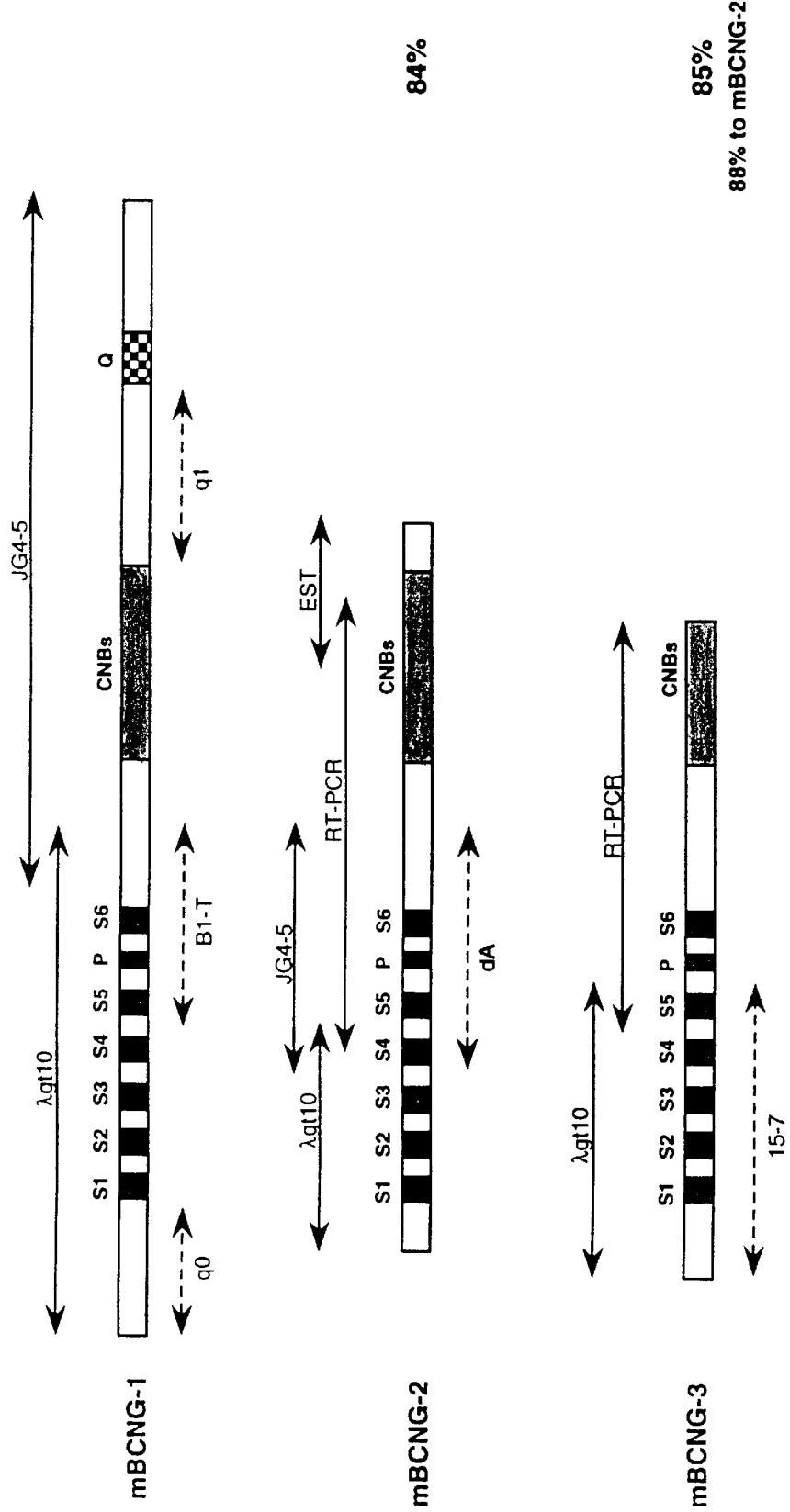
FIGS. 7A–7B: Schematic of the predicted structure of mBCNG-1 (SEQ ID NO:2) showing the six transmembrane regions (S1–S6), the pore region (P), the cyclic nucleotide binding site and the long C-terminal tail including a polyglutamine stretch (Q). Similar schematics of the proteins predicted to be encoded by the partial fragments of the other BCNG genes are also shown (SEQ ID NOS: 4, 6, 8, 10 and 12). Double headed arrows above the sequences indicate whether the fragment was obtained from a cDNA library (λgt10 or pJG4-5), an RT-PCR reaction, or an EST database. Double-headed dashed arrows underneath the sequences indicate the positions of the probes used. On the right, the percent amino acid identity to the mBCNG-1 protein is indicated (and mBNCG-2 (SEQ ID NO:4) where indicated). The alignments were performed by comparing only the core region of the proteins, including transmembrane domains S1–S6, corresponding to amino acids 111–419 (numbering according to mBCNG-1). The mBCNG-4 sequence (SEQ ID NO:8) was not included in this alignment (ND, not determined). However, limited alignment of the available cyclic nucleotide binding domain sequence (amino acids 529–592, number according to mBCNG-1) shows a 79% similarity to mBCNG-1. Hashed box near mBCNG-4 sequence indicates position of probable intron found in the M28-EST clone.
Figure 7B:
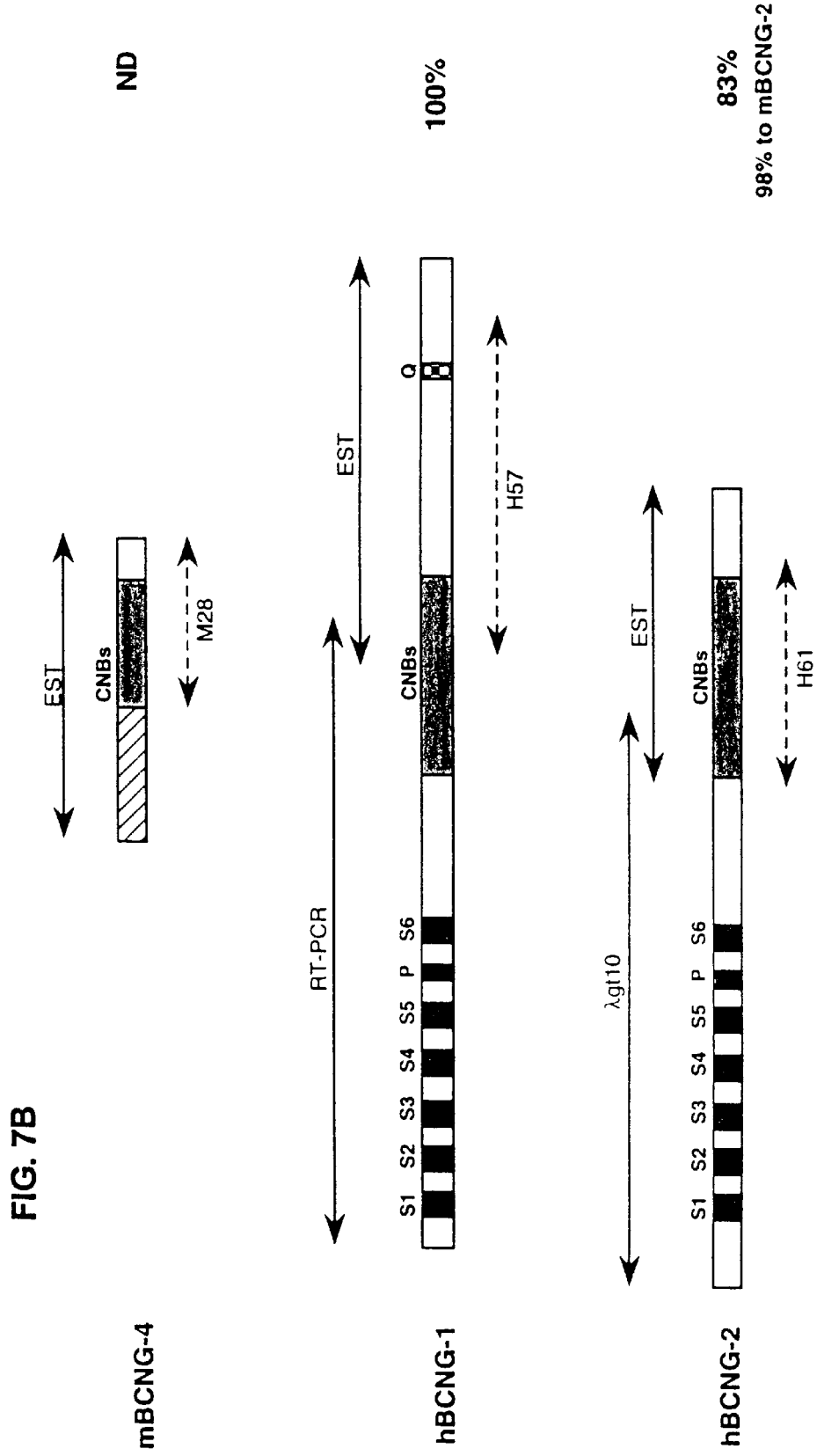
Figure 10A:
FIGS. 10A–10B. Northern blot analysis of human BCNG genes. A Multiple Tissue Northern blot, containing 2 mg of polyA+ RNA from each of the following human tissues: heart (He), brain (Br), placenta (Pl), lung (Lu) liver (Li), skeletal muscle (Mu), kidney (Ki) and pancreas (Pa), was hybridized to DNA fragments corresponding to the indicated BCNG genes. The same fragments were used to probe a human Brain Multiple Tissue blot, containing 2 mg of polyA+ RNA from each of the following tissues: amygdala (Am), caudate nucleus (Cn), corpus callosum (CC), hippocampus (Hi), total brain (Br), substantia nigra (SN), subthalamic nucleus (Sn) and thalamus (Th). Molecular size markers are indicated on the left.
Figure 10B:
Figure 10C:
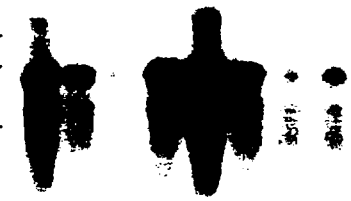
Figure 10D:
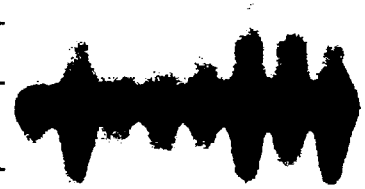

Utilization of the EST data base in subsequent cloning of mouse and human BCNG genes. To assist in the complete cloning of the mouse genes and to begin the search for the human homologues of the BCNG genes, the EST data base was searched using the sequence of the mBCNG-1 protein. This search revealed four EST clones that appear to be fragments of two mouse BCNG genes (M41, M28) and two human BCNG genes (H57, H61). Correspondence between these ESTs and the BCNG gene family is shown schematically in FIG. 7 and is indicated in Table I. Clones were obtained from the IMAGE consortium. The clones were used in the following way.

M41-EST This sequence appeared to represent a 3' region fragment of a BCNG-like gene, overlapping the cyclic nucleotide binding site. An oligonucleotide was designed corresponding to the M41 sequence and was used in an RT-PCR reaction together with an oligonucleotide designed in a conserved region of the 5' portion of the BCNG clones (oligo B123(Seq. ID. No.: 23)). A product of the expected size was obtained, both from mouse brain and heart polyA$^+$ RNA, subcloned and sequenced. An overlap in the 5' end region of M41-EST and in the 3' end region of the partial clone of mBCNG-2 indicated that M41-EST represents the 3' end region of mBCNG-2. Accordingly, this clone is valuable to acquire the 3' end region of the gene for mBCNG-2.

TABLE I

EST CLONES IDENTIFIED BY HOMOLOGY TO mBCNG-1.

| Trivial Name | Probable Identity | GeneBank Accession number | IMAGE consortium cDNA ID | Genome systems ID |
| --- | --- | --- | --- | --- |
| M41-EST | 3' of mBCNG-2 | AA023393 | 456380 | |
| M28-EST | 3' of mBCNG-4 | AA238712 | 693959 | cd-22017 |
| H61-EST | 3' of hBCNG-2 | N72770 | 289005 | |
| H57-EST | 3' of hBCNG-1 | H45591 | 176364 | |

Table I list the trivial names (designated herein), the probable correspondence between these ESTs and the BCNG genes, the GeneBank accession numbers and the clone identification numbers used by the I.M.A.G.E. consortium and Genome systems for these clones.

M28-EST. This clone also appears to contain a fragment of a BCNG-like gene, including the 3' end region of the cyclic nucleotide binding site. An oligonucleotide to the M28 sequence was designed and used in an RT-PCR reaction together with the B123 oligonucleotide (Seq ID. No.: 23). Again, a product of the expected size was obtained both from mouse brain and heart polyA$^+$ RNA, subcloned and sequenced. This product appeared to represent an extension of mBCNG-3.

However, no overlap was present with the M28-EST sequence, leading to the conclusion that M28 represents yet another BCNG-like gene, which we designated BCNG-4. Indeed Northern blot analysis revealed a distinct pattern of tissue distribution for BCNG-4 (see FIG. 9), which appears to be mainly expressed in the liver.

Complete sequencing of the M28-EST clone reveals that only the 3' end region of the clone aligns with the BCNG sequences; the sequence 5' to position 632 is likely to represent an intron (see SEQ. ID. NO:7 and SEQ. ID. NO:8, respectively).

H57-EST. Homology between H57-EST and mBCNG-1 suggested that this EST most likely represented the 3' end region of hBCNG-1. The validity of this identification was strengthened by Northern blot analysis. FIG. 10 shows that a probe constructed by PCR within the H57-EST sequence (see FIG. 7 for probe details) recognized four transcripts in brain polyA$^+$ RNA from a Human Multiple Tissue Blot. This pattern is very similar to that seen in the Northern blot of mBCNG-1 (see FIG. 9).

Based on this assignment, an oligonucleotide was generated corresponding to a sequence in the 5' end region of mBCNG-1 and a second oligonucleotide was designed within the H57-EST. Amplification yielded a single, strong RT-PCR product of the predicted length from human brain POLYA+ RNA. Complete sequencing of the original EST clone and of the reverse transcriptase-PCR (RT-PCR) product together yielded 2247 bp of the hBCNG-1 sequence (SEQ ID NO:9). The amino acid sequence is shown in SEQ ID NO:10. The core region of the hBCNG-1 protein exhibits 100% similarity to mBCNG-1.

H61-EST. This sequence showed marked sequence similarity to mBCNG-2 and may represent the human homologue of the mBCNG-2 protein. Northern blot analysis using a probe based on H61-EST (see FIG. 7) against a Human Multiple Tissue Blot (FIG. 10) showed indeed an expression pattern which is highly consistent with H61-EST being a 3' region fragment of hBCNG-2.

Accordingly, a sequence within the H61-EST was used to probe a human brain λgt10 cDNA library. Positive clones obtained from this screening were sequenced and shown to encode the human homologue of the mBCNG-2 protein. Together the sequences of the H61-EST and of the λgt10 clones yielded 1792 bp of the hBCNG-2 sequence (SEQ. ID NO:11:). The amino acid sequence is shown as SEQ. ID NO:12. The core region of the hBCNG-2 protein is 98% homologous to mBCNG-2.

Functional expression studies of mouse and human BCNG gene family members. Because the BCNG genes appear to encode an ion channel, mBCNG-1 was injected into in Xenopus oocytes as cRNA in order to record currents, using both two electrode voltage clamp and excised inside-out patch clamp approaches. A failure to detect current may result from a failure of correct trafficking or proper post-translational modification. In order to overcome such possible problems and to obtain functional expression of mBCNG-1, two approaches may be utilized. Firstly, expression of mBCNG-1 in a human cell line (HEK293 cells) and/or insect cell line (SF9 cells) may provide the proper post-translational modification. Second, expression in an insect cell system with a more efficient production of mBCNG-1 may yield a functional ion channel. It is also possible that mBCNG-1 can not form a functional protein alone and that it requires additional subunits. Thus, co-expression of other members of the BCNG family may circumvent this problem. Other members will be expressed individually and in combination as they are cloned.

An alternative approach is to use other ion channel subunits that are known to form heteromultimeric complexes and to co-express these with each of the BCNG subunits proteins. An important guide to this approach is to establish first which proteins exhibit overlapping tissue distribution with the BCNG proteins as determined from both Northern blot analysis (such as those in FIGS. 9 and 10) and immunochemical approaches as described herein.

Cloning of mBCNG-2. From the nested PCR reactions performed on the pJG4-5 library (see Example 1, Full-length cloning of mBCNG-1) an amplification product was isolated, that had a sequence similar but not identical to the expected mBCNG-1 sequence. It was thus inferred that it represented a different gene, closely related to mBCNG-1, which we called mBCNG-2. The identified fragment encoded amino acids 234–430 from the mBCNG-2 sequence (numbering according to mBCNG-1, see FIG. 8)

Next performed was a series of RT-PCR reactions on polyA$^+$ RNA derived from mouse brain and heart, using oligos: 5'-TGGGAAGAGATATTCCACATGACC-3' (Seq. ID. No.: 19) (7.SEQ1, corresponding to amino acids 270–277 of the mBCNG-1 sequence; see FIG. 8) as an upstream primer, and oligo d5.RL (Seq. ID. No.: 13) as a downstream primer. A 600 bp product was obtained from heart polyA$^+$ RNA, subcloned, sequenced and shown to be identical to mBCNG-2. PCR cycling: 1×(2 minutes, 94° C.); 25×(50 seconds, 94° C.; 40 seconds, 52° C.; 1.5 minute, 72° C.); 1×(10 minutes, 72° C.).

The Clontech Mouse Brain λgt10 library was screened at high stringency (see Example 1, Full-length cloning of mBCNG-1), with a PCR probe derived from the mBCNG-2 sequence (probe "dA") using oligos: 5'-TACGACCTGGCAAGTGCAGTGATGCGC-3' (Seq. ID. No.: 20) (ASEQ2, corresponding to amino acids 278–286 of the mBCNG-2 sequence, numbering according to mBCNG-1; see FIG. 8) as an upstream primer, and 5'-AGTTCACAATCTCCTCACGCAGTGGCCC-3' (Seq. ID. No.: 21) (HRL.2, corresponding to aa 444–452 of the mBCNG-2 sequence, numbering according to mBCNG-1; see FIG. 8) as a downstream primer.

Positively reacting clones were further screened by PCR, using oligonucleotide: 5'-CTGGTGGATATATCGGATGAGCCG-3' (Seq. ID. No.: 22) (B2-ASE, corresponding to amino acids 262–269 of the mBCNG-2 sequence, numbering according to mBCNG-1; see FIG. 8) as a downstream primer and either of the two lambda derived oligonucleotides (15' .N2 (Seq. ID. No.: 17) or 13'.N2 (Seq. ID. No.: 18)) as an upstream primer (see example 1 Full length cloning of mBCNG-1). The clones yielding the longest extension products were subcloned and sequenced, thus obtaining the N-terminal part of the mBCNG-2 sequence up to amino acids 304 (numbering according to mBCNG-1; see FIG. 8).

After obtaining the sequence for EST-M41, a further round of RT-PCR reactions was performed both on mouse brain and heart polyA$^+$ RNA, using oligonucleotides: 5'-CAGTGGGAAGAGATTTTCCACATGACC-3' (Seq. ID. No.: 23) (B123, corresponding to aa 269–277 of the BCNG sequences, numbering according to mBCNG-1; see FIG. 8) as an upstream primer, and 5'-GATCATGCTGAACCTTGTGCAGCAAG-3' (Seq. ID. No.: 24) (41REV, corresponding to aa 590–598 of the mBCNG-2 sequence, numbering according to mBCNG-1; see FIG. 8) as a downstream primer. Extension products of the expected length were obtained from both RNA preparations, subcloned and sequenced, linking the λgt10 derived 5' fragment and the EST derived 3' fragment of mBCNG-2.

PCR cycling was performed as follows: 1×(2 minutes, 94° C.); 25×(45 seconds, 94° C., 30 seconds, 55° C.); 2 minutes, 72° C.); 1×(10 min, 72° C.).

Cloning of mBCNG-3

From the λgt10 library screen for mBCNG-2 (see above) one positively reacting clone was obtained (#15) which appeared to give a consistently weaker hybridization signal. This insert was amplified with oligonucleotides 15.N2 (Seq. ID. No.: 17) and 13.N2 (Seq. ID. No.: 18), subcloned, sequenced and shown to represent a third BCNG-related sequence, different both from mBCNG-1 and mBCNG-2, which was called mBCNG-3. The identified fragment encoded the N-terminal part of the mBCNG-3 sequence up to aa 319 (numbering according to mBCNG-1; see FIG. 8).

After obtaining the sequence for EST-M28, an RT-PCR was performed both on mouse brain and heart polyA$^+$ RNA using oligonucleotide B123 as an upstream primer, and degenerate oligonucleotide: 5'-CACCKCRTTGAAGTGGTCCACGCT-3' (Seq. ID. No.: 25) (28REV, corresponding to amino acids 554–561 of the BCNG sequences, numbering according to mBCNG-1; see FIG. 8) as a downstream primer. Extension products of the expected length were obtained from both RNA preparations, subcloned and sequenced. Both represented extension of the mBCNG-3 sequence, as determined by an overlap with the known 3' end of the λgt10 #15 clone. PCR cycling was performed at: 1×(2 minutes, 94° C.); 25×(45 seconds, 94° C., 30 seconds, 55° C., 2 minutes, 72° C.); 1×(10 minutes, 72 ° C.).

Cloning of hBCNG-1. After obtaining the sequence for EST-H57, an RT-PCR reaction was performed on human brain polyA$^+$ RNA, using oligonucleotides: 5'-ATGTTCGGSAGCCAGAAGGCGGTGGAG-3' (Seq. ID. No.: 26) (MB1-3, corresponding to aa 102–110 of the BCNG sequences, numbering according to mBCNG-1; see FIG. 8) as an upstream primer, and 5'-CAGCTCGAACACTGGCAGTACGAC-3' (Seq. ID. No.: 27) (H57.C, corresponding to amino acids 537–544 of the hBCNG-1 sequence, numbering according to mBCNG-1; see FIG. 8) as a downstream primer. A single extension product of the expected length was obtained, subcloned, sequenced, and shown to represent the 5' extension of the hBCNG-1 clone.

PCR was performed as follows: 1×(2 minutes, 94 ° C.); 25×(45 seconds, 94° C., 20 seconds, 58° C., 3 minutes, 72° C.); 1×(10 minute, 72° C.).

Cloning of hBCNG-2. After obtaining the sequence for EST-H61, a PCR probe was made using oligonucleotides: 5' AACTTCAACTGCCGGAAGCTGGTG3' (Seq. ID. No.: 28) (H61.A, corresponding to amino acids 452–459 of the hBCNG-2 sequence, numbering according to mBCNG-1; see FIG. 8) as an upstream primer, and 5' GAAAAAGCCCACGCGCTGACCCAG3' (Seq. ID. No.: 29) (H61.F, corresponding to aa 627–634 of the hBCNG-2 sequence, numbering according to mBCNG-1; see FIG. 8) as a downstream primer on the EST-H61 DNA. This fragment was used to screen a Human Brain Hippocampus cDNA library in λgt10 (CLONTECH, cat. no. HL 3023a), in high stringency conditions (see above). Positively reacting clones were further screened by PCR, using oligonucleotide: 5' CACCAGCTTCCGGCAGTTGAAGTTG3' (Seq. ID. No.: 30) (H61.C, corresponding to amino acids 452–459 of the hBCNG-2 sequence, numbering according to mBCNG-1; see FIG. 8) as a downstream primer and either of oligonucleotides 15' .N2 (Seq. ID. No.: 17) or 131.N2 (Seq. ID. No.: 18) as an upstream primer. The clones yielding the longest amplification products were subcloned and sequenced, thus obtaining the N-terminal region of the hBCNG-2 sequence up to aa 587 (numbering according to mBCNG-1; see FIG. 8).

Northern blots. For mouse gene expression studies, a Mouse Multiple Tissue Northern Blot (CLONTECH, cat. no. 7762-1) was probed with the following PCR products: For mBCNG-1, probe "q0", obtained using oligos q0.5' (5' GCGAATTCAAACCCAACTCCGCGTCCAA3') (Seq. ID. No.: 31) and q0.3' (5' CCTGAATTCACTGTACGGATGGAT3') (Seq. ID. No.: 32). Amplification product corresponding to aa 6–131 of the mBCNG-1 sequence (see FIG. 7 and FIG. 8). For mBCNG-2, probe "dA", obtained using oligos ASEQ2/HRL.2 (see above). For mBCNG-3, probe "15-7", obtained using oligos 15.N2/13.N2 (see above); amplification performed directly on lambda phage DNA (clone #15). For mBCNG-4, probe "M28" was obtained as a gel-purified EcoRI/BglII restriction fragment (400 bp) from the EST-M28 DNA. Fragment corresponding to amino acids 529–607 of the mBCNG-4 sequence (numbering according to mBCNG-1; see FIG. 8), plus 180 nucleotides of the mBCNG-4 3' UTR (untranslated region; see Seq. ID. No.: 11).

For human gene expression studies, a Human Multiple Tissue Northern Blot (CLONTECH, cat. no. 7760-1) or Human Brain Multiple Tissue Northern Blot (CLONETECH, cat. no. 7750-1) was probed with the following PCR products: For hBCNG-1, probe H57, obtained using oligos H57.A (5' GTCGTACTGCCAGTGTTCGAGCTG3')(Seq. ID. No.: 33) and H57.B (5' GGTCAGGTTGGTGTTGTGAAACGC3') (Seq. ID. No.: 34). Fragment corresponding to aa 537–800 of the hBCNG-1 sequence (numbering according to mBCNG-1; see FIG. 8). For hBCNG-2, probe "H61", obtained using oligos H61.A (Seq. ID. No.: 28) and H61.F (Seq. ID. No.: 29)(see above).

Hybridizations were all performed in ExpressHyb solution for 1 hour, 68° C., as indicated in the manufacturer's Protocol Handbook. Washing was performed as follows: 10 minutes, room temperature in 2×SSC/0.1% SDS, followed by twice 30 minutes, 65° C. in 0.2×SSC/0.1% SDS. Filters were stripped between subsequent hybridizations by boiling for 5 min in 0.5% SDS/H$_2$O. These hybridizations by conditions constitute an example of high stringency hybridization conditions.

Sequence alignments and EST database search. Alignments and distance calculations were all performed with MegAlign (DNASTAR) on the indicated peptide sequences.

The EST database search was performed with BLAST (NCBI), using the mBCNG-1 polypeptide sequence (amino acids 1–720, to avoid the glutamine repeat present in the C-terminal region of the protein) and the TBLASTN program.

Discussion

Ion channels are important targets of drugs for treatment of a variety of neurological and cardiovascular diseases. Members of the novel BCNG family of ion channels are expressed at the mRNA level in brain, cardiac muscle sketch muscle, lung, kidney and liver. From their amino acid sequence, these channels described herein are likely to have two important physiological properties that make them a priori attractive targets for drug development. First, they are members of the voltage-gated channel family and are most similar to voltage-gated K$^+$ channels. Second, they possess a cyclic nucleotide binding domain in their carboxy terminus, suggesting that they will be directly regulated by cyclic nucleotides. Based on these properties, combined with their tissue distribution and high levels of expression at the mRNA levels, these channels are likely to play important roles in controlling neuronal and cardiac electrical activity.

The regulation of these channels through drugs may as well as transport functions in lung, liver and kidney provide a unique opportunity for regulating electrical activity associated with diseases as diverse as epilepsy, cardiac arrhythmias and cystic Fibrosis. Moreover, the cyclic nucleotide binding domain of these channels provides a unique pharmacological target that could be used to develop novel, specific, cyclic nucleotide agonists or antagonists to upregulate or downregulate channel function.

Finally, these channels are attractive candidate genes for the pacemaker current that underlies spontaneous activity in the heart and various nuclei in the brain. This hypothesis is based on physiological studies which have shown that pacemaker channels are expressed in both heart and brain and have the unique property of being gated by both voltage and the direct binding of cyclic nucleotides to a cytoplasmic site on the channel—properties similar to those predicted for BCNG channels. As these pacemaker channels regulate the rhythmic beating of the heart, respiration, attention, sleep and wakefulness, they are prime targets for drug therapy. The expression of BCNG gene family members in heterologous systems, such as mammalian cell lines, facilitates rapid drug screens that could selectively identify compounds that target channel subunits encoded by BCNG genes expressed in brain or heart.

EXAMPLE 3
Physiological and Pharmacological Significance of Mouse and Human BCNG Channel Genes
Introduction The unique structural features and the tissue distribution of the predicted proteins of the BCNG gene family suggests that they may encode the pacemaker current (variously called Ih, If or Iq) of the heart and brain. Even if the BCNG gene family does not encode the pacemaker current it is likely to be a component of other—perhaps unidentified—ionic current(s) that are important in cardiac renal, hepatic and central nervous system function. Irrespective of the identity of the current(s) that the BCNG proteins contribute to, the unique structural features of the predicted BCNG proteins (the unusual ion conducting pore (P) domain, the highly conserved cyclic nucleotide binding (cnbs) site and the highly conserved and highly charged S4 voltage sensor) indicate that they will be susceptible to multiple drug intervention strategies that target the pore, the cyclic nucleotide binding site and the voltage-dependent gating apparatus.

Analysis And Predicted Structure and General Features of the BCNG Proteins. The predicted amino acid sequence of the BCNG genes reveals that they are members of the voltage-gated ion channel superfamily. Specifically, the BCNG proteins show similarities to the superfamily of channels that includes the voltage-gated $K^+$ channels (Pongs, et al., 1995) and the cyclic nucleotide-gated channels, non-selective cation channels that are permeable to Na, $K^+$ and Ca (Zagotta and Siegelbaum, 1996). As shown schematically in FIG. 11, the BCNG proteins are predicted to have six transmembrane spanning α-helices with cytoplasmic N and C termini, a highly basic fourth transmembrane domain (S4) and pore (p) region. Each of these motifs are found in the members of the voltage-gated $K^+$ family. In addition, the BCNG proteins have a well conserved cyclic nucleotide binding site in the C-terminus. Although a homologous motif is found in some of the voltage-gated $K^+$ channels, the cyclic nucleotide binding sites in those channels are not well conserved and there is little evidence that the binding sites are functional. Indeed, the cyclic nucleotide binding site of the BCNG channels is most homologous to the sites found in cyclic nucleotide gated channels which use the binding of cyclic nucleotides to drive their activation. Furthermore, while the P loops of the BCNG channels are homologous to those found in voltage activated $K^+$ channels and cyclic nucleotide gated channels, there are several non-conservative changes in the amino acid sequence that are likely to yield ion conduction properties that are unique to the BCNG channels. Thus, the BCNG channels appear distinct from all previously identified channels in a number of ways which suggests that they have distinct physiological and pharmacological properties. These similarities and dissimilarities in the sequences of the voltage-gated $K^+$ channels, cyclic nucleotide-gated channels and the BCNG channels and the predicted consequences for BCNG channel functional properties are discussed more extensively below.
Results The Hydrophobic Core. The core of BCNG channels is predicted to have six transmembrane (α-helical sequences (S1–S6) and a pore forming P loop. This assignment is homologous to a single subunit of the tetrameric $K^+$ channels (and tetrameric cyclic nucleotide-gated channels) or a single repeat in the pseudo tetrameric Na and Ca channels. This homology suggests that-the BCNG channels are members of the voltage-gated $K^+$ channel superfamily (which also includes the voltage-independent but structurally homologous cyclic nucleotide-gated channels). It is likely that the BCNG channels will be composed of four such polypeptides in a hetero or homomultimeric structure as is seen for the voltage-gated $K^+$ channels and the cyclic nucleotide-gated channels (Chen et al., 1993; Bradley et al., 1994; Liman and Back, 1994; Lin et al., 1996). However, BCNG-1 shows considerable divergence from all other known $K^+$ channel and cyclic nucleotide-gated channel sequences. As noted above, the highest homology in the hydrophobic core region is to mouse Eag (22% amino acid similarity)—a voltage-gated $K^+$ channel that has a degenerate and probably non-functional cyclic nucleotide binding site Warimke and Gancleky. Over this core region, mBCNG-1 shows 17% identity to the voltage independent cyclic nucleotide-gated channels.

In contrast, the proteins that are predicted to be encoded by the BCNG genes show high homology to each other (>80%, see Examples 1 and 2). Indeed, mouse BCNG-1 and human BCNG-1 are identical over the core region. Similarly, mBCNG-2 and hBCNG-2 are 98% identical over the core region. Thus, the BCNG family of genes appears to constitute a new branch of the $K^+$ channel superfamily which could be regulated by cyclic nucleotide binding. The presence of a Agene family with members showing such sequence conservation strongly suggests important biological function.

The S4 voltage-sensing domain. The presence of positively charged arginine and lysine residues at every third position in the fourth transmembrane helix is a signature sequence of voltage-dependent gating ( Hille, 1992; Catterall, 1992, see FIG. 12). In contrast, in the voltage-independent cyclic nucleotide-gated channels, the S4 is degenerate with some of the positively charged residues being replaced by negatively charged acidic amino acids or being out of the triad repeat frame. These changes have reduced the net positive charge in the S4 of the cyclic nucleotide-gated channels to 3–4. This introduction of negatively charged residues may underlie the reason that the cyclic nucleotide-gated channels no longer respond to voltage. However, it is also possible that voltage-sensitivity may have been lost as a result of some other structural change in the cyclic nucleotide-gated channels and the divergence in S4 structure is simply a reflection of the loss of evolutionary pressure to retain the positive charges.

The S4 of BCNG channels are most closely related to the corresponding regions in the voltage-gated K$^+$ channels Shaker and eag, albeit poorly (mBCNG-1 is 30% homologous to the S4 of Shaker and eag). Despite an interruption by the inclusion of a serine in place of an arginine in the S4 of BCNG channels, the BCNG sequence contains more positively charged residues than any other member of the voltage-gated K$^+$ channel superfamily (see FIG. 12). The S4 domain of BCNG-1 has up to nine positively charged residues (one group of five and one group of four separated by a serine in place of one other arginine), which again makes it more similar to voltage activated K$^+$ channels (Sh and eag families) than to cyclic nucleotide-gated channels. The retention of such a highly charged S4 strongly suggests that the gating of these channels are voltage-sensitive.

The cyclic nucleotide binding site. Cyclic nucleotides regulate the activity of a diverse family of proteins involved in cellular signaling. These include a transcription factor (the bacterial catabolite activating protein, CAP), the cAMP- and cGMP-dependent protein kinases (PKA and PKG) and the cyclic nucleotide-gated (CNG) ion channels involved in visual and olfactory signal transduction (Shabb and Corbin, 1992; Zagotta and Siegelbaum, 1996). Despite obvious divergence among the effector domains of these proteins, the cyclic nucleotide binding sites appear to share a common architecture. Solution of the crystal structures of CAP (Weber and Steitz, 1987) and a recombinant bovine PKA R1α subunit (Su, et al., 1995) has demonstrated that their cyclic nucleotide binding sites are formed from an α helix (A helix), an eight stranded β-roll, and two more a-helices (B and C), with the C-helix forming the back of the binding pocket. Of the approximately 120 amino acids that comprise one of these cyclic nucleotide binding sites, six are invariant in all CAP, PKA, PKG and cyclic nucleotide gated channels. Thus, it has been suggested that the invariant residues play important—and conserved—roles in the folding and/or function of the CNB sites of these diverse proteins (Shabb and Corbin, 1992; Zagotta and Siegelbaum, 1996; Weber and Steitz, 1987; Su, et al., 1995; Kumar and Weber, 1992; Scott, et al., 1996). Indeed, the crystal structure of CAP (Weber and Steitz, 1987) and the regulatory subunit of recombinant bovine R1α (Su, et al., 1995) reveals that the glycines are at turns within the β-roll while the glutamate and the arginine form bonds with the ribose-phosphate of the nucleotide.

Figure 11:
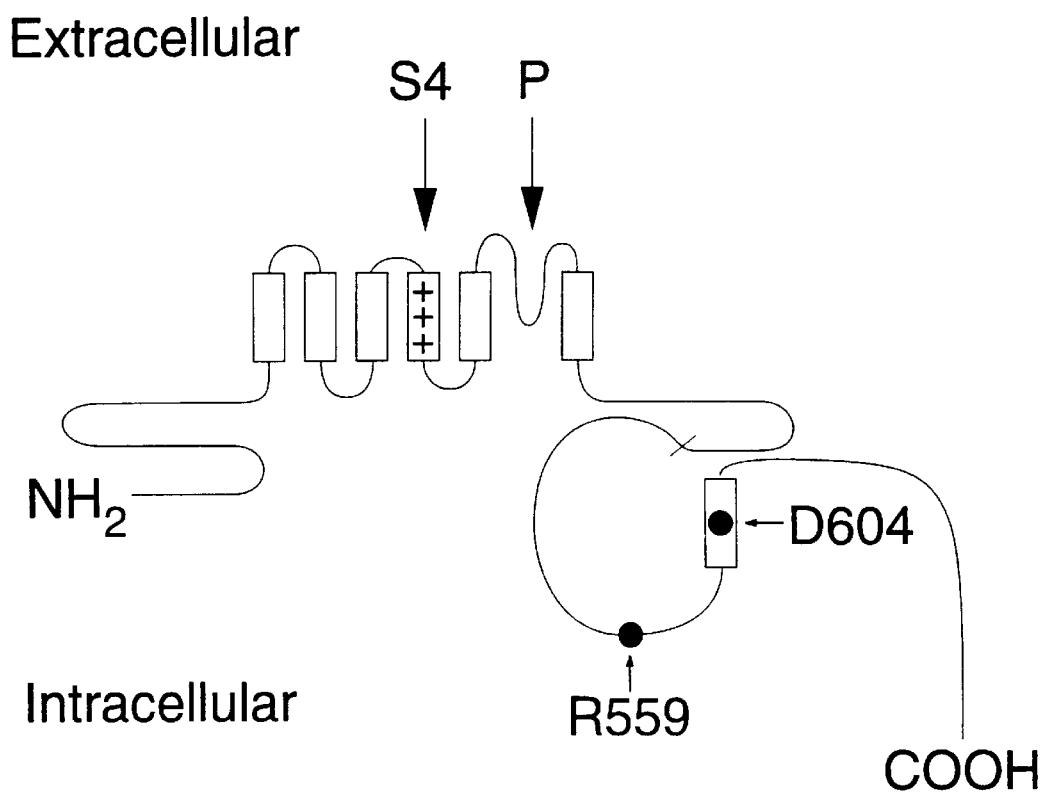
FIG. 11. Schematic representation of the general architecture of the BCNG channel proteins based on homology to the voltage-gated K+channels and the cyclic nucleotide-gated channels.

Interestingly, only three of these residues—two glycines and the arginine—appear to be conserved among the more distantly related voltage-gated channels which bear the CNB site motif but whose gating may NOT be modulated significantly by direct binding of cyclic nucleotide (KAT1 (Hoshi, 1995) and drosophila EAG (dEAG) (Bruggeman, et al., 1993) (see FIG. 11).

Thus in the plant channel, KAT1, the first glycine is mutated to an asparagine and the alanine is changed to a threonine. In dEAG the glutamate in changed to an aspartate. Furthermore, the alignment of dEAG to the highly conserved RXA sequence in β-7 is uncertain. Often, the SAA sequence within the dEAG β-7 is aligned with the RXA consensus sequence which suggests that the arginine is lost and replaced with a serine. RAL is aligned with the RXA consensus sequence which would indicate that the arginine is retained but the alanine is replaced with a leucine. Regardless of which alignment is considered, it is clear that the binding site sequence of KAT1, dEAG and related channels all show deviations from the consensus motif for a functional cyclic nucleotide binding site. In keeping with this structural divergence, there is only one report that any cloned EAG is being sensitive to direct cyclic nucleotide binding (Bruggermann et al., 1993). However, this result has not been confirmed and it is now thought to be an artifact. There is some evidence that the gating of the plant channel KAT1, may be weakly sensitive to cyclic nucleotide modulation (Hoshi, 1995).

Figure 13A:
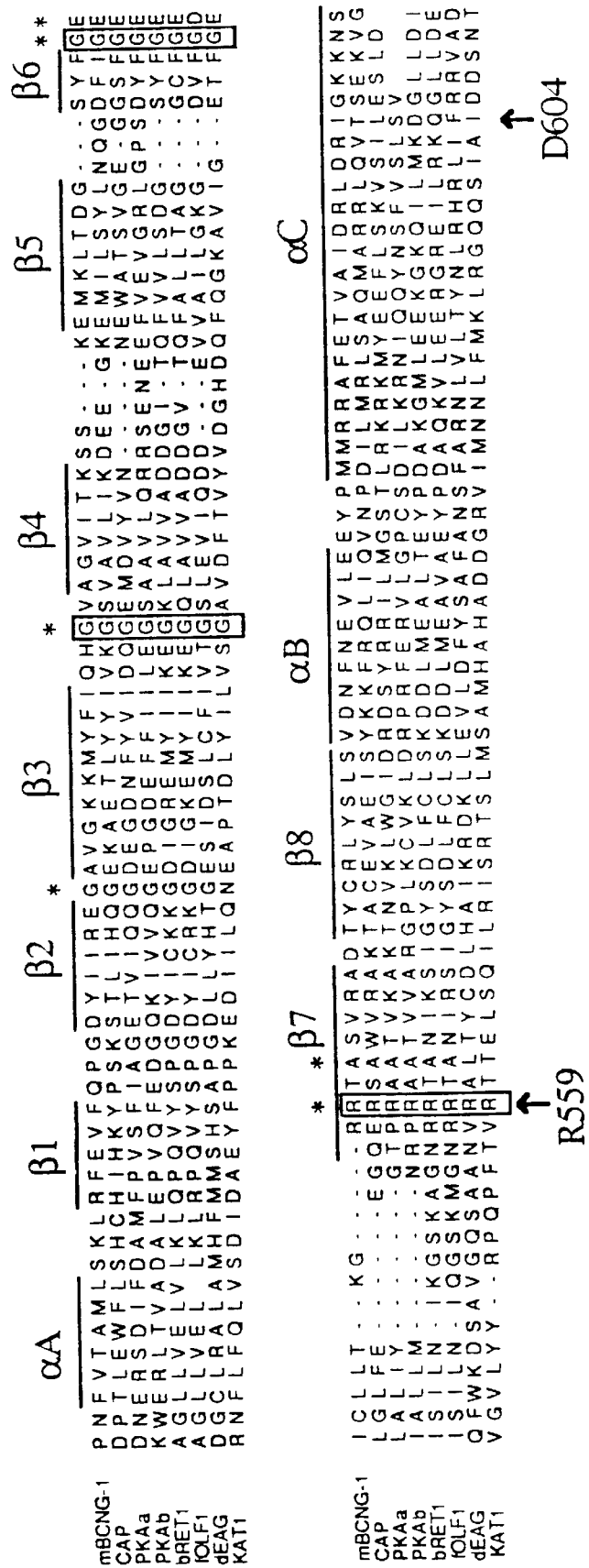
FIG. 13A: Multiple sequence alignment of the CNG region of mBCNG-1 (SEQ ID NO:53) to the functional cyclic nucleotide binding regions of catabolite activating protein (SEQ ID NO:54) (CAP, Aiba et al., 1982; Cossart & Gicquel, 1982), the A and B sites of recombinant bovine R1α (SEQ ID NO:55 and 56) (PKAα and PKAβ, Titani et al., 1984), the bovine retinal channel α subunit (SEQ ID NO:57) (bRET1, Kaupp et al., 1989) and the catfish olfactory α subunit (SEQ ID NO:58) (fOLF1, Goulding et al., 1992), the putative cyclic nucleotide binding sites of *Drosophila melangaster* Ether-a-gogo (SEQ ID NO:59) (dEAG, Warmke et al., 1991), and the *Arabidopsis thaliana* K transport protein (SEQ ID NO:60) (KAT1, Anderson et al., 1992). The six residues that are conserved across all regions whose functional competence has been unequivocally confirmed are marked by asterisks. The conserved arginine that forms an ionic bond with the cyclic nucleotide is indicated by an arrow labeled R559. The residue in the third (C) α-helix that has been shown to influence coupling of activation to cAMP versus cGMP binding is indicated by an arrow labeled D604 (the cGMP selective substitution in bRET1).
Figure 13B:
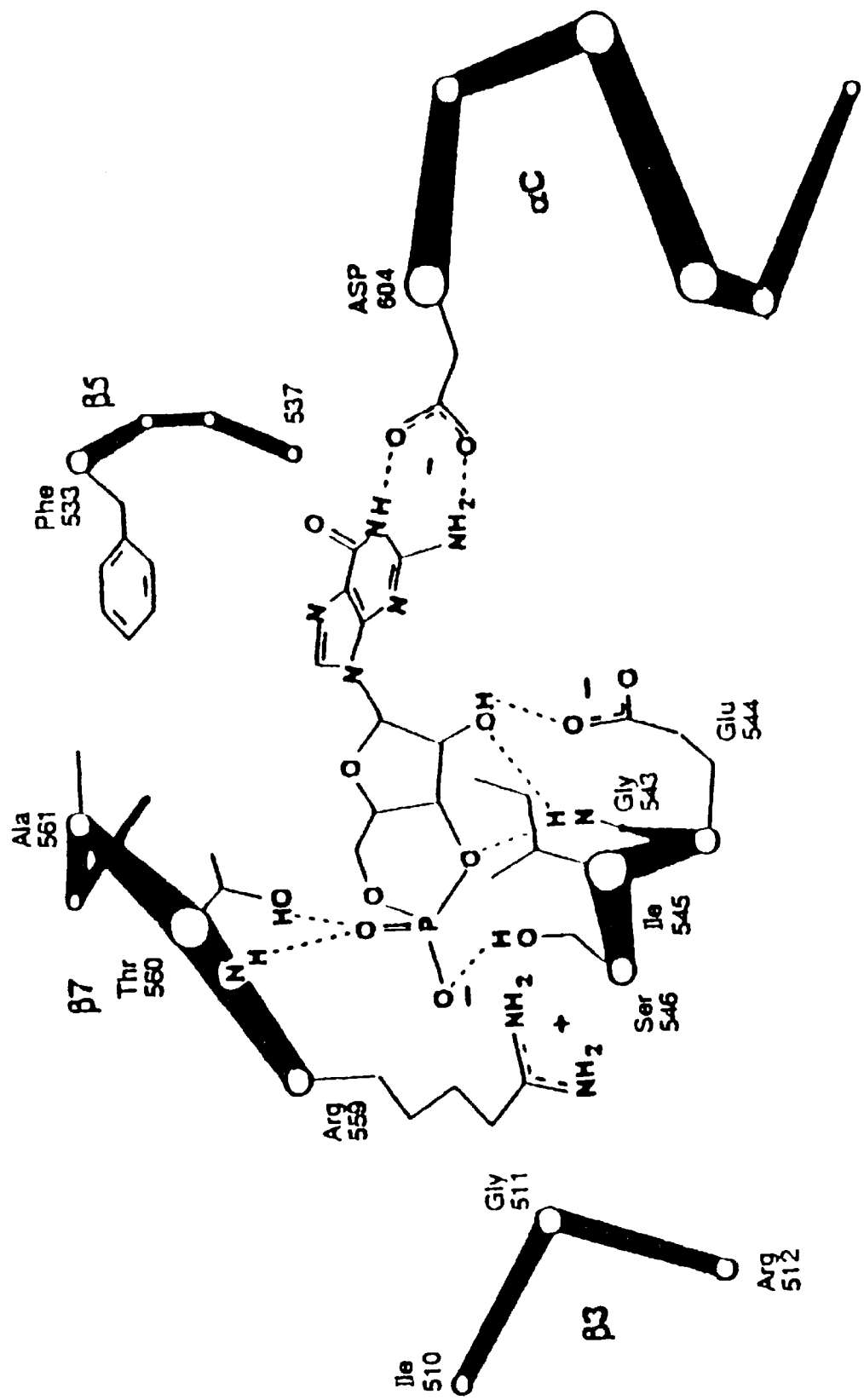
FIG. 13B: Schematic representation of the cyclic nucleotide binding site of bRET1 showing the critical interactions between the binding site and the cyclic nucleotide. This model of the binding pocket is based on the crystal structure of CAP and bovine R1α. The cGMP is shown bound in an extended, or "anti", form with the cyclicized phosphate making an ionic bond with arginine 559 (bRET1 numbering) and the purine ring forming favorable contacts with aspartate 604 in this cGMP selective channel.

FIG. 13 shows a schematic representation of the cyclic nucleotide binding site of bRET1 showing the critical interactions between the binding site and the cyclic nucleotide.

Recent evidence has demonstrated that the third (or C) α-helix moves relative to the agonist upon channel activation, forming additional favorable contacts with the purine ring. Indeed, the selective activation of bRET1 by cGMP relative to cAMP is largely determined by a residue in the C α-helix, D604 {Varnum et al., 1995}. This acidic residue is thought to form two hydrogen bonds with the hydrogens on a ring nitrogen and amino group of the cGMP purine ring. Unlike the cGMP selective bRET1 channel, cyclic nucleotide-gated channels that are activated equally well by cAMP or cGMP (fOLF1, Goulding et al., 1992; Goulding et al., 1994) or which favor activation by CAMP (rOLF2 coexpressed with rOLF1, Liman & Buck, 1994; Bradley et al., 1994) do not have an acidic residue here, but rather, have polar or hydrophobic amino acids (see Varnum, et al., 19951. Neutralization of D604 results in a loss of the ability to form the favorable hydrogen bonds with cGMP and the loss of the unfavorable interaction with the lone pair of electrons on the purine ring of cAMP, thus accounting for the channels which bear a hydrophobic or polar residue at this position becoming non-selective between cAMP and cGMP or even selective for cAMP.

In the C-terminus of the BCNG proteins there is a sequence of approximately 120 amino acids that is homologous to these cyclic nucleotide binding sites. Strikingly, the six residues that have been shown to be totally conserved in all functional cyclic nucleotide binding sites are conserved in all of the BCNG proteins that we have identified so far. The cyclic nucleotide binding site of the BCNG channels are most similar to the functional site present in the voltage-independent cyclic nucleotide-gated channels (30%). When the cyclic nucleotide binding sites found in channel genes are compared to those in protein kinases, the BCNG channel sites are more similar (25% similarity to yeast cAMP-dependent protein kinases) than those of any other ion channel. These data strongly suggest that the BCNG genes encode proteins whose activity is modulated by direct binding of cyclic nucleotide. Furthermore, the BCNG channels all have an isoleucine residue in the position where D604 is found in the cGMP selective bRETI channel. Thus, the BCNG are probably cAMP selective.

The pore. Despite the functional divergence that has given rise to Na, Ca or K selective families and to the presence of channels within these families whose conductances vary by 1–2 orders of magnitude, the pores of all members of the voltage-gated superfamily are related ( see Itillic 1992; For example see FIG. 14). Much is known about the residues that contribute to the ion permeation properties of channels and this allows predictions about the permeation properties of the BCNG proteins (Mackinnon, 1991; Heginbothem et al., 1994).

Overall, the P region of mBCNG-1 is most closely related to the corresponding region in the K selective Shaker and eag channels, albeit poorly (30%). Based on the presence of a GYG motif in the P loop, the BCNG proteins would be expected to be K selective. However, the BCNG P loops contain substitutions in several positions that are otherwise highly conserved in other voltage activated K+ channels. These changes can be seen in FIG. 14 (which shows an alignment of mBCNG-1 against channels from all the other major K channel families) and FIG. 8 (which shows the alignment of all currently cloned BCNG sequences). The aspartate residue which follows the GYG triplet is replaced with alanine (position 352) in mouse and human BCNG-1 and by an arginine in the other BCNG channels identified so far. The serine/threonine residue 8 residues N-terminal from that position (residue 344 in mBCNG-1) is replaced with histidine in all of the BCNG sequences. 6 residues N-terminal from the aspartate a hydrophobic leucine residue is introduced in place of a polar residue. In addition, at position −12 from the aspartate, a site that is occupied by an aromatic residue in all of the other channels aligned in FIG. 14, a lysine residue is introduced in all of the BCNG sequences (FIG. 8 and FIG. 14).

Interestingly, some of the substitutions found in the BCNG channels are similar to those found in the β-subunit of the CNG-channel (see hRET-2 in FIG. 14). In hRET-2, the position corresponding to the aspartate is occupied by a leucine, while a lysine is found at −8 from that position and an isoleucine is found at position −6 (Chen et al., 1993). This observation suggests that the BCNG proteins cloned so far might be the β-subunits of the BCNG channel family and the α-subunits have yet to be identified. Indeed, a failure to observe an ionic current with homomerically expressed mBCNG-1 is reminiscent of the cyclic nucleotide gated family β-subunits {Liman & Buck, 1994; Bradley et al., 1994} and the γ-subunits of the voltage-gated Shal K channel {Jegla & Salkoff, 1997}. When first cloned, the cyclic nucleotide-gated channel β-subunits were thought to be incapable of forming functional channels in the absence of the homologous α-subunits and that their normal physiological role was to generate a greater diversity of channel phenotypes by heteromeric assembly with the α-subunits. While it is clear that both the cyclic nucleotide-gated family β-subunits and the voltage-gated K channel γ-subunits can form heteromultimers with their respective α-subunits, it has now been demonstrated that the cyclic nucleotide-gated channel β-subunits can form homotetrameric channels that can be activated by nitric oxide (NO) modification of a cytoplasmic cysteine residue {Broillet & Firestein, 1997}. Although the physiological significance of this is uncertain and homomeric expression of the γ-subunits of Shal has not yet been demonstrated we are going to explore the possibility that the present family of BCNG channel subunits need additional subunits to form functional channels.

Although the amino acid substitutions seen in the P region of the BCNG subunits do not necessarily indicate that the channel will have lost its K selectivity (for example a lysine is present in the P region of the K selective Shaw channel, See FIG. 14) the substantial deviations from the K channel consensus sequence suggest that the BCNG proteins may generate a family of channels that do not select well between Na and K—consistent with the hypothesis that the BCNG channels encode the non-selective Ih current.

Discussion

Significance of the BCNG Structure

The presence of cyclic nucleotide binding sites on a number of K$^+$ channels that are found in both plant and animal phyla suggests that the fusion between an ancestral K$^+$ channel and an ancestral cyclic nucleotide binding site is likely to have occurred prior to the evolutionary separation between plants and animals (Warmke and Ganetzky, 1994). Indeed, the finding that many of these sites are degenerate and non-functional supports this interpretation. Divergence from this common ancestor would have led on one hand to Eag-related channels (EAG, ERG, ELK) (Warmke and Ganetsky, 1994) and plant inward rectifiers (AKT and KAT), which maintained more of the features of voltage activated K$^+$ channels, while showing a progressive deviation from the original cyclic nucleotide binding site sequence) and on the other hand to CNG-channels (which show a higher evolutionary constraint on the cyclic nucleotide binding site, while they have lost voltage activation and K$^+$ selectivity) (Anderson, et al., 1992; Sentenac, et al., 1992). The features of BCNG-1 suggest that it may have remained closer to the ancestral molecule that represents the evolutionary link between voltage-gated K$^+$ channels and cyclic nucleotide-gated channels. This is supported by the observations that the cyclic nucleotide binding site of mBCNG-1 shows the closest homology to binding sites present in protein kinases, in particular in yeast cAMP-dependent protein kinases (25%) while the channel domains are most closely related to the voltage-dependent channel encoded by the Shaker gene that does not have a cyclic nucleotide binding site and thus, presumably arose before the gene fusion event. The cyclic nucleotide binding site of mBCNG-1 is most homologous to the site present in cyclic nucleotide-gated channels (30%) which again demonstrates that these probably arose from a common ancestor and in both there was pressure to maintain the cyclic nucleotide binding site because it contributed to the function of the protein. Thus, BCNG-1 appears to constitute a new branch of the K$^+$ channel superfamily.

Physiological Significance. Ion channels are central components underlying the electrical activity of all excitable cells and serve important transport functions in non-excitable cells. Members of the novel BCNG family of ion channels are expressed in both brain and cardiac muscle as well as skeletal muscle, lung, liver and kidney. From their amino acid sequence, members of the BCNG channel gene family are likely to have important, novel roles in the electrophysiological activity of the brain and the heart and other tissues. This view is based, first, on the finding that mRNA coding for BCNG channel protein is expressed in both heart and brain. Second, the deduced primary amino acid sequence of the BCNG channels indicate that they are members of the voltage-gated channel family but unlike most voltage-gated channels, the BCNG channels contain what appears to be a functional cyclic nucleotide-binding domain in their carboxy terminus.

Northern blots of the four mouse BCNG channel genes show interesting differences in expression patterns (see FIG. 3, FIG. 9 and FIG. 10). mBCNG-1 is selectively expressed in brain. Western blots confirm that mBCNG-1 is also highly expressed at the protein level, and that this expression is widespread throughout the mouse brain (see FIG. 2). mBCNG-2 is expressed in brain and heart. mBCNG-3 is expressed in brain, heart, lung and skeletal muscle. mBCNG-4 is expressed in brain, liver and kidney. Thus, each gene, although highly similar at the amino acid level, shows a distinct pattern of expression, implying that each has a unique physiological function. This is borne out by the finding that the two human members of the BCNG family, hBCNG-1 and hBCNG-2, show similar patterns of expression to the mouse homologs. Thus, hBCNG-1 is selectively expressed in brain whereas hBCNG-2 is expressed in brain and heart. Even within a particular organ system, the different genes show different patterns of expression. Thus, in the brain hBCNG-1 is more highly expressed in hippocampus and amygdala than in other brain regions. In contrast, hBCNG-2 is highly expressed in all brain regions.

Based on the BCNG amino acid sequence and tissue distribution, it is hypothesized that the channels encode a either a voltage-gated potassium channel that is activated by membrane depolarization and modulated by the direct binding of cyclic nucleotides, or the hyperpolarization-activated pacemaker channel that underlies spontaneous electrical activity in the heart (DiFrancesco and Torta, 1991) and in various regions of the brain (Steride et al., 1993). This latter hypothesis is based on the finding that the pacemaker channels, similar to BCNG genes, are expressed in both brain and the heart. Moreover, the pacemaker channels are known to be non-selective cation channels that are gated by both voltage and the direct binding of cyclic nucleotides to a cytoplasmic site on the channel (DiFrancesco and Torta, 1991; Pedarzani and Storm, 1995 Larkman And Kelly, 1997; McCormick and Page, 1990). To date, there is no biochemical or molecular biological information as to the nature of the pacemaker channel. However, the similarity in tissue distribution and proposed gating mechanisms between the pacemaker channels and the BCNG channels suggests that the BCNG genes code for one or more subunits that comprise the pacemaker channels.

Pacemaker channels have been studied at the electrophysiological level in both cardiac tissue and central neurons. In both instances, the channels are activated when the cell membrane voltage is made more negative than −40 mV. These non-selective channels are permeable to both Na and $K^+$ ions. However, at the negative membrane potential range over which these channels open, their main effect is to allow positively charged sodium to enter the cell from the extracellular environment, causing the cell membrane to become more positive. This eventually causes the membrane voltage to reach threshold and the cell fires an action potential. (See FIG. 15). Cyclic AMP (cAMP) is known to shift the relation between membrane voltage and channel activation, causing the channels to turn on more rapidly when the membrane is depolarized. This increases the rate of the pacemaker depolarization, increasing the rate of spontaneous action potential firing. It is this effect that underlies the ability of epinephrine (adrenaline) to cause the heart to beat faster. The effects of cAMP on the pacemaker current appear to occur through two separate molecular mechanisms. First, cAMP activates the enzyme, cAMP-dependent protein kinase (PKA), leading to an increase in levels of protein phosphorylation. Second, cAMP is thought to directly bind to a cytoplasmic region of the pacemaker channel, producing an effect similar to that seen with protein phosphorylation. Such direct actions of cAMP have been reported both in the heart and in brain (DiFrancesco and Torta, 1991; Pedarzani and Storm, 1995).

An alternative function for the BCNG channels, that they encode for a novel voltage-gated and cyclic nucleotide-gated potassium channel, is suggested by the amino acid region that is known to line the ion-conducting pore and hence determine the ionic selectivity of the channel. This S5–S6 loop contains a three amino acid motif, GYG, that is conserved in almost all voltage-gated $K^+$ channels Heginbotham et al., 1994. The BCNG channel S5–S6 loop shows amino acid similarity with that of other potassium channels, including the GYG motif. This suggests that the BCNG channels may be $K^+$ selective. However, there are a number of striking differences in the sequence between BCNG and other $K^+$ channels that may indicate that the BCNG channels are less K-selective compared to other $K^+$ channels, consistent with the view that the BCNG channels code for the non-selective cation pacemaker channels that are permeable to both Na and $K^+$.

The presence of BCNG-1 in the dendrites of hippocampal pyramidal cells is particularly intriguing, as cAMP has been shown to be important for the establishment of some forms of long-term synaptic potentiation in these cells (Frey, et al., 1993; Boshakov, et al., 1997; Huang and Kandel, 1994; Thomas, et al., 1996).The structural features of BCNG1 predict a $K^+$ conducting activity, directly modulated by cyclic nucleotide binding.

Interestingly, a current with similar characteristics has been described in the hippocampal pyramidal neurons of area CA1 (Warmke, et al., 1991) where BCNG-1 is highly expressed. This current (IQ) is believed to contribute to the noradrenergic modulation of hippocampal activity, by regulating neuronal excitability in response to cAMP levels. BCNG-1 may participate in the formation of the channels responsible for this type of current.

By analogy with the emerging pattern for olfactory and retinal CNG-channels, the non-consensus sequence of the putative pore forming region of mBCNG-1 suggests that this protein may represent a β-subunit of a heteromultimeric channel (Liman and Buck, 1994; Bradley, et al., 1994). Indeed the data show the existence of a number of BCNG-related sequences in the mouse genome, and one or more of these genes could encode additional subunits required for the formation of an active channel. These channels are likely to have two important physiological properties that suggest they serve important functions in the role of many excitable cells. First, they are members of the voltage-gated channel family and are most similar to voltage-gated $K^+$ channels. Second, they possess a cyclic nucleotide binding domain in their carboxy terminus, suggesting that they will be directly regulated by cyclic nucleotides. Based on these properties, combined with their tissue distribution and high levels of expression at the mRNA levels, these channels are likely to play important roles in controlling neuronal and cardiac electrical activity as well as having important functions in other excitable and non-excitable cells.

Based on the widespread tissue distribution and likely important physiological role of the BCNG channels in electrical signaling, drugs that interact with these channels are of potential therapeutic use in a number of neurological, psychiatric and cardiac diseases as well as systemic diseases of tissues such as skeletal muscle, liver and kidney.

Neurological disease: Based on the high expression of these channels in the hippocampus and potential role in spontaneous pacemaker activity, they may be useful, novel targets for treatment of epilepsy. For example, by blocking these channels it may be possible to prevent or diminish the severity of seizures. In diseases associated with hippocampal neuronal loss, such as age-related memory deficit, stroke-induced memory loss, and Alzheimers disease, a drug which enhanced pacemaker channel activity may be of therapeutic use by increasing neuronal activity in the hippocampus. As these channels are also expressed in the basal ganglia and striatum, they may be potential targets in Parkinson's and Huntington's disease. The BCNG channels are also highly expressed in the thalamus, where pacemaker channels have been shown to be important in generating spontaneous action potentials important for arousal. Targeting of such channels may help treat attention deficit disorder.

Psychiatric disease: Given the high levels of expression of hBCNG-1 in the amygdala, these channels may be targets for drugs involving various affective disorders and anxiety. Their high expression in the limbic system suggests that they may also be of potential benefit in treatment of schizophrenia.

Cardiac disease: The expression of the BCNG-2 channels in the heart suggests that they may be useful targets for treatment of certain cardiac arrhythmias. Based on the hypothesis that these genes may encode pacemaker channels, the BCNG channels will be potential targets for treating both bradyarrhythmias through drugs that enhance pacemaker channel activity and certain tachyarrhythmias due to enhanced automaticity. Even if the BCNG channels are not the pacemaker channels, they are likely to play an important role in cardiac electrical activity, perhaps contributing to action potential repolarization, and thus would remain attractive targets for drug development.

A number of drugs, toxins and endogenous compounds are known to interact with various types of ion channels. These drugs have proved useful as local anesthetics and in the treatment of cardiac arrhythmias, hypertension, epilepsy and anxiety. These drugs fall into several classes including pore blockers, allosteric modulators, and competitive antagonists (see Table II). The BCNG channels present some unique features that make them very attractive drugs. First, there are both brain specific genes (BCNG-1) and genes that expressed in both brain and heart (BCNG-2,3). Thus BCNG may yield drugs specific for brain or heart. Second, the pore region of the BCNG channels shows considerable divergence from that of other known potassium channels. Thus, yielding pore-blocking drugs that would selectively alter BCNG channels but spare other types of voltage-gated K+ channels. Third, the cyclic nucleotide-binding site elucidate another important target with respect to the opening of the BCNG channels. By designing specific cyclic nucleotide analogs it should be possible to design either synthetic agonists, which will increase channel opening, or antagonists which will decrease channel opening. Most available drugs for ion channels decrease channel opening, relatively few increase channel opening. The ability to either increase or decrease the opening of BCNG channels offers much potential for therapeutically effective compounds. For example in bovine photoreceptor CNG channels, Rp-cGMPS is an antagonist of channel opening whereas Sp-cGMPS is an agonist (Kramer and Tibbs, 1996). Moreover, the amino acid sequence of the cyclic nucleotide binding site of the BCNG channels shows considerable divergence with cyclic nucleotide binding sites of protein kinases and the cyclic nucleotide-gated channels of olfactory and photoreceptor neurons. Thus it should be possible to design cyclic nucleotide analogs which specifically target the BCNG channels.

TABLE II

Drugs and Toxins That Interact with Members of the Voltage-gated Ion Channel Family.

| Compound | Channel targets | Site of action | Therapeutic Uses |
|---|---|---|---|
| Local Anesthetics (lidocaine, procaine, etc.) | Na | Pore (S6) | Local analgesia, arrhythmias |
| diphenylhydantoin | Na | Pore | Seizures |
| Tetrodotoxin | Na | Pore | |
| Saxitoxin | Na | Pore | |
| α,β-Scorpion toxin | Na | Activation and Inactivation gates | |
| Dihydropyridines | Ca (L-type) | Pore | arrhythmias, hypertension, angina |
| Verapamil | Ca (L-type) | Pore | |
| Diltiazem | Ca (L-type) | Pore | |
| w-conotoxin | Ca (N-type) | Pore | |
| w-agatoxin | Ca (P-type) | Pore | |

TABLE II-continued

Drugs and Toxins That Interact with Members of the Voltage-gated Ion Channel Family.

| Compound | Channel targets | Site of action | Therapeutic Uses |
|---|---|---|---|
| Tetraethylammonium | K | Pore | |
| 4-aminopyridine | K | Pore | |
| charybdotoxin | K | Pore | |
| hanatoxin | K | activation Gate | |
| amiodarone | K | ? | arrhythmias |
| 1-cis-diltiazem | CNG | Pore | |
| Rp-cAMPS | CNG | Binding site antagonist | |
| Sp-cAMPS | CNG | Binding site agonist | |

(Hille, 1992; Catterall, 1992; Roden, 1996)

From their amino acid sequence, these channels are likely to have three important physiological properties that make them a priori attractive targets for drug development. First, their gating should be voltage-dependent and thus it should be sensitive to modulation of the voltage-gating mechanism. Second, they possess a cyclic nucleotide binding domain in their C-terminus and it is probable that their gating will be modulated by direct binding of cyclic nucleotides. This presents a second target for drug targeting. Third, the unusual sequence of the pore forming domain of the BCNG channels should allow the ion conduction properties of the channel to be selectively targeted.

If, the gating of the channels involves both the voltage-sensor machinery and the cyclic nucleotide binding site it is likely that coordinated drug regimes such that two compounds with low efficacy and even low selectivity can combine to selectively target the BCNG channels. Thus one compound that alone would have weak pharmacological effects on many voltage-activated channels combined with one that has a similarly weak effect on the various cyclic nucleotide binding pockets could be applied together. As no class of molecules is currently known that functionally combines BOTH of these structural elements—with the anticipated exception of the BCNG channels—it is likely that such a regime would lead to a highly efficacious and selective targeting of channels containing the BCNG sub-units. Selective intervention against BCNG sub-types should also be possible.

The regulation of these channels through drugs provides a unique opportunity for regulating electrical activity associated with diseases as diverse as epilepsy and cardiac arrhythmias. Moreover, the cyclic nucleotide binding domain of these channels provides a unique pharmacological target that could be used to develop novel, specific, cyclic nucleotide agonists or antagonists to upregulate or downregulate channel function.

Drugs can modulate voltage-dependent gating—coupled with CNG to achieve selectivity.

Cell lines expressing BCNG-1, mBCNG-2, mBCNG-3, mBCNG-4, hBCNG-1 and hBCNG-2 offer the promise of rapid screening for compounds that interact with the channels. To identify drugs that interact with the cyclic nucleotide binding domain, this region could be expressed selectively in bacteria and then purified. The purified protein fragment could then be used in standard ligand-binding assays to detect cyclic nucleotide analogs that bind with high affinity.

Functional effects of drugs on channel opening or ion permeation through the pore are tested using whole cell patch clamp of mammalian cell lines expressing the various BCNG genes. Where the BCNG channels resemble the CNG channels, they exhibit significant permeability to calcium. This permits a high throughput screen in which channel function is assessed by imaging intracellular calcium concentration. Drugs that increase channel opening also increase internal calcium.

EXAMPLE 4
Expression of Functional BCNG Proteins

As the BCNG genes appear to encode an ion channel, mBCNG-1 is expressed in Xenopus oocytes by injection of cRNA and current is recorded using both two electrode voltage clamp and excised inside-out patch clamp approaches. A lack of current may result from a failure of correct trafficking or proper post-translational modification. In an attempt to over come such problems and to obtain functional expression of the BCNG channels, alternative expression systems are utilized. BCNG channels are expressed in a human cell line such as HEK293 cells, or in an insect cell line such as SF9 cells. Proper post-translational modification provided by the mammalian HEK293 cells or the efficient protein production of the insect cell system, may be required to yield a functional ion channel. As each new subunit of the BCNG family is cloned they are expressed in each of the systems described above. Some members of the family may form functional homomultimers (eg. as is seen with some subunits of cyclic nucleotide gated channels and the some of the neuronal nicotinic acetylcholine receptor subunits).

Cloning Additional Subunits that Interact with the BCNG Proteins to Give Rise to Functional Current Coexpression of BCNG channel subunits and candidate proteins. Although the BCNG clones show considerable homology, it is possible that the subunits that are expressed in the same tissue form heteromultimeric proteins with each other and the homomultimers are non-functional. In order to delineate the functional roles of new BCNG subunits, new BCNG subunits are coexpressed with BCNG subunits that have overlapping tissue distribution. Voltage-gated K⁺ channels and cyclic nucleotide-gated channels both form heteromultimers. In some cases, the subunits can form complexes with completely distinct proteins (eg. KvLQT1 with MinK—(Barhanin, et al., 1996; HERG with MinK McDonald, et al., 1997); IrK6.1 and IrK6.2 with the sulphonylurea receptor—Isomoto, et al., 1996; Inagaki, et al., 1996). BCNG proteins may assemble with subunits such as MinK or ERG like subunits. Candidate proteins are selected on the basis of overlapping tissue distribution and likelihood based on known functional properties. For example, Kv1.2 shows overlapping distribution with mBCNG-1 even at the subcellular level (Sheng, et al., 1994; Wang, et al., 1994).

Coexpression with polyA+ mRNA. If another protein is required to form a functional heteromultimer with the BCNG channel proteins, co-expression with size fractionated mRNA from tissue (eg. heart, brain, muscle or kidney) where the appropriate BCNG subunit is expressed (as shown by Northern blot analysis) should result in a unique current in electrophysiological currents when the BCNG RNA is coinjected with the mRNA from the tissue.

Alternative strategies to clone subunits that will permit functional expression of the BCNG channels include low stringency homology screening of the appropriate libraries using BNA nucleotide probes derived from the current BCNG genes or PCR amplification from genomic or cDNA using degenerate oligonucleotides based on the known BCNG genes.

Yet another method to isolate other channel subunit proteins that may coassemble with identified BCNG family members is to use the yeast two hybrid system (Fields and Soug, 1989). This system was initially used to clone mBCNG-1 based on its interaction with the n-src SH3 domain. Conserved cytoplasmic N- and C-terminal domains from BCNG channel proteins are used as the 'bait' in the yeast two hybrid system. N- and C-terminal fragments will be subcloned in the plasmid pEG202 (Zervos et al., 1983).

REFERENCES

Adelman, J. P., Shen, K.-Z., Kavanaugh, M. P., Warren, R. A., Wu, Y.-N., Lagrutta, A., Bond, C. T., & North, R. A. (1992) Neuron 9, 209–216.

Adelman, J. P. (1995) Current Opinion in Neurobiology 5, 286–295.

Aiba, H., Fujimoto, S. and Ozaki, N. (1982) Nucleic Acids Res. 10:1345–1361.

Anderson, J. A., Huprikar, S. S., Kochian, L. V., Lucas, W. J. and Gaber, R. F. (1992) Proc. Natl. Acad. Sci. 89:3736–3740.

Arancio, O., Kandel, E. R., & Hawkins, R. D. (1995) Nature 376, 74–80.

Atkinson, N. S., Robertson, G. A., & Ganetzky, B. (1991) Science 253, 551–555.

Ausubel, F. M., Brent, R., Kingston, R. E., Moore, D. D., Seidman, J. G., Smith, J. A.,& Struhl, K. (1994) Current Protocols in Molecular Biology (John Wiley and Sons, New York, N.Y.).

Barhanin, J., Lesage, F., Guillemare, E., Fink, M., Lazdunski, M. & Romey, G. (1996) Nature 384:78–80.

Barton, S. K. et al., 1992 J. Am. Chem. Soc. 114:8736–40.

Bolshakov, V. Y., Golan, H., Kandel, E. R., & Siegelbaum, S. A.(1997) Neuron 19,635–651.

Bradley, J., Zhang, Y, Bakin, R., Lester, H. A., Ronnett, G. V., & Zinn, K. (1997) J. of Neurosci. 17, 1993–2005.

Bradley, J., Li, J., Davidson, N., Lester, H. A., & Zinn, K. (1994) Proc. Natl. Acad. Sci USA 91, 8890–8894.

Breede, L., & Nasmyth, K. (1985) Cold Spring Harbor Symp. Quant. Biol. 50, 643–650.

Broillet, M. C. & Firestein, S. (1997) Neuron 18: 951–958.

Brugge, J. S., Cotton, P. C., Querel, A. E., Barrett, J. N., Nonner, D., & Keane, R. W. (1985) Nature 316, 554–557.

Brüggemann, A., Pardo, L., Stühmer, W., & Pongs, O. (1993) Nature 365, 445–448.

Chen, T. Y., Peng, Y. W., Dhallan, R. S., Ahamed, B., Reed, R. R, & Yau K. W. (1993) Nature 362, 764–767.

Cossart, P. and Gicquel-Sanzey, B. (1982) Nucleic Acids Res. 10: 1363–1378.

Dale, R. N. K. et al., 1973 Proc. Natl. Acad. Sci. USA 70:2238–42.

Dhallan, R. S., Yau, K. W., Schrader, K. A., and Reed, R. R. (1990) Nature 347, 184–187.

Erickson, P. F. et al., 1982 J. Immunol. Methods 51:241–49.

Fields S., & Song O. K. (1989) Nature 340, 245–246.

Frangioni, J. V., & Neel, B. G. (1993) Anal. Biochem. 210, 179–187.

Frey, U, Huang, Y.-Y., & Kandel, E. R. (1993) Science 260, 1661–1664.

Goulding, E. H., Ngai, J., Kramer, R. H., Colicos, S., Axel, R., Siegelbaum, S. A. and Chess, A. (1992) Neuron 8:45–58.

Goulding, E. H., Tibbs, G. R. and Siegelbaum, S. A. (1994) Nature 372:369–374.

Grant, S. G. N., Karl, K. A., Kiebler, M., & Kandel, E. R. (1995) Genes Dev. 9, 1909–1921.

Greene, W. N., & Millar, N. S. (1995) Trends Neurosci. 18, 280–287.

Harlow, E., & Lane, D. (1988) Antibodies: a laboratory manual (Cold Spring Harbor Lab. Press, Cold Spring Harbor, N.Y.).

Hille, B. (1992). Ionic Channels of Excitable Membranes. Sinauer.

Hoshi, T. (1995) J. Gen. Physiol. 105, 309–328.

Huang Y.-Y., & Kandel E. R. (1994) Learning & Memory 1:74–82.

Isomoto, S., Kondo, C., Yamada, M., Matsumoto, S., Higashiguchi, O., Horio, Y., Matsuzawa, Y. & Kurachi, Y. (1996) *J Biol Chem* 271:24321–24324.

Inagaki, N., Gonoi, T., Clement, J. P., Wang, C.Z., Aguilar-Bryan, L., Bryan, J. & Seino, S. (1996) *Neuron* 16:1011–1017.

Jegla, T. & Salkoff, L. *J. Neurosci* (1997) 17, 32–44.

Johnson, T. K. et al., 1983 *Anal. Biochem.* 133:125–131.

Kamb, A., Iverson, L. E., & Tanouye, M. A. (1987) Cell 50, 405–413.

Kamb, A., Iverson, L. E., & Tanouye, M. A. (1987) Cell 50, 405–413.

Kaupp, U. B., Niidome, T, Tanabe, T., Terada, S., Bönigk, W., Stühmer, W., Cook, N. J., Kangawa, K., Matsuo, H., Hirose, T., Miyata, T., & Numa, S. (1989) Nature 342, 762–766.

Kingston, P. A., Zufall, F., & Barnstable, C. J. (1996) Proc. Natl. Acad. Sci. USA 93,10440–10445.

Kohler, M., Hirschberg, B., Bond, C. T., Kinzie, J. M., Marrion, N. V., Maylie, J., & Adelman, J. P. (1996) Science 273, 1709–1714.

Kramer, R. H. and Tibbs, G. R. (1996) *J. Neurosci.* 16:1285–1293.

Krapivinsky, G., Krapivinsky, L., Wickman, K., & Clapham, D. E. (1995) J. Biol. Chem. 270,29059–29062.

Kumar, V. D. and Weber, I. T. (1992) *Biochemistry* 31:4643–4649.

Liman, E. R., & Buck, L. B. (1994) Neuron 13, 1–20.

Liman, E. R., Hess, P., Weaver, F. & Koren, G. *Nature* (1991) 353: 752–756.

Martinez, R., Mathey-Prevot, B., Bernards, A., & Baltimore, D. (1987) Science 237, 411–415.

McDonald, T. V., Yu, Z., Ming, Z., Palma, E., Meyers, M. B., Wang, K. W., Goldstein, S. A. & Fishman, G. I. (1997) *Nature* 388:289–292.

Matthaei, F. S. et al., (1986) *Anal. Biochem.* 157:123–128.

Mayford, M., Wang, J., Kandel, E. R., & O'Dell, T. J. (1995) Cell 81:891–904.

Palay, S. L., & Chan-Palay, V. (1974) Cerebellar cortex: cytology and organization (Springer, New York, N.Y.).

Pallanck, L., & Ganetzky, B. (1994) Hum. Mol. Genet. 3, 1239–1243.

Papazian, D. M., Schwartz, T. L., Tempel, B. L., Jan, Y. N., & Jan, L. Y. (1987) Science 237, 749–753.

Papazian, D. M., Tempe, L. C., Jan, Y. N., & Jan, L. Y. (1991) Nature 349:305–310.

Pawson, T. (1995) Nature 373, 573–580.

Pedarzani, P., & Storm, J. F. (1995) Proc. Natl. Acad. Sci. USA 92, 11716–11720.

Pedarzani, P., & Storm, J. F. (1995) Proc. Natl. Acad. Sci. USA 92, 11716–11720.

Pongs, O., (1992) Physiol. Rev. 72: S69–S88.

Raisman, G., Cowan, W. M., & Powell, T. P. S. (1965) Brain 88:963–996.

Roden, D. (1996). Antiarryhthmic drugs. In, The Pharmacological Basis of Therapeutics, ninth ed. Eds, Hardman, J.G ., Limbird, L. E. McGraw Hill, New York.

Sambrook, J., Fritsch, E. F., & Maniatis, T. (1989) Molecular cloning: a laboratory manual (Cold Spring Harbor Lab. Press, Cold Spring Harbor, N.Y.) 2nd Ed.

Scott, S.-P., Harrison, R. W., Weber, I. T. and Tanaka, J. C. (1996) *Protein Engineering* 9:333–344.

Sentenac, H., Bonneaud, N., Minet, M., Lacroute, F., Salmon, J.-M., Gaymard, F. and Grignon, C. (1992) *Science* 256:663–665.

Shabb, J. B. and Corbin, J. D. (1992) *J. Biol. Chem.* 267, 5723–5726.

Sheng, M., Tsaur, M.-L., Jan, Y. N., & Jan, L. Y. (1994) J. Neurosci. 14, 2408–2417.

Staub, O., Dho, S., Henry, P. C., Correa, J., Ishikawa, T., McGlade, J., & Rotin, D. (1996) EMBO J. 15, 2371–2380.

Strong, M., Chandy, G., & Gutman, G. (1993) Mol. Biol. Evol. 10, 221–242.

Su, Y., Dostmann, W. R. G., Herberg, F. W., Durick, K., Xuong, N-H., Ten Eyck, L., Taylor, S. S. and Varughese, K. I. (1995) *Science* 269:807–813.

Sudol, M. (1996) TIBS 21, 161–163.

Sugrue, M. M., Brugge, J. S., Marshak, D. R., Greengard, P., & Gustafson, E.L. (1990) J. Neurosci. 10, 2513–2527.

Thomas M. J., Moody T. D., Makhinson M., and O'Dell, T. J. (1996) Neuron 17, 475–482.

Titani, K., Sasagawa, T., Ericsson, L. H., Kumar, S., Smith, S. B., Krebs, E. G. and Walsh, K. A. (1984) *Biochemistry* 23:4193–4199.

Varnum, M. D., Black, K. D. and Zagotta, W. N. (1995) *Neuron* 15:619–625.

Wang, H., Kunkel, D. D., Schwartzkroin, P. A., & Tempel, B. L. (1994) J. Neurosci. 14, 4588–4599.

Warmke, J. W., & Ganetzky, B. (1994) Proc. Natl. Acad. Sci. USA 91, 3438–3442.

Warmke, J, Drysdale, R., & Ganetzky, B. (1991) Science 252, 1560–1562.

Weber, I. T., Shabb, J. B., & Corbin, J. D. (1989) Biochemistry 28, 6122–6127.

Weber, I. T. and Steitz, T. A. (1987) *J. Mol. Biol.* 198:311–326.

Wohlfart, P., Haase, W., Molday, R. S., & Cook, N. J. (1992) J. Biol. Chem. 267, 644–648.

Zagotta, W. N., & Siegelbaum, S. A. (1996) Annu. Rev. Neurosci. 19, 235–263.

Zervos, A. S., Gyuris, J., & Brent, R. (1993) Cell 72, 223–232.

What is claimed is:

1. An isolated nucleic acid that encodes a cyclic nucleotide-gated ion channel protein and that specifically hybridizes with SEQ ID NO:1, or the complement thereof, under conditions comprising two thirty-minute washes at. 65° C. in a solution comprising 0.2×SSC and 0.1% SDS.

2. A composition comprising the nucleic acid of claim 1 and a carrier.

3. An isolated nucleic acid having a sequence encoding a brain cyclic nucleotide gate ion channel protein which sequence is shown in SEQ ID NO:1.

4. The nucleic acid of claim 1, wherein the nucleic acid is DNA or RNA.

5. The nucleic acid of claim 4, wherein the DNA is cDNA.

6. A vector comprising the nucleic acid of claim 4.

7. The vector of claim 6, wherein the vector is a virus or a plasmid.

8. A host-vector system for the production of a mammalian brain cyclic nucleotide-gated ion channel protein which comprises the vector of claim 6 in a suitable host cell.

9. The host vector system of claim 8, wherein the suitable host is a bacterial cell, a eukaryotic cell, a mammalian cell or an insect cell.

10. A composition comprising a nucleic acid having a sequence encoding a BCNG protein which sequence is shown in SEQ. ID. No.:1 and a carrier.

* * * * *

SEQUENCE LISTING

<160> NUMBER OF SEQ ID NOS: 60

<210> SEQ ID NO 1
<211> LENGTH: 2733
<212> TYPE: DNA
<213> ORGANISM: mouse

-continued

```
<400> SEQUENCE: 1
atggaaggcg gcggcaaacc caactccgcg tccaacagcc gcgacgatgg caacagcgtc      60
ttcccctcca aggcgcccgc gacggggccg gtggcggccg acaagcgcct ggggaccccg     120
ccgaggggcg gcgcggccgg gaaggaacat ggcaactccg tgtgcttcaa ggtggacggc     180
ggcggaggag aggagccggc gggcagcttc gaggatgccg aggggccccg gcggcagtat     240
ggtttcatgc agaggcagtt cacctccatg ctgcagcctg gggtcaacaa attctccctc     300
cgcatgtttg ggagccagaa ggcggtggag aaggagcagg aaagggttaa aactgcaggc     360
ttctggatta tccatccgta cagtgacttc aggtttttat tgggatttaa tcatgcttata    420
atgatggttg aaatttggt catcatacca gttggaatca cgttcttcac agagcagacg      480
acaacaccgt ggattatttt caacgtggca tccgatactg ttttcctgtt ggacttaatc     540
atgaattta ggactgggac tgtcaatgaa gacagctcgg aaatcatcct ggaccctaaa      600
gtgatcaaga tgaattattt aaaaagctgg tttgtggtgg acttcatctc atcgatcccg     660
gtggattata tctttctcat tgtagagaaa gggatggact cagaagttta caagacagcc     720
agagcacttc gtatcgtgag gtttacaaaa attctcagtc tcttgcggtt attacgcctt     780
tcaaggttaa tcagatacat acaccagtgg aagagagata tccacatgac ctatgacctc     840
gccagtgctg tggtgaggat cttcaacctc attggcatga tgctgcttct gtgccactgg     900
gatggctgtc ttcagttcct ggttcccctg ctgcaggact tcccaccaga ttgctgggtt     960
tctctgaatg aaatggttaa tgattcctgg ggaaaacaat attcctacgc actcttcaaa    1020
gctatgagtc acatgctgtg cattggttat ggcgcccaag cccctgtcag catgtctgac    1080
ctctggatta ccatgctgag catgattgtg ggcgccacct gctacgcaat gtttgttggc    1140
catgccacag ctttgatcca gtctttggac tcttcaagga ggcagtatca agagaagtat    1200
aagcaagtag agcaatacat gtcattccac aagttaccag ctgacatgcg ccagaagata    1260
catgattact atgagcaccg ataccaaggc aagatcttcg atgaagaaaa tattctcagt    1320
gagcttaatg atcctctgag agaggaaata gtcaacttca actgccggaa actggtggct    1380
actatgcctc tttttgctaa cgccgatccc aatttcgtga cggccatgct gagcaagctg    1440
agatttgagg tgttccagcc cggagactat atcattcgag aaggagctgt ggggaagaaa    1500
atgtatttca tccagcacgg tgttgctggc gttatcacca agtccagtaa agaaatgaag    1560
ctgacagatg gctcttactt cggagagata tgcctgctga ccaagggccg gcgcactgcc    1620
agtgtccgag ctgatacctac tgtcgtctt tactccctt cggtggacaa tttcaatgag     1680
gtcttggagg aatatccaat gatgagaaga gcctttgaga cagttgctat tgaccgactc    1740
gatcggatag gcaagaaaaa ctctattctc ctgcagaagt tccagaagga tctaaacact    1800
ggtgttttca acaaccagga gaacgagatc ctgaagcaga tcgtgaagca tgaccgagag    1860
atggtacaag ctatccctcc aatcaactat cctcaaatga cagccctcaa ctgcacatct    1920
tcaaccacca ccccaacctc ccgcatgagg acccaatctc cgccagtcta caccgcaacc    1980
agcctgtctc acagcaatct gcactcaccc agtcccagca cacagacgcc ccaaccctca    2040
gccatccttt caccctgctc ctataccaca gcagtctgca gtcctcctat acagagcccc    2100
ctggccacac gaactttcca ttatgcctct cccactgcgt cccagctgtc actcatgcag    2160
cagcctcagc agcaactacc gcagtcccag gtacagcaga ctcagactca gactcagcag    2220
cagcagcagc aacagcagca gcagcagcag cagcaacagc aacaacagca gcagcagcag    2280
cagcagcagc agcagcagca gcagcagcag cagcagcagc agcagccaca gacacctggt    2340
```

-continued

```
agctccacac cgaaaaatga agtgcacaag agcacacaag cccttcataa caccaacctg    2400
accaaagaag tcaggcccct ttccgcctcg cagccttctc tgccccatga ggtctccact    2460
ttgatctcca gacctcatcc cactgtgggc gaatccctgg cctctatccc tcaacccgtg    2520
gcagcagtcc acagcactgg ccttcaggca gggagcagga gcacagtgcc acaacgtgtc    2580
accttgttcc gacagatgtc ctcggggagcc atccccccca accgaggagt gcctccagca    2640 cccccctccac cagcagctgt gcagagagag tctccctcag tcctaaatac agacccagat    2700
gcagaaaaac cccgttttgc ttcgaattta tga                                 2733
```

<210> SEQ ID NO 2
<211> LENGTH: 910
<212> TYPE: PRT
<213> ORGANISM: mouse
<220> FEATURE:
<221> NAME/KEY: DOMAIN
<222> LOCATION: (130)..(148)
<223> OTHER INFORMATION: S1
<220> FEATURE:
<221> NAME/KEY: DOMAIN
<222> LOCATION: (164)..(185)
<223> OTHER INFORMATION: S2
<220> FEATURE:
<221> NAME/KEY: DOMAIN
<222> LOCATION: (208)..(229)
<223> OTHER INFORMATION: S3
<220> FEATURE:
<221> NAME/KEY: DOMAIN
<222> LOCATION: (243)..(271)
<223> OTHER INFORMATION: S4
<220> FEATURE:
<221> NAME/KEY: DOMAIN
<222> LOCATION: (291)..(313)
<223> OTHER INFORMATION: S5
<220> FEATURE:
<221> NAME/KEY: DOMAIN
<222> LOCATION: (332)..(358)
<223> OTHER INFORMATION: P
<220> FEATURE:
<221> NAME/KEY: DOMAIN
<222> LOCATION: (367)..(387)
<223> OTHER INFORMATION: S6
<220> FEATURE:
<221> NAME/KEY: DOMAIN
<222> LOCATION: (472)..(602)
<223> OTHER INFORMATION: CNB
<300> PUBLICATION INFORMATION:
<308> DATABASE ACCESSION NUMBER: AAC53518
<309> DATABASE ENTRY DATE: 1997-12-27
<313> RELEVANT RESIDUES: (1)..(910)

<400> SEQUENCE: 2

```
Met Glu Gly Gly Gly Lys Pro Asn Ser Ala Ser Asn Ser Arg Asp Asp
 1               5                  10                  15

Gly Asn Ser Val Phe Pro Ser Lys Ala Pro Ala Thr Gly Pro Val Ala
            20                  25                  30

Ala Asp Lys Arg Leu Gly Thr Pro Arg Gly Gly Ala Ala Gly Lys
        35                  40                  45

Glu His Gly Asn Ser Val Cys Phe Lys Val Asp Gly Gly Gly Glu
    50                  55                  60

Glu Pro Ala Gly Ser Phe Glu Asp Ala Glu Gly Pro Arg Arg Gln Tyr
65                  70                  75                  80

Gly Phe Met Gln Arg Gln Phe Thr Ser Met Leu Gln Pro Gly Val Asn
                85                  90                  95

Lys Phe Ser Leu Arg Met Phe Gly Ser Gln Lys Ala Val Glu Lys Glu
            100                 105                 110
```

-continued

Gln Glu Arg Val Lys Thr Ala Gly Phe Trp Ile Ile His Pro Tyr Ser
            115                 120                 125

Asp Phe Arg Phe Tyr Trp Asp Leu Ile Met Leu Ile Met Met Val Gly
            130                 135                 140

Asn Leu Val Ile Ile Pro Val Gly Ile Thr Phe Phe Thr Glu Gln Thr
145                 150                 155                 160

Thr Thr Pro Trp Ile Ile Phe Asn Val Ala Ser Asp Thr Val Phe Leu
                165                 170                 175

Leu Asp Leu Ile Met Asn Phe Arg Thr Gly Thr Val Asn Glu Asp Ser
            180                 185                 190

Ser Glu Ile Ile Leu Asp Pro Lys Val Ile Lys Met Asn Tyr Leu Lys
            195                 200                 205

Ser Trp Phe Val Val Asp Phe Ile Ser Ser Ile Pro Val Asp Tyr Ile
210                 215                 220

Phe Leu Ile Val Glu Lys Gly Met Asp Ser Glu Val Tyr Lys Thr Ala
225                 230                 235                 240

Arg Ala Leu Arg Ile Val Arg Phe Thr Lys Ile Leu Ser Leu Leu Arg
            245                 250                 255

Leu Leu Arg Leu Ser Arg Leu Ile Arg Tyr Ile His Gln Trp Glu Glu
            260                 265                 270

Ile Phe His Met Thr Tyr Asp Leu Ala Ser Ala Val Val Arg Ile Phe
            275                 280                 285

Asn Leu Ile Gly Met Met Leu Leu Leu Cys His Trp Asp Gly Cys Leu
            290                 295                 300

Gln Phe Leu Val Pro Leu Leu Gln Asp Phe Pro Pro Asp Cys Trp Val
305                 310                 315                 320

Ser Leu Asn Glu Met Val Asn Asp Ser Trp Gly Lys Gln Tyr Ser Tyr
            325                 330                 335

Ala Leu Phe Lys Ala Met Ser His Met Leu Cys Ile Gly Tyr Gly Ala
            340                 345                 350

Gln Ala Pro Val Ser Met Ser Asp Leu Trp Ile Thr Met Leu Ser Met
            355                 360                 365

Ile Val Gly Ala Thr Cys Tyr Ala Met Phe Val Gly His Ala Thr Ala
370                 375                 380

Leu Ile Gln Ser Leu Asp Ser Ser Arg Arg Gln Tyr Gln Glu Lys Tyr
385                 390                 395                 400

Lys Gln Val Glu Gln Tyr Met Ser Phe His Lys Leu Pro Ala Asp Met
            405                 410                 415

Arg Gln Lys Ile His Asp Tyr Tyr Glu His Arg Tyr Gln Gly Lys Ile
            420                 425                 430

Phe Asp Glu Glu Asn Ile Leu Ser Glu Leu Asn Asp Pro Leu Arg Glu
            435                 440                 445

Glu Ile Val Asn Phe Asn Cys Arg Lys Leu Val Ala Thr Met Pro Leu
            450                 455                 460

Phe Ala Asn Ala Asp Pro Asn Phe Val Thr Ala Met Leu Ser Lys Leu
465                 470                 475                 480

Arg Phe Glu Val Phe Gln Pro Gly Asp Tyr Ile Ile Arg Glu Gly Ala
            485                 490                 495

Val Gly Lys Lys Met Tyr Phe Ile Gln His Gly Val Ala Gly Val Ile
            500                 505                 510

Thr Lys Ser Ser Lys Glu Met Lys Leu Thr Asp Gly Ser Tyr Phe Gly
            515                 520                 525

-continued

```
Glu Ile Cys Leu Leu Thr Lys Gly Arg Thr Ala Ser Val Arg Ala
    530                 535                 540
Asp Thr Tyr Cys Arg Leu Tyr Ser Leu Ser Val Asp Asn Phe Asn Glu
545                 550                 555                 560
Val Leu Glu Glu Tyr Pro Met Met Arg Arg Ala Phe Glu Thr Val Ala
                565                 570                 575
Ile Asp Arg Leu Asp Arg Ile Gly Lys Lys Asn Ser Ile Leu Leu Gln
            580                 585                 590
Lys Phe Gln Lys Asp Leu Asn Thr Gly Val Phe Asn Asn Gln Glu Asn
        595                 600                 605
Glu Ile Leu Lys Gln Ile Val Lys His Asp Arg Glu Met Val Gln Ala
    610                 615                 620
Ile Pro Pro Ile Asn Tyr Pro Gln Met Thr Ala Leu Asn Cys Thr Ser
625                 630                 635                 640
Ser Thr Thr Thr Pro Thr Ser Arg Met Arg Thr Gln Ser Pro Pro Val
                645                 650                 655
Tyr Thr Ala Thr Ser Leu Ser His Ser Asn Leu His Ser Pro Ser Pro
            660                 665                 670
Ser Thr Gln Thr Pro Gln Pro Ser Ala Ile Leu Ser Pro Cys Ser Tyr
        675                 680                 685
Thr Thr Ala Val Cys Ser Pro Pro Ile Gln Ser Pro Leu Ala Thr Arg
    690                 695                 700
Thr Phe His Tyr Ala Ser Pro Thr Ala Ser Gln Leu Ser Leu Met Gln
705                 710                 715                 720
Gln Pro Gln Gln Gln Leu Pro Gln Ser Gln Val Gln Gln Thr Gln Thr
                725                 730                 735
Gln Thr Gln Gln Gln Gln Gln Gln Gln Gln Gln Gln Gln Gln Gln Gln
            740                 745                 750
Gln Gln Gln Gln Gln Gln Gln Gln Gln Gln Gln Gln Gln Gln Gln Gln
        755                 760                 765
Gln Gln Gln Gln Gln Gln Pro Gln Thr Pro Gly Ser Ser Thr Pro
    770                 775                 780
Lys Asn Glu Val His Lys Ser Thr Gln Ala Leu His Asn Thr Asn Leu
785                 790                 795                 800
Thr Lys Glu Val Arg Pro Leu Ser Ala Ser Gln Pro Ser Leu Pro His
                805                 810                 815
Glu Val Ser Thr Leu Ile Ser Arg Pro His Pro Thr Val Gly Glu Ser
            820                 825                 830
Leu Ala Ser Ile Pro Gln Pro Val Ala Val His Ser Thr Gly Leu
        835                 840                 845
Gln Ala Gly Ser Arg Ser Thr Val Pro Gln Arg Val Thr Leu Phe Arg
    850                 855                 860
Gln Met Ser Ser Gly Ala Ile Pro Pro Asn Arg Gly Val Pro Pro Ala
865                 870                 875                 880
Pro Pro Pro Ala Ala Val Gln Arg Glu Ser Pro Ser Val Leu Asn
                885                 890                 895
Thr Asp Pro Asp Ala Glu Lys Pro Arg Phe Ala Ser Asn Leu
            900                 905                 910
```

<210> SEQ ID NO 3
<211> LENGTH: 1584
<212> TYPE: DNA
<213> ORGANISM: mouse;

<400> SEQUENCE: 3

```
aagttctccc tgcggatgtt cggcagccag aaggccgtgg agcgcgagca ggaacgcgtg      60
aagtcggcgg gggcctggat catccacccc tacagcgact tcaggttcta ctgggacttc     120
accatgctgt tgttcatggt gggaaatctc attatcattc ccgtgggcat cactttcttc     180
aaggacgaga ccaccgcgcc ctggatcgtc ttcaacgtgg tctcggacac tttcttcctc     240
atggacttgg tgttgaactt ccgcaccggc attgttattg aggacaacac ggagatcatc     300
ctggaccccg agaagataaa gaagaagtac ttgcgtacgt ggttcgtggt ggacttcgtg     360
tcatccatcc cggtggacta catcttcctc atagtggaga agggaatcga ctccgaggtc     420
tacaagacag cgcgtgctct gcgcatcgtg ccgttcacca agatcctcag tctgctgcgg     480
ctgctgcggt atcacggct catccgatat atccaccagt gggaagagat tttccacatg     540
acctacgacc tggcaagtgc agtgatgcgc atctgtaacc tgatcagcat gatgctactg     600
ctctgccact gggacggttg cctgcagttc ctggtgccca tgctgcaaga cttccccagc     660
gactgctggg tgtccatcaa caacatggtg aaccactcgt ggagcgagct ctactcgttc     720
gcgctcttca aggccatgag ccacatgctg tgcatcggct acgggcggca ggcgcccgag     780
agcatgacag acatctggct gaccatgctc agcatgatcg taggcgccac ctgctatgcc     840
atgttcattg gcacgccac tgcgctcatc cagtccctgg attcgtcacg cgccaatac     900
caggagaagt acaagcaagt agagcaatac atgtccttcc acaaactgcc cgctgacttc     960
cgccagaaga tccacgatta ctatgaacac cggtaccaag ggaagatgtc tgatgaggac    1020
agcatccttg gggaactcaa cgggccactg cgtgaggaga ttgtgaactt caactgccgg    1080
aagctggtgg cttccatgcc gctgtttgcc aatgcagacc ccaatttcgt cacagccatg    1140
ctgacaaagc tcaaatttga ggtcttccag cctggagatt acatcatccg agaggggacc    1200
atcgggaaga agatgtactt catccagcat ggggtggtga gcgtgctcac caagggcaac    1260
aaggagatga gctgtcgga tggctcctat ttcgggagac tctgcttgct cacgagggc    1320
cggcgtacgg ccagcgtgcg agctgacacc tactgtcgcc tctactcact gagtgtggac    1380
aatttcaacg aggtgctgga ggaataccc atgatgcggc gtgcctttga gactgtggct    1440
attgaccggc tagatcgcat aggcaagaag aactccacct tgctgcacaa ggttcagcat    1500
gatctcagct ccacgccgcg cctgggaccc gcacccaccg cccggaccgc cgcgcccagt    1560
ccggaccgca ggactcaggg aatt                                           1584
```

<210> SEQ ID NO 4
<211> LENGTH: 528
<212> TYPE: PRT
<213> ORGANISM: mouse;
<300> PUBLICATION INFORMATION:
<308> DATABASE ACCESSION NUMBER: AAC40125
<309> DATABASE ENTRY DATE: 1998-05-29
<313> RELEVANT RESIDUES: (1)..(504)

<400> SEQUENCE: 4

```
Lys Phe Ser Leu Arg Met Phe Gly Ser Gln Lys Ala Val Glu Arg Glu
1               5                  10                  15

Gln Glu Arg Val Lys Ser Ala Gly Ala Trp Ile Ile His Pro Tyr Ser
            20                  25                  30

Asp Phe Arg Phe Tyr Trp Asp Phe Thr Met Leu Leu Phe Met Val Gly
        35                  40                  45

Asn Leu Ile Ile Ile Pro Val Gly Ile Thr Phe Phe Lys Asp Glu Thr
    50                  55                  60
```

-continued

```
Thr Ala Pro Trp Ile Val Phe Asn Val Val Ser Asp Thr Phe Phe Leu
 65                  70                  75                  80

Met Asp Leu Val Leu Asn Phe Arg Thr Gly Ile Val Ile Glu Asp Asn
                 85                  90                  95

Thr Glu Ile Ile Leu Asp Pro Glu Lys Ile Lys Lys Tyr Leu Arg
            100                 105                 110

Thr Trp Phe Val Val Asp Phe Val Ser Ser Ile Pro Val Asp Tyr Ile
        115                 120                 125

Phe Leu Ile Val Glu Lys Gly Ile Asp Ser Glu Val Tyr Lys Thr Ala
    130                 135                 140

Arg Ala Leu Arg Ile Val Pro Phe Thr Lys Ile Leu Ser Leu Leu Arg
145                 150                 155                 160

Leu Leu Arg Leu Ser Arg Leu Ile Arg Tyr Ile His Gln Trp Glu Glu
                165                 170                 175

Ile Phe His Met Thr Tyr Asp Leu Ala Ser Ala Val Met Arg Ile Cys
            180                 185                 190

Asn Leu Ile Ser Met Met Leu Leu Cys His Trp Asp Gly Cys Leu
        195                 200                 205

Gln Phe Leu Val Pro Met Leu Gln Asp Phe Pro Ser Asp Cys Trp Val
    210                 215                 220

Ser Ile Asn Asn Met Val Asn His Ser Trp Ser Glu Leu Tyr Ser Phe
225                 230                 235                 240

Ala Leu Phe Lys Ala Met Ser His Met Leu Cys Ile Gly Tyr Gly Arg
                245                 250                 255

Gln Ala Pro Glu Ser Met Thr Asp Ile Trp Leu Thr Met Leu Ser Met
            260                 265                 270

Ile Val Gly Ala Thr Cys Tyr Ala Met Phe Ile Gly His Ala Thr Ala
        275                 280                 285

Leu Ile Gln Ser Leu Asp Ser Ser Arg Arg Gln Tyr Gln Glu Lys Tyr
    290                 295                 300

Lys Gln Val Glu Gln Tyr Met Ser Phe His Lys Leu Pro Ala Asp Phe
305                 310                 315                 320

Arg Gln Lys Ile His Asp Tyr Tyr Glu His Arg Tyr Gln Gly Lys Met
                325                 330                 335

Ser Asp Glu Asp Ser Ile Leu Gly Glu Leu Asn Gly Pro Leu Arg Glu
            340                 345                 350

Glu Ile Val Asn Phe Asn Cys Arg Lys Leu Val Ala Ser Met Pro Leu
        355                 360                 365

Phe Ala Asn Ala Asp Pro Asn Phe Val Thr Ala Met Leu Thr Lys Leu
    370                 375                 380

Lys Phe Glu Val Phe Gln Pro Gly Asp Tyr Ile Ile Arg Glu Gly Thr
385                 390                 395                 400

Ile Gly Lys Lys Met Tyr Phe Ile Gln His Gly Val Val Ser Val Leu
                405                 410                 415

Thr Lys Gly Asn Lys Glu Met Lys Leu Ser Asp Gly Ser Tyr Phe Gly
            420                 425                 430

Glu Ile Cys Leu Leu Thr Arg Gly Arg Arg Thr Ala Ser Val Arg Ala
        435                 440                 445

Asp Thr Tyr Cys Arg Leu Tyr Ser Leu Ser Val Asp Asn Phe Asn Glu
    450                 455                 460

Val Leu Glu Glu Tyr Pro Met Met Arg Arg Ala Phe Glu Thr Val Ala
465                 470                 475                 480

Ile Asp Arg Leu Asp Arg Ile Gly Lys Lys Asn Ser Thr Leu Leu His
```

```
                   485                 490                 495
Lys Val Gln His Asp Leu Ser Ser Thr Pro Arg Leu Gly Pro Ala Pro
                500                 505                 510
Thr Ala Arg Thr Ala Ala Pro Ser Pro Asp Arg Arg Thr Gln Gly Ile
            515                 520                 525

<210> SEQ ID NO 5
<211> LENGTH: 1507
<212> TYPE: DNA
<213> ORGANISM: mouse;

<400> SEQUENCE: 5
tgcaacagcc ctcggcggac accgctatca aagtggaggg aggcgcggcc gccacaccat      60
atcctccccg aggccgagtg cgcctgggcc aaagcggctt catgcagcgc cagttcggtg     120
ccatgctgca acctggggtc aacaaattct ccctaaggat gttcggcagc caaaagcggt     180
ggagcgcgag caggagaggg ttaatcagca gggttttgga ttatccaccc ctacagtgac     240
ttcagatttt actgggacct gacatctgtt gctgatggtg gggaatctga tcatcatacc     300
cgtgggcatc accttcttca aggatgagaa caccacaccc tggatcgtct tcaatgtggt     360
gtcagacaca ttcttcctca ttgacttggt cctcaacttc cgcacgggga tcgtggtgga     420
ggacaacaca gaaatcatcc ttgacccgca gaggatcaag atgaagtacc tgaaaagctg     480
gtttgtggta gatttcatct cctccatacc tgtcgaatac atttccttat agtggagact     540
cgcattgact cggaggttta caaaaccgct agggctgtgc gcattgtccg tttcataaga     600
tcctcagcct cctgcgcctc ttgaggcttt cccgcctcat tcgatacatt catcagtggg     660
aagagatttt ccacatgacc tatgacctgg ccagcgccgt ggtacgcatc gtgaacctca     720
ttggcatgat gcttctgctg tgtcactggg atggctgcct gcagttccta gtgcccatgc     780
tgcaggactt cccccatgac tgctgggtgt ccatcaatgg catggtgaat aactcctggg     840
ggaagcagta ttcctacgcc ctcttcaagg ccatgagcca catgctgtgc attgggtatg     900
gacggcaggc acccgtaggc atgtctgacg tctggctcac catgctcagc atgatcgtgg     960
gggccacctg ctatgccatg ttcatcggcc acgccactgc cctcatccag tcgctagact    1020
cctcccggcg ccagtaccag gagaagtata acaggtgga gcagtacatg tctttccaca    1080
agctcccgcc tgacacccga cagcgcatcc atgactacta tgaacaccgt taccaaggca    1140
agatgtttga tgaggaaagc atcctgggtg agttgagtga gccacttcga gaggagatca    1200
tcaactttaa ctgccgaaag ctggtggcat ccatgccact gtttgccaac gcagatccca    1260
actttgtgac atccatgctg accaagttgc gtttcgaggt cttccagcct ggggattaca    1320
tcatccgcga aggcaccatc ggcaagaaga tgtactttat ccagcacggc gtggtcagcg    1380
tgctcactaa gggcaacaaa gagaccaggc tggctgatgg ctcctatttt ggagagatct    1440
gcttgctgac ccggggtcgg cgcacagcca gcgtcagagc ggatacttat tccgcctcta    1500
ctcactg                                                              1507

<210> SEQ ID NO 6
<211> LENGTH: 506
<212> TYPE: PRT
<213> ORGANISM: mouse;
<300> PUBLICATION INFORMATION:
<308> DATABASE ACCESSION NUMBER: AAC40126
<309> DATABASE ENTRY DATE: 1998-05-29
<313> RELEVANT RESIDUES: (1)..(506)

<400> SEQUENCE: 6
```

```
Cys Glu Gln Pro Ser Ala Asp Thr Ala Ile Lys Val Glu Gly Gly Ala
  1               5                  10                  15

Ala Ala Ile Asp His Ile Leu Pro Glu Ala Glu Val Arg Leu Gly Gln
             20                  25                  30

Ser Gly Phe Met Gln Arg Gln Phe Gly Ala Met Leu Gln Pro Gly Val
             35                  40                  45

Asn Lys Phe Ser Leu Arg Met Phe Gly Ser Gln Lys Ala Val Glu Arg
 50                  55                  60

Glu Gln Glu Arg Val Lys Ser Ala Gly Phe Trp Ile Ile His Pro Tyr
 65                  70                  75                  80

Ser Asp Phe Arg Phe Tyr Trp Asp Leu Thr Met Leu Leu Leu Met Val
             85                  90                  95

Gly Asn Leu Ile Ile Ile Pro Val Gly Ile Thr Phe Phe Lys Asp Glu
            100                 105                 110

Asn Thr Thr Pro Trp Ile Val Phe Asn Val Val Ser Asp Thr Phe Phe
            115                 120                 125

Leu Ile Asp Leu Val Leu Asn Phe Arg Thr Gly Ile Val Val Glu Asp
130                 135                 140

Asn Thr Glu Ile Ile Leu Asp Pro Gln Arg Ile Lys Met Lys Tyr Leu
145                 150                 155                 160

Lys Ser Trp Phe Val Val Asp Phe Ile Ser Ile Pro Val Glu Tyr
                165                 170                 175

Ile Phe Leu Ile Val Glu Thr Arg Ile Asp Ser Glu Val Tyr Lys Thr
            180                 185                 190

Ala Arg Ala Val Arg Ile Val Arg Phe Thr Lys Ile Leu Ser Leu Leu
            195                 200                 205

Arg Leu Leu Arg Leu Ser Arg Leu Ile Arg Tyr Ile His Gln Trp Glu
210                 215                 220

Glu Ile Phe His Met Thr Tyr Asp Leu Ala Ser Ala Val Val Arg Ile
225                 230                 235                 240

Val Asn Leu Ile Gly Met Met Leu Leu Leu Cys His Trp Asp Gly Cys
            245                 250                 255

Leu Gln Phe Leu Val Pro Met Leu Gln Asp Phe Pro His Asp Cys Trp
            260                 265                 270

Val Ser Ile Asn Gly Met Val Asn Asn Ser Trp Gly Lys Gln Tyr Ser
            275                 280                 285

Tyr Ala Leu Phe Lys Ala Met Ser His Met Leu Cys Ile Gly Tyr Gly
            290                 295                 300

Arg Gln Ala Pro Val Gly Met Ser Asp Val Trp Leu Thr Met Leu Ser
305                 310                 315                 320

Met Ile Val Gly Ala Thr Cys Tyr Ala Met Phe Ile Gly His Ala Thr
                325                 330                 335

Ala Leu Ile Gln Ser Leu Asp Ser Ser Arg Arg Gln Tyr Gln Glu Lys
            340                 345                 350

Tyr Lys Gln Val Glu Gln Tyr Met Ser Phe His Lys Leu Pro Pro Asp
            355                 360                 365

Thr Arg Gln Arg Ile His Asp Tyr Tyr Glu His Arg Tyr Gln Gly Lys
370                 375                 380

Met Phe Asp Glu Glu Ser Ile Leu Gly Glu Leu Ser Glu Pro Leu Arg
385                 390                 395                 400

Glu Glu Ile Ile Asn Phe Asn Cys Arg Lys Leu Val Ala Ser Met Pro
            405                 410                 415
```

```
Leu Phe Ala Asn Ala Asp Pro Asn Phe Val Thr Ser Met Leu Thr Lys
            420                 425                 430

Leu Arg Phe Glu Val Phe Gln Pro Gly Asp Tyr Ile Ile Arg Glu Gly
        435                 440                 445

Thr Ile Gly Lys Lys Met Tyr Phe Ile Gln His Gly Val Val Ser Val
    450                 455                 460

Leu Thr Lys Gly Asn Lys Glu Thr Arg Leu Ala Asp Gly Ser Tyr Phe
465                 470                 475                 480

Gly Glu Ile Cys Leu Leu Thr Arg Gly Arg Arg Thr Ala Ser Val Arg
                485                 490                 495

Ala Asp Thr Tyr Cys Arg Leu Tyr Ser Leu
                500                 505

<210> SEQ ID NO 7
<211> LENGTH: 1060
<212> TYPE: DNA
<213> ORGANISM: mouse;

<400> SEQUENCE: 7
```

| | | |
|---|---|---|
| tttttttttt tttttttttt tgggttttta aaatttattt tattttttaaa agcgtctccg | 60 |
| gaatctagtg catggccagg ctacaagcta ctgggccagc aactctgtag gattattaat | 120 |
| gacaaaaatg caaggacccc atagttgatg aaacccagg gatgaagcag ggctgtccca | 180 |
| cagacttagg ctttgtggag ctgtctgaaa acccaggctg tggctttgga agaagtgcag | 240 |
| acaaccactg cccagagtga cttaaggttc atacaaccat ccagccacct aagcacccc | 300 |
| accttcaagc atcttgccag tcccactttg tgtctgttta gcctgcttt ctcctcccaa | 360 |
| gttaggagtc gggtacaccc tgggacggag caataagact gggggttggag ttaatgtgta | 420 |
| aaataactga aaaaaacatc tggggctggc aaacctgttt gtctggaaaa cagccttcca | 480 |
| gatgtgcagg tatggaaaca gacagtgctt agagcagtaa gggaccttat accagctaat | 540 |
| cgttcattct cccaagtata aggaggaatc tgggggtgct gggttagctg ctgcaggcct | 600 |
| aattgggggg tggaatggga gctctgagct cttccccgct ttcgcagaga tctgcctgct | 660 |
| gattcgaggt cggagaacag ccagtgtaag ggctgacacc tattgtcgcc ttactcgctc | 720 |
| agcgtggacc acttcaatgc ggtgcttgag gagttcccaa tgatgcgcag ggcttttgag | 780 |
| acggtggcca tggaccggct tcggcgcatc ggtgaggcct gtttactctg tctgctctgg | 840 |
| gtcctggctg ggcctcatct catgagccta gccctggtgc tttgacacca catcccagcc | 900 |
| cacccagttc cagtccatgc ctccagcagg ctgttagcac tgttgctcac tagacttagc | 960 |
| cctagcgaga aattgccgtg gagtgtctcc ccaaaccctc attccccgtg tcttctgggt | 1020 |
| accagttctt aacctcacaa ttttttattg atacctcgtg | 1060 |

```
<210> SEQ ID NO 8
<211> LENGTH: 79
<212> TYPE: PRT
<213> ORGANISM: mouse;
<300> PUBLICATION INFORMATION:
<308> DATABASE ACCESSION NUMBER: AAC40127
<309> DATABASE ENTRY DATE: 1998-05-29
<313> RELEVANT RESIDUES: (1)..(78)

<400> SEQUENCE: 8

Glu Ile Cys Leu Leu Ile Arg Gly Arg Arg Thr Ala Ser Val Arg Ala
1               5                   10                  15

Asp Thr Tyr Cys Arg Leu Tyr Ser Leu Ser Val Asp His Phe Asn Ala
            20                  25                  30
```

Val Leu Glu Glu Phe Pro Met Met Arg Arg Ala Phe Glu Thr Val Ala
            35                  40                  45

Met Asp Arg Leu Arg Arg Ile Gly Glu Ala Cys Leu Leu Cys Leu Leu
        50                  55                  60

Trp Val Leu Ala Gly Pro His Leu Met Ser Leu Ala Leu Val Leu
 65                 70                  75

<210> SEQ ID NO 9
<211> LENGTH: 2263
<212> TYPE: DNA
<213> ORGANISM: human

<400> SEQUENCE: 9

| | | | | | |
|---|---|---|---|---|---|
| aaggagcagg | aaagggttaa | aactgcaggc | ttctggatta | tccaccctta | cagtgatttc |   60 |
| aggttttact | gggatttaat | aatgctcata | atgatggttg | gaaatctagt | catcatacca |  120 |
| gttggaatca | cattctttac | agagcaaaca | acaacaccat | ggattatttt | caatgtggca |  180 |
| tcagatacag | ttttcctatt | ggacctgatc | atgaatttta | ggactgggac | tgtcaatgaa |  240 |
| gacagttctg | aaatcatcct | ggaccccaaa | gtgatcaaga | tgaattattt | aaaaagctgg |  300 |
| tttgtggttg | acttcatctc | atccatccca | gtggattata | tctttcttat | tgtagaaaaa |  360 |
| ggaatggatt | ctgaagttta | caagacagcc | agggcccttc | gcattgtgag | gtttacaaaa |  420 |
| attctcagtc | tcttgcgttt | attacgactt | tcaaggttaa | ttagatacat | acatcaatgg |  480 |
| gaagagatat | tccacatgac | atatgatctc | gccagtgcag | tggtgagaat | ttttaatctc |  540 |
| atcggcatga | tgctgctcct | gtgccactgg | gatggttgtc | ttcagttctt | agtaccacta |  600 |
| ctgcaggact | tcccaccaga | ttgctgggtg | tctttaaatg | aaatggttaa | tgattcttgg |  660 |
| ggaaagcagt | attcatacgc | actcttcaaa | gctatgagtc | acatgctgtg | cattgggtat |  720 |
| ggagcccaag | cccagtcag | catgtctgac | ctctggatta | ccatgctgag | catgatcgtc |  780 |
| ggggccacct | gctatgccat | gtttgtcggc | catgccaccg | ctttaatcca | gtctctggat |  840 |
| tcttcgaggc | ggcagtatca | agagaagtat | aagcaagtgg | aacaatacat | gtcattccat |  900 |
| aagttaccag | ctgatatgcg | tcagaagata | catgattact | atgaacacag | ataccaaggc |  960 |
| aaaatctttg | atgaggaaaa | tattctcaat | gaactcaatg | atcctctgag | agaggagata | 1020 |
| gtcaacttca | actgtcggaa | actggtggct | acaatgcctt | tatttgctaa | tgcggatcct | 1080 |
| aattttgtga | ctgccatgct | gagcaagttg | agatttgagg | tgtttcaacc | tggagattat | 1140 |
| atcatacgag | aaggagccgt | gggtaaaaaa | atgtatttca | ttcaacacgg | tgttgctggt | 1200 |
| gtcattacaa | aatccagtaa | agaaatgaag | ctgacagatg | gctcttactt | tggagagatt | 1260 |
| tgcctgctga | ccaaaggacg | tcgtactgcc | agtgttcgag | ctgatacata | ttgtcgtctt | 1320 |
| tactcacttt | ccgtggacaa | tttcaacgag | gtcctggagg | aatatccaat | gatgaggaga | 1380 |
| gcctttgaga | cagttgccat | tgaccgacta | gatcgaatag | gaaagaaaaa | ttcaattctt | 1440 |
| ctgcaaaagt | tccagaagga | tctgaacact | ggtgtttttca | acaatcagga | gaacgaaatc | 1500 |
| ctcaagcaga | ttgtgaaaca | tgacagggag | atggtgcagg | caatcgctcc | catcaattat | 1560 |
| cctcaaatga | caaccctgaa | ttccacatcg | tctactacga | cccgacctc | ccgcatgagg | 1620 |
| acacaatctc | caccggtgta | cacagcgacc | agcctgtctc | acagcaacct | gcactccccc | 1680 |
| agtcccagca | cacagacccc | ccagccatca | gccatcctgt | caccctgctc | ctacaccacc | 1740 |
| gcggtctgca | gccctcctgt | acagagccct | ctggccgctc | gaacttttcca | ctatgcctcc | 1800 |
| cccaccgcct | cccagctgtc | actcatgcaa | cagcagccgc | agcagcaggt | acagcagtcc | 1860 |

-continued

```
cagccgccgc agactcagcc acagcagccg tccccgcagc cacagacacc tggcagctcc    1920
acgccgaaaa atgaagtgca caagagcacg caggcgcttc acaacaccaa cctgacccgg    1980
gaagtcaggc cattttccgc ctggcagcct cgctgcccca tgaggtgtcc attttgattt    2040
ccagacctca tcccactgtg ggggagtccc tggcctccat ccctcaaccc gtgacggcgg    2100
tccccggaac gggccttcag gcaggggggca ggagcactgt cccgcagcgc gtcacctttt    2160
tccgacagat gtgtcgggag ccatccccc gaaccgagga gtccttccag caccccttcc    2220
acttatcaca ccccatccta aaaaaaaaaa aaaaaaaaaa aaa                       2263
```

<210> SEQ ID NO 10
<211> LENGTH: 749
<212> TYPE: PRT
<213> ORGANISM: human
<300> PUBLICATION INFORMATION:
<308> DATABASE ACCESSION NUMBER: AAC39759
<309> DATABASE ENTRY DATE: 1998-05-29
<313> RELEVANT RESIDUES: (1)..(749)

<400> SEQUENCE: 10

```
Lys Glu Gln Glu Arg Val Lys Thr Ala Gly Phe Trp Ile Ile His Pro
1               5                   10                  15
Tyr Ser Asp Phe Arg Phe Tyr Trp Asp Leu Ile Met Leu Ile Met Met
            20                  25                  30
Val Gly Asn Leu Val Ile Ile Pro Val Gly Ile Thr Phe Phe Thr Glu
        35                  40                  45
Gln Thr Thr Thr Pro Trp Ile Ile Phe Asn Val Ala Ser Asp Thr Val
    50                  55                  60
Phe Leu Leu Asp Leu Ile Met Asn Phe Arg Thr Gly Thr Val Asn Glu
65                  70                  75                  80
Asp Ser Ser Glu Ile Ile Leu Asp Pro Lys Val Ile Lys Met Asn Tyr
                85                  90                  95
Leu Lys Ser Trp Phe Val Val Asp Phe Ile Ser Ser Ile Pro Val Asp
            100                 105                 110
Tyr Ile Phe Leu Ile Val Glu Lys Gly Met Asp Ser Glu Val Tyr Lys
        115                 120                 125
Thr Ala Arg Ala Leu Arg Ile Val Arg Phe Thr Lys Ile Leu Ser Leu
    130                 135                 140
Leu Arg Leu Leu Arg Leu Ser Arg Leu Ile Arg Tyr Ile His Gln Trp
145                 150                 155                 160
Glu Glu Ile Phe His Met Thr Tyr Asp Leu Ala Ser Ala Val Val Arg
                165                 170                 175
Ile Phe Asn Leu Ile Gly Met Met Leu Leu Leu Cys His Trp Asp Gly
            180                 185                 190
Cys Leu Gln Phe Leu Val Pro Leu Leu Gln Asp Phe Pro Pro Asp Cys
        195                 200                 205
Trp Val Ser Leu Asn Glu Met Val Asn Asp Ser Trp Gly Lys Gln Tyr
    210                 215                 220
Ser Tyr Ala Leu Phe Lys Ala Met Ser His Met Leu Cys Ile Gly Tyr
225                 230                 235                 240
Gly Ala Gln Ala Pro Val Ser Met Ser Asp Leu Trp Ile Thr Met Leu
                245                 250                 255
Ser Met Ile Val Gly Ala Thr Cys Tyr Ala Met Phe Val Gly His Ala
            260                 265                 270
Thr Ala Leu Ile Gln Ser Leu Asp Ser Ser Arg Arg Gln Tyr Gln Glu
```

```
                275                 280                 285
Lys Tyr Lys Gln Val Glu Gln Tyr Met Ser Phe His Lys Leu Pro Ala
    290                 295                 300

Asp Met Arg Gln Lys Ile His Asp Tyr Tyr Glu His Arg Tyr Gln Gly
305                 310                 315                 320

Lys Ile Phe Asp Glu Glu Asn Ile Leu Asn Glu Leu Asn Asp Pro Leu
                325                 330                 335

Arg Glu Glu Ile Val Asn Phe Asn Cys Arg Lys Leu Val Ala Thr Met
            340                 345                 350

Pro Leu Phe Ala Asn Ala Asp Pro Asn Phe Val Thr Ala Met Leu Ser
        355                 360                 365

Lys Leu Arg Phe Glu Val Phe Gln Pro Gly Asp Tyr Ile Ile Arg Glu
    370                 375                 380

Gly Ala Val Gly Lys Lys Met Tyr Phe Ile Gln His Gly Val Ala Gly
385                 390                 395                 400

Val Ile Thr Lys Ser Ser Lys Glu Met Lys Leu Thr Asp Gly Ser Tyr
                405                 410                 415

Phe Gly Glu Ile Cys Leu Leu Thr Lys Gly Arg Arg Thr Ala Ser Val
            420                 425                 430

Arg Ala Asp Thr Tyr Cys Arg Leu Tyr Ser Leu Ser Val Asp Asn Phe
        435                 440                 445

Asn Glu Val Leu Glu Glu Tyr Pro Met Met Arg Arg Ala Phe Glu Thr
    450                 455                 460

Val Ala Ile Asp Arg Leu Asp Arg Ile Gly Lys Lys Asn Ser Ile Leu
465                 470                 475                 480

Leu Gln Lys Phe Gln Lys Asp Leu Asn Thr Gly Val Phe Asn Asn Gln
                485                 490                 495

Glu Asn Glu Ile Leu Lys Gln Ile Val Lys His Asp Arg Glu Met Val
            500                 505                 510

Gln Ala Ile Ala Pro Ile Asn Tyr Pro Gln Met Thr Thr Leu Asn Ser
        515                 520                 525

Thr Ser Ser Thr Thr Thr Pro Thr Ser Arg Met Arg Thr Gln Ser Pro
    530                 535                 540

Pro Val Tyr Thr Ala Thr Ser Leu Ser His Ser Asn Leu His Ser Pro
545                 550                 555                 560

Ser Pro Ser Thr Gln Thr Pro Gln Pro Ser Ala Ile Leu Ser Pro Cys
                565                 570                 575

Ser Tyr Thr Thr Ala Val Cys Ser Pro Pro Val Gln Ser Pro Leu Ala
            580                 585                 590

Ala Arg Thr Phe His Tyr Ala Ser Pro Thr Ala Ser Gln Leu Ser Leu
        595                 600                 605

Met Gln Gln Gln Pro Gln Gln Val Gln Gln Ser Gln Pro Pro Gln
    610                 615                 620

Thr Gln Pro Gln Gln Pro Ser Pro Gln Pro Thr Pro Gly Ser Ser
625                 630                 635                 640

Thr Pro Lys Asn Glu Val His Lys Ser Thr Gln Ala Leu His Asn Thr
                645                 650                 655

Asn Leu Thr Arg Glu Val Arg Pro Phe Ser Ala Trp Gln Pro Ser Leu
            660                 665                 670

Pro His Glu Val Ser Ile Leu Ile Ser Arg Pro His Pro Thr Val Gly
        675                 680                 685

Glu Ser Leu Ala Ser Ile Pro Gln Pro Val Thr Ala Val Pro Gly Thr
    690                 695                 700
```

```
Gly Leu Gln Ala Gly Gly Arg Ser Thr Val Pro Gln Arg Val Thr Phe
705                 710                 715                 720

Phe Arg Gln Met Ser Ser Gly Ala Ile Pro Pro Asn Arg Gly Val Leu
                725                 730                 735

Pro Ala Pro Leu Pro Leu Ile Thr Pro His Pro Lys Lys
            740                 745

<210> SEQ ID NO 11
<211> LENGTH: 1790
<212> TYPE: DNA
<213> ORGANISM: human;

<400> SEQUENCE: 11
gcgaggaggc gggcccggcg ggggagccgc gcggcagcca ggccagcttc atgcagcgcc      60
agttcggcgc gctcctgcag ccgggcgtca acaagttctc gctgcggatg ttcggcagcc     120
agaaggccgt ggagcgcgag caggagcgcg tcaagtcggc gggggcctgg atcatccacc     180
cgtacagcga cttcaggttc tactgggact tcaccatgct gctgttcatg gtgggaaacc     240
tcatcatcat cccagtgggc atcaccttct tcaaggatga gaccactgcc ccgtggatcg     300
tgttcaacgt ggtctcggac accttcttcc tcatggacct ggtgttgaac ttccgcaccg     360
gcattgtgat cgaggacaac acggagatca tcctggaccc cgagaagatc aagaaaagta     420
tctgcgcacg tggttcgtgg tggtcttcgt gtcctccatc ccgtggact acatcttcct      480
tatcgtggag aagggcattg actccgaggt ctacaagacg gcacgcgccc tgcgcatcgt     540
gcgcttcacc aaaatcctca gcctcctgcg gctgctgcgc ctctcacgcc tgatccgcta     600
catccatcag tgggaggaga tcttccacat gacctatgac ctggccagcg cggtgatgag     660
gatctgcaat ctcatcagca tgatgctgct gctctgccac tgggacggct gcctgcagtt     720
cctggtgcct atgctgcagg acttcccgcg caactgctgg gtgtccatca atggcatggt     780
gaaccactcg tggagtgaac tgtactcctt cgcactcttc aaggccatga gccacatgct     840
gtgcatcggg tacggccggc aggcgcccga agcatgacg gacatctggc tgaccatgct      900
cagcatgatt gtgggtgcca cctgctacgc catgttcatc ggccacgcca ctgccctcat     960
ccagtcgctg gactcctcgc ggcgccagta ccaggagaag tacaagcagg tggagcagta    1020
catgtccttc cacaagctgc cagctgactt ccgccagaag atccacgact actatgaaca    1080
ccgttaccag ggcaagatgt ttgacgagga cagcatcctg ggcgagctca cgggcccct     1140
gcgggaggag atcgtcaact tcaactgccg gaagctggtg gcctccatgc cgctgttcgc    1200
caacgccgac cccaacttcg tcacggccat gctgaccaag ctcaagttcg aggtcttcca    1260
gccgggtgac tacatcatcc gcgaaagcac catcggaag aagatgtact tcatccagca    1320
cggcgtggtc agcgtgctca ctaagggcaa caaggagatg aagctgtccg atggctccta    1380
cttcggggag atctgcctgc tcacccgggg ccgccgcacg gcgacgtgcg ggctgacacc    1440
tactgccgcc tctattccct gagcgtggac aacttcaacg aagtgctgga ggagtacccc    1500
atgatgcggc gcgctttcga gacggtggcc atcgaccgcc tggaccgcat cggcaagaag    1560
aattccatcc tcctgcacaa ggtgcagcat gacctcaact cggcgtatt caacaaccag     1620
gagaacgcca tcatccagga gatcgtcaag tacgaccgcg agatggtgca gcaggccgag    1680
ctgggtcagc gcgtgggctt tttccgccg ccgccgccgc cgccgcaggt cacttcggcc     1740
atcgccacgc tgcagcaggc ggcggccatg agcttctgcc cgcaggtggc                1790
```

-continued

```
<210> SEQ ID NO 12
<211> LENGTH: 597
<212> TYPE: PRT
<213> ORGANISM: human;
<300> PUBLICATION INFORMATION:
<308> DATABASE ACCESSION NUMBER: AAC39760
<309> DATABASE ENTRY DATE: 1998-05-29
<313> RELEVANT RESIDUES: (1)..(597)

<400> SEQUENCE: 12

Glu Glu Ala Gly Pro Ala Gly Glu Pro Arg Gly Ser Gln Ala Ser Phe
1               5                   10                  15

Met Gln Arg Gln Phe Gly Ala Leu Leu Gln Pro Gly Val Asn Lys Phe
            20                  25                  30

Ser Leu Arg Met Phe Gly Ser Gln Lys Ala Val Glu Arg Glu Gln Glu
        35                  40                  45

Arg Val Lys Ser Ala Gly Ala Trp Ile Ile His Pro Tyr Ser Asp Phe
    50                  55                  60

Arg Phe Tyr Trp Asp Phe Thr Met Leu Leu Phe Met Val Gly Asn Leu
65                  70                  75                  80

Ile Ile Ile Pro Val Gly Ile Thr Phe Phe Lys Asp Glu Thr Thr Ala
                85                  90                  95

Pro Trp Ile Val Phe Asn Val Val Ser Asp Thr Phe Phe Leu Met Asp
            100                 105                 110

Leu Val Leu Asn Phe Arg Thr Gly Ile Val Ile Glu Asp Asn Thr Glu
        115                 120                 125

Ile Ile Leu Asp Pro Glu Lys Ile Lys Lys Lys Tyr Leu Arg Thr Trp
    130                 135                 140

Phe Val Val Phe Val Ser Ser Ile Pro Val Asp Tyr Ile Phe Leu
145                 150                 155                 160

Ile Val Glu Lys Gly Ile Asp Ser Glu Val Tyr Lys Thr Ala Arg Ala
                165                 170                 175

Leu Arg Ile Val Arg Phe Thr Lys Ile Leu Ser Leu Leu Arg Leu Leu
            180                 185                 190

Arg Leu Ser Arg Leu Ile Arg Tyr Ile His Gln Trp Glu Glu Ile Phe
        195                 200                 205

His Met Thr Tyr Asp Leu Ala Ser Ala Val Met Arg Ile Cys Asn Leu
    210                 215                 220

Ile Ser Met Met Leu Leu Leu Cys His Trp Asp Gly Cys Leu Gln Phe
225                 230                 235                 240

Leu Val Pro Met Leu Gln Asp Phe Pro Arg Asn Cys Trp Val Ser Ile
                245                 250                 255

Asn Gly Met Val Asn His Ser Trp Ser Glu Leu Tyr Ser Phe Ala Leu
            260                 265                 270

Phe Lys Ala Met Ser His Met Leu Cys Ile Gly Tyr Gly Arg Gln Ala
        275                 280                 285

Pro Glu Ser Met Thr Asp Ile Trp Leu Thr Met Leu Ser Met Ile Val
    290                 295                 300

Gly Ala Thr Cys Tyr Ala Met Phe Ile Gly His Ala Thr Ala Leu Ile
305                 310                 315                 320

Gln Ser Leu Asp Ser Ser Arg Arg Gln Tyr Gln Glu Lys Tyr Lys Gln
                325                 330                 335

Val Glu Gln Tyr Met Ser Phe His Lys Leu Pro Ala Asp Phe Arg Gln
            340                 345                 350

Lys Ile His Asp Tyr Tyr Glu His Arg Tyr Gln Gly Lys Met Phe Asp
        355                 360                 365
```

```
Glu Asp Ser Ile Leu Gly Glu Leu Asn Gly Pro Leu Arg Glu Ile
    370                 375                 380

Val Asn Phe Asn Cys Arg Lys Leu Val Ala Ser Met Pro Leu Phe Ala
385                 390                 395                 400

Asn Ala Asp Pro Asn Phe Val Thr Ala Met Leu Thr Lys Leu Lys Phe
                405                 410                 415

Glu Val Phe Gln Pro Gly Asp Tyr Ile Ile Arg Glu Ser Thr Ile Gly
            420                 425                 430

Lys Lys Met Tyr Phe Ile Gln His Gly Val Val Ser Val Leu Thr Lys
        435                 440                 445

Gly Asn Lys Glu Met Lys Leu Ser Asp Gly Ser Tyr Phe Gly Glu Ile
    450                 455                 460

Cys Leu Leu Thr Arg Gly Arg Arg Thr Ala Ser Val Arg Ala Asp Thr
465                 470                 475                 480

Tyr Cys Arg Leu Tyr Ser Leu Ser Val Asp Asn Phe Asn Glu Val Leu
                485                 490                 495

Glu Glu Tyr Pro Met Met Arg Arg Ala Phe Glu Thr Val Ala Ile Asp
            500                 505                 510

Arg Leu Asp Arg Ile Gly Lys Lys Asn Ser Ile Leu Leu His Lys Val
        515                 520                 525

Gln His Asp Leu Asn Ser Gly Val Phe Asn Asn Gln Glu Asn Ala Ile
    530                 535                 540

Ile Gln Glu Ile Val Lys Tyr Asp Arg Glu Met Val Gln Gln Ala Glu
545                 550                 555                 560

Leu Gly Gln Arg Val Gly Phe Phe Pro Pro Pro Pro Pro Pro Pro Gln
                565                 570                 575

Val Thr Ser Ala Ile Ala Thr Leu Gln Gln Ala Ala Ala Met Ser Phe
            580                 585                 590

Cys Pro Gln Val Ala
        595

<210> SEQ ID NO 13
<211> LENGTH: 25
<212> TYPE: DNA
<213> ORGANISM: mouse;

<400> SEQUENCE: 13
agaggcatag tagccaccag tttcc                                      25

<210> SEQ ID NO 14
<211> LENGTH: 31
<212> TYPE: DNA
<213> ORGANISM: mouse;

<400> SEQUENCE: 14
ccgctcgagg ccttggtatc ggtgctcata g                               31

<210> SEQ ID NO 15
<211> LENGTH: 25
<212> TYPE: DNA
<213> ORGANISM: mouse;

<400> SEQUENCE: 15
gaagcggatg ttaacgatac cagcc                                      25

<210> SEQ ID NO 16
<211> LENGTH: 25
```

-continued

```
<212> TYPE: DNA
<213> ORGANISM: mouse;

<400> SEQUENCE: 16
gacaagccga caaccttgat tggag                                          25

<210> SEQ ID NO 17
<211> LENGTH: 25
<212> TYPE: DNA
<213> ORGANISM: mouse;

<400> SEQUENCE: 17
gagcaagttc agcctggtta agtcc                                          25

<210> SEQ ID NO 18
<211> LENGTH: 26
<212> TYPE: DNA
<213> ORGANISM: mouse;

<400> SEQUENCE: 18
gtggcttatg agtatttctt ccaggg                                         26

<210> SEQ ID NO 19
<211> LENGTH: 24
<212> TYPE: DNA
<213> ORGANISM: mouse;

<400> SEQUENCE: 19
tgggaagaga tattccacat gacc                                           24

<210> SEQ ID NO 20
<211> LENGTH: 27
<212> TYPE: DNA
<213> ORGANISM: mouse;

<400> SEQUENCE: 20
tacgacctgg caagtgcagt gatgcgc                                        27

<210> SEQ ID NO 21
<211> LENGTH: 28
<212> TYPE: DNA
<213> ORGANISM: mouse;

<400> SEQUENCE: 21
agttcacaat ctcctcacgc agtggccc                                       28

<210> SEQ ID NO 22
<211> LENGTH: 24
<212> TYPE: DNA
<213> ORGANISM: mouse;

<400> SEQUENCE: 22
ctggtggata tatcggatga gccg                                           24

<210> SEQ ID NO 23
<211> LENGTH: 27
<212> TYPE: DNA
<213> ORGANISM: mouse;

<400> SEQUENCE: 23
cagtgggaag agattttcca catgacc                                        27

<210> SEQ ID NO 24
```

-continued

```
<211> LENGTH: 26
<212> TYPE: DNA
<213> ORGANISM: mouse;

<400> SEQUENCE: 24
gatcatgctg aaccttgtgc agcaag                                              26

<210> SEQ ID NO 25
<211> LENGTH: 22
<212> TYPE: DNA
<213> ORGANISM: mouse;

<400> SEQUENCE: 25 caccettgaa gtggtccacg ct                                                  22

<210> SEQ ID NO 26
<211> LENGTH: 26
<212> TYPE: DNA
<213> ORGANISM: mouse;

<400> SEQUENCE: 26
atgttcggag ccagaaggcg gtggag                                              26

<210> SEQ ID NO 27
<211> LENGTH: 24
<212> TYPE: DNA
<213> ORGANISM: mouse;

<400> SEQUENCE: 27
cagctcgaac actggcagta cgac                                                24

<210> SEQ ID NO 28
<211> LENGTH: 24
<212> TYPE: DNA
<213> ORGANISM: human;

<400> SEQUENCE: 28
aacttcaact gccggaagct ggtg                                                24

<210> SEQ ID NO 29
<211> LENGTH: 24
<212> TYPE: DNA
<213> ORGANISM: human;

<400> SEQUENCE: 29
gaaaaagccc acgcgctgac ccag                                                24

<210> SEQ ID NO 30
<211> LENGTH: 25
<212> TYPE: DNA
<213> ORGANISM: human;

<400> SEQUENCE: 30
caccagcttc cggcagttga agttg                                               25

<210> SEQ ID NO 31
<211> LENGTH: 28
<212> TYPE: DNA
<213> ORGANISM: mouse;

<400> SEQUENCE: 31
gcgaattcaa acccaactcc gcgtccaa                                            28
```

```
<210> SEQ ID NO 32
<211> LENGTH: 24
<212> TYPE: DNA
<213> ORGANISM: mouse;

<400> SEQUENCE: 32
cctgaattca ctgtacggat ggat                                        24

<210> SEQ ID NO 33
<211> LENGTH: 24
<212> TYPE: DNA
<213> ORGANISM: human;

<400> SEQUENCE: 33
gtcgtactgc cagtgttcga gctg                                        24

<210> SEQ ID NO 34
<211> LENGTH: 24
<212> TYPE: DNA
<213> ORGANISM: human;

<400> SEQUENCE: 34
ggtcaggttg gtgttgtgaa acgc                                        24

<210> SEQ ID NO 35
<211> LENGTH: 25
<212> TYPE: PRT
<213> ORGANISM: mouse;

<400> SEQUENCE: 35

Tyr Ser Tyr Ala Leu Phe Lys Ala Met Ser His Met Leu Cys Ile Gly
1               5                  10                  15

Tyr Gly Ala Gln Ala Pro Val Ser Met
            20                  25

<210> SEQ ID NO 36
<211> LENGTH: 25
<212> TYPE: PRT
<213> ORGANISM: Drosophila;

<400> SEQUENCE: 36

Ile Pro Asp Ala Phe Trp Trp Ala Val Val Thr Met Thr Thr Val Gly
1               5                  10                  15

Tyr Gly Asp Met Thr Pro Val Gly Val
            20                  25

<210> SEQ ID NO 37
<211> LENGTH: 25
<212> TYPE: PRT
<213> ORGANISM: Drosophila;

<400> SEQUENCE: 37

Ile Pro Leu Gly Leu Trp Trp Ala Leu Val Thr Met Thr Thr Val Gly
1               5                  10                  15

Tyr Gly Asp Met Ala Pro Lys Thr Tyr
            20                  25

<210> SEQ ID NO 38
<211> LENGTH: 25
<212> TYPE: PRT
<213> ORGANISM: mouse;

<400> SEQUENCE: 38
```

-continued

Tyr Trp Thr Cys Val Tyr Phe Leu Ile Val Thr Met Ser Thr Val Gly
1               5                   10                  15

Tyr Gly Asp Val Tyr Cys Glu Thr Val
            20              25

<210> SEQ ID NO 39
<211> LENGTH: 25
<212> TYPE: PRT
<213> ORGANISM: plant;

<400> SEQUENCE: 39

Tyr Val Thr Ser Met Tyr Trp Ser Ile Thr Thr Leu Thr Val Gly
1               5                   10                  15

Tyr Gly Asp Leu His Pro Val Asn Thr
            20              25

<210> SEQ ID NO 40
<211> LENGTH: 25
<212> TYPE: PRT
<213> ORGANISM: Drosophila;

<400> SEQUENCE: 40

Tyr Val Thr Ala Leu Tyr Phe Thr Met Thr Cys Met Thr Ser Val Gly
1               5                   10                  15

Phe Gly Asn Val Ala Ala Glu Thr Asp
            20              25

<210> SEQ ID NO 41
<211> LENGTH: 25
<212> TYPE: PRT
<213> ORGANISM: mouse;

<400> SEQUENCE: 41

Tyr Ile Ser Ser Leu Tyr Phe Thr Met Tyr Ser Leu Thr Ser Val Gly
1               5                   10                  15

Phe Gly Asn Ile Ala Pro Ser Thr Asp
            20              25

<210> SEQ ID NO 42
<211> LENGTH: 25
<212> TYPE: PRT
<213> ORGANISM: human;

<400> SEQUENCE: 42

Tyr Val Thr Ala Leu Tyr Phe Thr Phe Ser Ser Leu Tyr Ser Val Gly
1               5                   10                  15

Phe Gly Asn Val Ser Pro Asn Thr Asn
            20              25

<210> SEQ ID NO 43
<211> LENGTH: 23
<212> TYPE: PRT
<213> ORGANISM: bovine;
<220> FEATURE:
<221> NAME/KEY: NON_CONS
<222> LOCATION: (16)..(17)
<223> OTHER INFORMATION: gapped alignment

<400> SEQUENCE: 43

Tyr Val Tyr Ser Leu Tyr Trp Ser Thr Leu Thr Leu Thr Thr Ile Gly
1               5                   10                  15

Glu Thr Pro Pro Pro Val Arg
            20

-continued

```
<210> SEQ ID NO 44
<211> LENGTH: 24
<212> TYPE: PRT
<213> ORGANISM: human;
<220> FEATURE:
<221> NAME/KEY: NON_CONS
<222> LOCATION: (16)..(17)
<223> OTHER INFORMATION: gapped alignment

<400> SEQUENCE: 44

Tyr Ile Arg Cys Tyr Tyr Phe Ala Val Lys Thr Leu Ile Thr Ile Gly
1               5                   10                  15

Gly Leu Pro Asp Pro Lys Thr Leu
            20

<210> SEQ ID NO 45
<211> LENGTH: 131
<212> TYPE: PRT
<213> ORGANISM: mouse;
<220> FEATURE:
<221> NAME/KEY: NON_CONS
<222> LOCATION: (48)..(49)
<223> OTHER INFORMATION: gap in alignment
<220> FEATURE:
<221> NAME/KEY: NON_CONS
<222> LOCATION: (63)..(64)
<223> OTHER INFORMATION: gap in alignment
<220> FEATURE:
<221> NAME/KEY: NON_CONS
<222> LOCATION: (65)..(66)
<223> OTHER INFORMATION: gap in alignment

<400> SEQUENCE: 45

Phe Val Thr Ala Met Leu Ser Lys Leu Arg Phe Glu Val Phe Gln Pro
1               5                   10                  15

Gly Asp Tyr Ile Ile Arg Glu Gly Ala Val Gly Lys Lys Met Tyr Phe
            20                  25                  30
Ile Gln His Gly Val Ala Gly Val Ile Thr Lys Ser Ser Lys Glu Met
        35                  40                  45

Lys Leu Thr Asp Gly Ser Tyr Phe Gly Glu Ile Cys Leu Leu Thr Lys
    50                  55                  60

Gly Arg Arg Thr Ala Ser Val Arg Ala Asp Thr Tyr Cys Arg Leu Tyr
65                  70                  75                  80

Ser Leu Ser Val Asp Asn Phe Asn Glu Val Leu Glu Glu Tyr Pro Met
                85                  90                  95

Met Arg Arg Ala Phe Glu Thr Val Ala Ile Asp Arg Leu Asp Arg Ile
            100                 105                 110

Gly Lys Lys Asn Ser Ile Leu Leu Gln Lys Phe Gln Lys Asp Leu Asn
        115                 120                 125

Thr Gly Val
    130

<210> SEQ ID NO 46
<211> LENGTH: 129
<212> TYPE: PRT
<213> ORGANISM: rat;
<220> FEATURE:
<221> NAME/KEY: NON_CONS
<222> LOCATION: (48)..(49)
<223> OTHER INFORMATION: gap in alignment
<220> FEATURE:
<221> NAME/KEY: NON_CONS
<222> LOCATION: (121)..(122)
<223> OTHER INFORMATION: gap in alignment
<220> FEATURE:
```

```
<221> NAME/KEY: NON_CONS
<222> LOCATION: (125)..(126)
<223> OTHER INFORMATION: gap in alignment

<400> SEQUENCE: 46
```

| | | | | | | | | | | | | | | | |
|---|---|---|---|---|---|---|---|---|---|---|---|---|---|---|---|
| Leu | Leu | Val | Glu | Leu | Val | Leu | Lys | Leu | Arg | Pro | Gln | Val | Phe | Ser | Pro |
| 1 | | | | 5 | | | | | 10 | | | | | 15 | |
| Gly | Asp | Tyr | Ile | Cys | Arg | Lys | Gly | Asp | Ile | Gly | Lys | Glu | Met | Tyr | Ile |
| | | | 20 | | | | | 25 | | | | | 30 | | |
| Ile | Lys | Glu | Gly | Lys | Leu | Ala | Val | Val | Ala | Asp | Asp | Gly | Val | Thr | Gln |
| | | | 35 | | | | | 40 | | | | | 45 | | |
| Tyr | Ala | Leu | Leu | Ser | Ala | Gly | Ser | Cys | Phe | Gly | Glu | Ile | Ser | Ile | Leu |
| 50 | | | | | 55 | | | | | 60 | | | | | |
| Asn | Ile | Lys | Gly | Ser | Lys | Met | Gly | Asn | Arg | Arg | Thr | Ala | Asn | Ile | Arg |
| 65 | | | | | 70 | | | | | 75 | | | | | 80 |
| Ser | Leu | Gly | Tyr | Ser | Asp | Leu | Phe | Cys | Leu | Ser | Lys | Asp | Asp | Leu | Met |
| | | | | 85 | | | | | 90 | | | | | 95 | |
| Glu | Ala | Val | Thr | Glu | Tyr | Pro | Asp | Ala | Lys | Lys | Val | Leu | Glu | Glu | Arg |
| | | | | 100 | | | | | 105 | | | | | 110 | |
| Gly | Arg | Glu | Ile | Leu | Met | Lys | Glu | Gly | Leu | Leu | Asp | Glu | Asn | Glu | Val |
| | | | 115 | | | | | 120 | | | | | 125 | | |
| Ala | | | | | | | | | | | | | | | |

```
<210> SEQ ID NO 47
<211> LENGTH: 126
<212> TYPE: PRT
<213> ORGANISM: bovine;
<220> FEATURE:
<221> NAME/KEY: NON_CONS
<222> LOCATION: (69)..(70)
<223> OTHER INFORMATION: gap in alignment
<220> FEATURE:
<221> NAME/KEY: NON_CONS
<222> LOCATION: (82)..(83)
<223> OTHER INFORMATION: gap in alignment
<220> FEATURE:
<221> NAME/KEY: NON_CONS
<222> LOCATION: (91)..(92)
<223> OTHER INFORMATION: gap in alignment
<220> FEATURE:
<221> NAME/KEY: NON_CONS
<222> LOCATION: (116)..(117)
<223> OTHER INFORMATION: gap in alignment

<400> SEQUENCE: 47
```

| | | | | | | | | | | | | | | | |
|---|---|---|---|---|---|---|---|---|---|---|---|---|---|---|---|
| Ile | Leu | Ser | Lys | Leu | Ala | Asp | Val | Leu | Glu | Glu | Thr | His | Tyr | Glu | Asn |
| 1 | | | | 5 | | | | | 10 | | | | | 15 | |
| Gly | Glu | Tyr | Ile | Ile | Arg | Gln | Gly | Ala | Ala | Arg | Gly | Asp | Thr | Phe | Phe |
| | | | 20 | | | | | 25 | | | | | 30 | | |
| Ile | Ile | Ser | Lys | Gly | Lys | Val | Asn | Val | Thr | Arg | Glu | Asp | Ser | Pro | Asn |
| | | | 35 | | | | | 40 | | | | | 45 | | |
| Glu | Asp | Pro | Val | Phe | Leu | Arg | Thr | Leu | Gly | Lys | Gly | Asp | Trp | Phe | Gly |
| 50 | | | | | 55 | | | | | 60 | | | | | |
| Glu | Lys | Ala | Leu | Gln | Gly | Glu | Asp | Val | Arg | Thr | Ala | Asn | Val | Ile | Ala |
| 65 | | | | | 70 | | | | | 75 | | | | | 80 |
| Ala | Glu | Ala | Val | Thr | Cys | Leu | Val | Ile | Asp | Arg | Asp | Ser | Phe | Lys | His |
| | | | | 85 | | | | | 90 | | | | | 95 | |
| Leu | Ile | Gly | Gly | Leu | Asp | Asp | Val | Ser | Asn | Lys | Ala | Tyr | Glu | Asp | Ala |
| | | | | 100 | | | | | 105 | | | | | 110 | |
| Glu | Ala | Lys | Ala | Lys | Tyr | Glu | Ala | Glu | Ala | Phe | Phe | Ala | | | |
| | | | 115 | | | | | 120 | | | | | 125 | | |

<210> SEQ ID NO 48
<211> LENGTH: 119
<212> TYPE: PRT
<213> ORGANISM: bovine;
<220> FEATURE:
<221> NAME/KEY: NON_CONS
<222> LOCATION: (68)..(69)
<223> OTHER INFORMATION: gap in alignment
<220> FEATURE:
<221> NAME/KEY: NON_CONS
<222> LOCATION: (81)..(82)
<223> OTHER INFORMATION: gap in alignment
<220> FEATURE:
<221> NAME/KEY: NON_CONS
<222> LOCATION: (90)..(91)
<223> OTHER INFORMATION: gap in alignment
<220> FEATURE:
<221> NAME/KEY: NON_CONS
<222> LOCATION: (110)..(111)
<223> OTHER INFORMATION: gap in alignment

<400> SEQUENCE: 48

Glu Arg Leu Thr Val Ala Asp Ala Leu Glu Pro Val Gln Phe Glu Asp
1               5                   10                  15

Gly Gln Lys Ile Val Val Gln Gly Glu Pro Gly Asp Glu Phe Phe Ile
                20                  25                  30

Ile Leu Glu Gly Ser Ala Ala Val Leu Gln Arg Arg Ser Glu Asn Glu
            35                  40                  45

Glu Phe Val Glu Val Gly Arg Leu Gly Pro Ser Asp Tyr Phe Gly Glu
        50                  55                  60

Ile Ala Leu Leu Met Asn Arg Pro Arg Ala Ala Thr Val Val Ala Arg
65                  70                  75                  80

Gly Pro Leu Lys Cys Val Lys Leu Asp Arg Pro Arg Phe Glu Arg Val
                85                  90                  95

Leu Gly Pro Cys Ser Asp Ile Leu Lys Arg Asn Ile Gln Gln Tyr Asn
            100                 105                 110

Ser Phe Val Ser Leu Ser Val
        115

<210> SEQ ID NO 49
<211> LENGTH: 124
<212> TYPE: PRT
<213> ORGANISM: E. coli;
<220> FEATURE:
<221> NAME/KEY: NON_CONS
<222> LOCATION: (48)..(49)
<223> OTHER INFORMATION: gap in alignment
<220> FEATURE:
<221> NAME/KEY: NON_CONS
<222> LOCATION: (67)..(68)
<223> OTHER INFORMATION: gap in alignment

<400> SEQUENCE: 49

Thr Leu Glu Trp Phe Leu Ser His Cys His Ile His Lys Tyr Pro Ser
1               5                   10                  15

Lys Ser Thr Leu Ile His Gln Gly Glu Lys Ala Glu Thr Leu Tyr Tyr
                20                  25                  30

Ile Val Lys Gly Ser Val Ala Val Leu Ile Lys Glu Glu Gly Lys Glu
            35                  40                  45

Met Ile Leu Ser Tyr Leu Asn Gln Gly Asp Phe Ile Gly Glu Leu Gly
        50                  55                  60

Leu Phe Glu Glu Gly Gln Glu Arg Ser Ala Trp Val Arg Ala Lys Thr
65                  70                  75                  80

```
Ala Cys Glu Val Ala Glu Ile Ser Tyr Lys Lys Phe Arg Gln Leu Ile
                85                  90                  95

Gln Val Asn Pro Asp Ile Leu Met Arg Leu Ser Ala Gln Met Ala Arg
            100                 105                 110

Arg Leu Gln Val Thr Ser Glu Lys Val Gly Asn Leu
        115                 120
```

```
<210> SEQ ID NO 50
<211> LENGTH: 33
<212> TYPE: PRT
<213> ORGANISM: mouse;

<400> SEQUENCE: 50
```

```
Lys Thr Ala Arg Ala Leu Arg Ile Val Arg Phe Thr Lys Ile Leu Ser
1               5                   10                  15

Leu Leu Arg Leu Leu Arg Leu Ser Arg Leu Ile Arg Tyr Ile His Gln
            20                  25                  30

Trp
```

```
<210> SEQ ID NO 51
<211> LENGTH: 33
<212> TYPE: PRT
<213> ORGANISM: Drosophila;

<400> SEQUENCE: 51
```

```
Asn Gln Ala Met Ser Leu Ala Ile Leu Arg Val Ile Arg Leu Val Arg
1               5                   10                  15

Val Phe Arg Ile Phe Lys Leu Ser Arg His Ser Lys Gly Leu Gln Ile
            20                  25                  30

Leu
```

```
<210> SEQ ID NO 52
<211> LENGTH: 33
<212> TYPE: PRT
<213> ORGANISM: bovine;

<400> SEQUENCE: 52
```

```
Lys Phe Gly Trp Asn Tyr Pro Glu Ile Arg Leu Asn Arg Leu Leu Arg
1               5                   10                  15

Ile Ser Arg Met Phe Glu Phe Phe Gln Arg Thr Glu Thr Arg Thr Asn
            20                  25                  30

Ile
```

```
<210> SEQ ID NO 53
<211> LENGTH: 119
<212> TYPE: PRT
<213> ORGANISM: mouse;
<220> FEATURE:
<221> NAME/KEY: NON_CONS
<222> LOCATION: (47)..(48)
<223> OTHER INFORMATION: gap in alignment
<220> FEATURE:
<221> NAME/KEY: NON_CONS
<222> LOCATION: (55)..(56)
<223> OTHER INFORMATION: gap in alignment
<220> FEATURE:
<221> NAME/KEY: NON_CONS
<222> LOCATION: (65)..(66)
<223> OTHER INFORMATION: gap in alignment
<220> FEATURE:
<221> NAME/KEY: NON_CONS
<222> LOCATION: (67)..(68)
<223> OTHER INFORMATION: gap in alignment
```

-continued

<400> SEQUENCE: 53

Pro Asn Phe Val Thr Ala Met Leu Ser Lys Leu Arg Phe Glu Val Phe
1               5                   10                  15

Gln Pro Gly Asp Tyr Ile Ile Arg Glu Gly Ala Val Gly Lys Lys Met
            20                  25                  30

Tyr Phe Ile Gln His Gly Val Ala Gly Val Ile Thr Lys Ser Ser Lys
        35                  40                  45

Glu Met Lys Leu Thr Asp Gly Ser Tyr Phe Gly Glu Ile Cys Leu Leu
50                  55                  60

Thr Lys Gly Arg Arg Thr Ala Ser Val Arg Ala Asp Thr Tyr Cys Arg
65                  70                  75                  80

Leu Tyr Ser Leu Ser Val Asp Asn Phe Asn Glu Val Leu Glu Glu Tyr
                85                  90                  95

Pro Met Met Arg Arg Ala Phe Glu Thr Val Ala Ile Asp Arg Leu Asp
            100                 105                 110

Arg Ile Gly Lys Lys Asn Ser
            115

<210> SEQ ID NO 54
<211> LENGTH: 124
<212> TYPE: PRT
<213> ORGANISM: E. coli;
<220> FEATURE:
<221> NAME/KEY: NON_CONS
<222> LOCATION: (47)..(48)
<223> OTHER INFORMATION: gap in alignment
<220> FEATURE:
<221> NAME/KEY: NON_CONS
<222> LOCATION: (69)..(70)
<223> OTHER INFORMATION: gap in alignment

<400> SEQUENCE: 54

Asp Pro Thr Leu Glu Trp Phe Leu Ser His Cys His Ile His Lys Pro
1               5                   10                  15

Ser Lys Ser Thr Leu Ile His Gln Gly Glu Lys Ala Glu Thr Leu Tyr
            20                  25                  30

Tyr Ile Val Lys Gly Ser Val Ala Val Leu Ile Lys Asp Glu Glu Gly
        35                  40                  45

Lys Glu Met Ile Leu Ser Tyr Leu Asn Gln Gly Asp Phe Ile Gly Glu
50                  55                  60

Leu Gly Leu Phe Glu Glu Gly Gln Glu Arg Ser Ala Trp Val Arg Ala
65                  70                  75                  80

Lys Thr Ala Cys Glu Val Ala Glu Ile Ser Tyr Lys Lys Phe Arg Gln
            85                  90                  95

Leu Ile Gln Val Asn Pro Asp Ile Leu Met Arg Leu Ser Ala Gln Met
            100                 105                 110

Ala Arg Arg Leu Gln Val Thr Ser Glu Lys Val Gly
            115                 120

<210> SEQ ID NO 55
<211> LENGTH: 118
<212> TYPE: PRT
<213> ORGANISM: bovine;
<220> FEATURE:
<221> NAME/KEY: NON_CONS
<222> LOCATION: (45)..(46)
<223> OTHER INFORMATION: gap in alignment
<220> FEATURE:
<221> NAME/KEY: NON_CONS
<222> LOCATION: (54)..(55)

-continued

```
<223> OTHER INFORMATION: gap in alignment
<220> FEATURE:
<221> NAME/KEY: NON_CONS
<222> LOCATION: (65)..(66)
<223> OTHER INFORMATION: gap in alignment

<400> SEQUENCE: 55
```

| Asp | Asn | Glu | Arg | Ser | Asp | Ile | Phe | Asp | Ala | Met | Phe | Pro | Val | Ser | Phe |
|---|---|---|---|---|---|---|---|---|---|---|---|---|---|---|---|
| 1 | | | | 5 | | | | | 10 | | | | | 15 | |

| Ile | Ala | Gly | Glu | Thr | Val | Ile | Gln | Gln | Gly | Asp | Glu | Gly | Asp | Asn | Phe |
|---|---|---|---|---|---|---|---|---|---|---|---|---|---|---|---|
| | | | 20 | | | | | 25 | | | | | 30 | | |

| Tyr | Val | Ile | Asp | Gln | Gly | Glu | Met | Asp | Val | Tyr | Val | Asn | Asn | Glu | Trp |
|---|---|---|---|---|---|---|---|---|---|---|---|---|---|---|---|
| | | | 35 | | | | | 40 | | | | | 45 | | |

| Ala | Thr | Ser | Val | Gly | Glu | Gly | Gly | Ser | Phe | Gly | Glu | Leu | Ala | Leu | Ile |
|---|---|---|---|---|---|---|---|---|---|---|---|---|---|---|---|
| | 50 | | | | | 55 | | | | | | 60 | | | |

| Tyr | Gly | Thr | Pro | Arg | Ala | Ala | Thr | Val | Lys | Ala | Lys | Thr | Asn | Val | Lys |
|---|---|---|---|---|---|---|---|---|---|---|---|---|---|---|---|
| 65 | | | | | 70 | | | | | 75 | | | | | 80 |

| Leu | Trp | Gly | Ile | Asp | Arg | Asp | Ser | Tyr | Arg | Arg | Ile | Leu | Met | Gly | Ser |
|---|---|---|---|---|---|---|---|---|---|---|---|---|---|---|---|
| | | | | 85 | | | | | 90 | | | | | 95 | |

| Thr | Leu | Arg | Lys | Arg | Lys | Met | Tyr | Glu | Glu | Phe | Leu | Ser | Lys | Val | Ser |
|---|---|---|---|---|---|---|---|---|---|---|---|---|---|---|---|
| | | | 100 | | | | | 105 | | | | | 110 | | |

| Ile | Leu | Glu | Ser | Leu | Asp |
|---|---|---|---|---|---|
| | | | 115 | | |

```
<210> SEQ ID NO 56
<211> LENGTH: 121
<212> TYPE: PRT
<213> ORGANISM: bovine;
<220> FEATURE:
<221> NAME/KEY: NON_CONS
<222> LOCATION: (71)..(72)
<223> OTHER INFORMATION: gap in alignment

<400> SEQUENCE: 56
```

| Lys | Trp | Glu | Arg | Leu | Thr | Val | Ala | Asp | Ala | Leu | Glu | Pro | Val | Gln | Phe |
|---|---|---|---|---|---|---|---|---|---|---|---|---|---|---|---|
| 1 | | | | 5 | | | | | 10 | | | | | 15 | |

| Glu | Asp | Gly | Gln | Lys | Ile | Val | Val | Gln | Gly | Pro | Gly | Asp | Glu | Phe |
|---|---|---|---|---|---|---|---|---|---|---|---|---|---|---|
| | | | 20 | | | | | 25 | | | | | 30 | |

| Phe | Ile | Ile | Leu | Glu | Gly | Ser | Ala | Ala | Val | Leu | Gln | Arg | Arg | Ser | Glu |
|---|---|---|---|---|---|---|---|---|---|---|---|---|---|---|---|
| | | | 35 | | | | | 40 | | | | | 45 | | |

| Asn | Glu | Glu | Phe | Val | Glu | Val | Gly | Arg | Leu | Gly | Pro | Ser | Asp | Tyr | Phe |
|---|---|---|---|---|---|---|---|---|---|---|---|---|---|---|---|
| | 50 | | | | | 55 | | | | | | 60 | | | |

| Gly | Glu | Ile | Ala | Leu | Leu | Met | Asn | Arg | Pro | Arg | Ala | Ala | Thr | Val | Val |
|---|---|---|---|---|---|---|---|---|---|---|---|---|---|---|---|
| 65 | | | | | 70 | | | | | 75 | | | | | 80 |

| Ala | Arg | Gly | Pro | Leu | Lys | Cys | Val | Lys | Leu | Asp | Arg | Pro | Arg | Phe | Glu |
|---|---|---|---|---|---|---|---|---|---|---|---|---|---|---|---|
| | | | | 85 | | | | | 90 | | | | | 95 | |

| Arg | Val | Leu | Gly | Pro | Cys | Ser | Asp | Ile | Leu | Lys | Arg | Asn | Ile | Gln | Gln |
|---|---|---|---|---|---|---|---|---|---|---|---|---|---|---|---|
| | | | 100 | | | | | 105 | | | | | 110 | | |

| Tyr | Asn | Ser | Phe | Val | Ser | Leu | Ser | Val |
|---|---|---|---|---|---|---|---|---|
| | | | 115 | | | | | 120 |

```
<210> SEQ ID NO 57
<211> LENGTH: 126
<212> TYPE: PRT
<213> ORGANISM: bovine;
<220> FEATURE:
<221> NAME/KEY: NON_CONS
<222> LOCATION: (47)..(48)
<223> OTHER INFORMATION: gap in alignment
<220> FEATURE:
<221> NAME/KEY: NON_CONS
```

```
<222> LOCATION: (56)..(57)
<223> OTHER INFORMATION: gap in alignment

<400> SEQUENCE: 57

Ala Gly Leu Leu Val Glu Leu Val Leu Lys Leu Gln Pro Gln Val Tyr
1               5                   10                  15

Ser Gly Asp Tyr Ile Cys Lys Lys Gly Asp Ile Gly Arg Glu Met Tyr
                20                  25                  30

Ile Ile Lys Glu Gly Lys Leu Ala Val Val Ala Asp Asp Gly Ile Thr
                35                  40                  45

Gln Phe Val Val Leu Ser Asp Gly Ser Tyr Phe Gly Glu Ile Ser Ile
    50                  55                  60

Leu Asn Ile Lys Gly Ser Lys Ala Gly Asn Arg Arg Thr Ala Asn Ile
65                      70                  75                  80

Lys Ser Ile Gly Tyr Ser Asp Leu Phe Cys Leu Ser Lys Asp Asp Leu
                85                  90                  95

Met Glu Ala Leu Thr Glu Tyr Pro Asp Ala Lys Gly Met Leu Glu Glu
                100                 105                 110

Lys Gly Lys Gln Ile Leu Met Lys Asp Gly Leu Leu Asp Ile
                115                 120                 125

<210> SEQ ID NO 58
<211> LENGTH: 126
<212> TYPE: PRT
<213> ORGANISM: catfish;
<220> FEATURE:
<221> NAME/KEY: NON_CONS
<222> LOCATION: (7)..(8)
<223> OTHER INFORMATION: gap in alignment
<220> FEATURE:
<221> NAME/KEY: NON_CONS
<222> LOCATION: (47)..(48)
<223> OTHER INFORMATION: gap in alignment
<220> FEATURE:
<221> NAME/KEY: NON_CONS
<222> LOCATION: (56)..(57)
<223> OTHER INFORMATION: gap in alignment
<220> FEATURE:
<221> NAME/KEY: NON_CONS
<222> LOCATION: (66)..(67)
<223> OTHER INFORMATION: gap in alignment

<400> SEQUENCE: 58

Ala Gly Leu Leu Val Glu Leu Leu Lys Leu Arg Pro Gln Val Tyr Ser
1               5                   10                  15

Pro Gly Asp Tyr Ile Cys Arg Lys Gly Asp Ile Gly Lys Glu Met Tyr
                20                  25                  30

Ile Ile Lys Glu Gly Gln Leu Ala Val Val Ala Asp Asp Gly Val Thr
                35                  40                  45

Gln Phe Ala Leu Leu Thr Ala Gly Gly Cys Phe Gly Glu Ile Ser Ile
    50                  55                  60

Leu Asn Ile Gln Gly Ser Lys Met Gly Asn Arg Arg Thr Ala Asn Ile
65                      70                  75                  80

Arg Ser Ile Gly Tyr Ser Asp Leu Phe Cys Leu Ser Lys Asp Asp Leu
                85                  90                  95

Met Glu Ala Val Ala Glu Tyr Pro Asp Ala Gln Lys Val Leu Glu Glu
                100                 105                 110

Arg Gly Arg Glu Ile Leu Arg Lys Gln Gly Leu Leu Asp Glu
                115                 120                 125
```

-continued

```
<210> SEQ ID NO 59
<211> LENGTH: 126
<212> TYPE: PRT
<213> ORGANISM: Drosophila;
<220> FEATURE:
<221> NAME/KEY: NON_CONS
<222> LOCATION: (46)..(47)
<223> OTHER INFORMATION: gap in alignment
<220> FEATURE:
<221> NAME/KEY: NON_CONS
<222> LOCATION: (55)..(56)
<223> OTHER INFORMATION: gap in alignment

<400> SEQUENCE: 59

Asp Gly Cys Leu Arg Ala Leu Ala Met His Phe Met Met Ser His Ser
1               5                  10                  15

Ala Pro Gly Asp Leu Leu Tyr His Thr Gly Glu Ser Ile Asp Ser Leu
            20                  25                  30

Cys Phe Ile Val Thr Gly Ser Leu Glu Val Ile Gln Asp Asp Glu Val
        35                  40                  45

Val Ala Ile Leu Gly Lys Gly Asp Val Phe Gly Asp Gln Phe Trp Lys
50                  55                  60

Asp Ser Ala Val Gly Gln Ser Ala Ala Asn Val Arg Ala Leu Thr Tyr
65                  70                  75                  80

Cys Asp Leu His Ala Ile Lys Arg Asp Lys Leu Leu Glu Val Leu Asp
                85                  90                  95

Phe Tyr Ser Ala Phe Ala Asn Ser Phe Ala Arg Asn Leu Val Leu Thr
            100                 105                 110

Tyr Asn Leu Arg His Arg Leu Ile Phe Arg Arg Val Ala Asp
        115                 120                 125

<210> SEQ ID NO 60
<211> LENGTH: 128
<212> TYPE: PRT
<213> ORGANISM: Arabidopsis;
<220> FEATURE:
<221> NAME/KEY: NON_CONS
<222> LOCATION: (59)..(60)
<223> OTHER INFORMATION: gap in alignment
<220> FEATURE:
<221> NAME/KEY: NON_CONS
<222> LOCATION: (70)..(71)
<223> OTHER INFORMATION: gap in alignment

<400> SEQUENCE: 60

Arg Asn Phe Leu Phe Gln Leu Val Ser Asp Ile Asp Ala Glu Tyr Phe
1               5                  10                  15

Pro Pro Lys Glu Asp Ile Ile Leu Gln Asn Glu Ala Pro Thr Asp Leu
            20                  25                  30

Tyr Ile Leu Val Ser Gly Ala Val Asp Phe Thr Val Tyr Val Asp Gly
        35                  40                  45

His Asp Gln Phe Gln Gly Lys Ala Val Ile Gly Glu Thr Phe Gly Glu
50                  55                  60

Val Gly Val Leu Tyr Tyr Arg Pro Gln Pro Phe Thr Val Arg Thr Thr
65                  70                  75                  80

Glu Leu Ser Gln Ile Leu Arg Ile Ser Arg Thr Ser Leu Met Ser Ala
                85                  90                  95

Met His Ala His Ala Asp Asp Gly Arg Val Ile Met Asn Asn Leu Phe
            100                 105                 110

Met Lys Leu Arg Gly Gln Gln Ser Ile Ala Ile Asp Asp Ser Asn Thr
        115                 120                 125
```